(12) United States Patent
Borhan et al.

(10) Patent No.: US 9,732,127 B2
(45) Date of Patent: *Aug. 15, 2017

(54) COLORIMETRIC AND FLUORESCENT PROTEINS

(71) Applicant: Board of Trustees of Michigan State University, East Lansing, MI (US)

(72) Inventors: Babak Borhan, Okemos, MI (US); James Geiger, Webberville, MI (US); Wenjing Wang, Cambridge, MA (US); Chrysoula Vasileiou, East Lansing, MI (US); Kin Sing Lee, Davis, CA (US); Tetyana Berbasova, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/883,944

(22) Filed: Oct. 15, 2015

(65) Prior Publication Data

US 2016/0115210 A1 Apr. 28, 2016

Related U.S. Application Data

(63) Continuation of application No. 13/636,499, filed as application No. PCT/US2011/029616 on Mar. 23, 2011, now Pat. No. 9,169,305.

(60) Provisional application No. 61/340,831, filed on Mar. 23, 2011.

(51) Int. Cl.
*C07K 14/14* (2006.01)
*G01N 33/92* (2006.01)
*C07K 14/47* (2006.01)
*G01N 33/58* (2006.01)

(52) U.S. Cl.
CPC ........... *C07K 14/47* (2013.01); *G01N 33/582* (2013.01); *C07K 2319/60* (2013.01)

(58) Field of Classification Search
CPC .. C07K 14/47; C07K 2319/00; G01N 33/582; G01N 33/92
USPC ......................................... 530/350; 536/23.1
See application file for complete search history.

(56) References Cited

U.S. PATENT DOCUMENTS

| 5,654,137 | A | 8/1997 | Astrom et al. |
| 7,601,510 | B2 | 10/2009 | Kleinfeld et al. |
| 9,169,305 | B2 | 10/2015 | Borhan et al. |
| 2013/0157284 | A1 | 6/2013 | Borhan et al. |

FOREIGN PATENT DOCUMENTS

| WO | WO-2009092047 A1 | 6/2006 |
| WO | WO-2006122077 A2 | 11/2006 |
| WO | WO-2011119724 A2 | 9/2011 |
| WO | WO-2011119724 A3 | 9/2011 |

OTHER PUBLICATIONS

"U.S. Appl. No. 13/636,499, Advisory Action mailed May 8, 2015", 3 pgs.
"U.S. Appl. No. 13/636,499, Final Office Action mailed Feb. 2, 2015", 12 pgs.
"U.S. Appl. No. 13/636,499, Non Final Office Action mailed Aug. 6, 2014", 17 pgs.
"U.S. Appl. No. 13/636,499, Notice of Allowance mailed Jun. 12, 2015", 5 pgs.
"U.S. Appl. No. 13/636,499, Preliminary Amendment filed Sep. 21, 2012", 12 pgs.
"U.S. Appl. No. 13/636,499, PTO Response to Rule 312 Communication mailed Aug. 11, 2015", 2 pgs.
"U.S. Appl. No. 13/636,499, Response filed May 4, 2015 to Final Office Action mailed Feb. 2, 2015", 17 pgs.
"U.S. Appl. No. 13/636,499, Response filed Jun. 3, 2015 to Advisory Action mailed May 8, 2015", 17 pgs.
"U.S. Appl. No. 13/636,499, Response filed Jul. 21, 2014 to Restriction Requirement mailed May 21, 2014", 14 pgs.
"U.S. Appl. No. 13/636,499, Response filed Nov. 25, 2014 to Non Final Office Action mailed Aug. 6, 2014", 17 pgs.
"U.S. Appl. No. 13/636,499, Restriction Requirement mailed May 21, 2014", 8 pgs.
"International Serial No. PCT/US2011/029616, International Search Report mailed Aug. 23, 2011", 6 pgs.
"International Application Serial No. PCT/US2011/029616, International Search Report mailed Dec. 14, 2011", 8 pgs.
"International Application Serial No. PCT/US2011/029616, Preliminary Report on Patentability mailed Oct. 4, 2012", 12 pgs.
"International Application Serial No. PCT/US2011/029616, Written Opinion mailed Dec. 14, 2011", 11 pgs.
Budhu, Anuradha, et al., "Localization of the RAR Interaction Domain of Cellular Retinoic Acid Binding Protein-II", Journal of Molecular Biology, vol. 305, No. 4, (Jan. 26, 2001), 939-949.
Crist, Rachael M, et al., "Engineering a Rhodopsin Protein Mimic", Journal of the American Chemical Society, vol. 128, No. 14, (Apr. 12, 2006), 4522-4523.
Donato, L J, et al., "A fluorescence-based method for analyzing retinoic acid in biological samples", Analytical Biochemistry, vol. 357, No. 2, (Oct. 15, 2006), 249-256.
Li, Ellen, et al., "F Nuclear Magnetic Resonance Studies of 6-Fluorotryptophan-substituted Rat Cellular Retinol Binding Protein II Produced in *Escherichia coli*", The Journal of Biological Chemistry, vol. 265, No. 20, Jul. 15, 1990.
Loughney, et al., "Variation in the expression of cellular retinoid binding proteins in human endometrium throughout the menstrual cycle", Human Reproduction vol. 10(5), (1995), 1297-1304.
Vasileiou, Chrysoula, et al., "Dissection of the critical binding determinants of cellular retinoic acid binding protein II by mutagenesis and fluorescence binding assay", Proteins, vol. 76, No. 2, (Aug. 1, 2009), 281-290.

(Continued)

*Primary Examiner* — Karen Cochrane Carlson
(74) *Attorney, Agent, or Firm* — Schwegman Lundberg & Woessner, P.A.

(57) ABSTRACT

The invention relates to intracellular lipid binding proteins that bind retinoids and/or dye ligands and that are modified to transmit or emit light at a variety of different wavelengths.

24 Claims, 11 Drawing Sheets

(56) References Cited

OTHER PUBLICATIONS

Vasileiou, Chrysoula, et al., "Elucidating the exact role of engineered CRABPII residues for the formation of a retinal protonated Schiff base", Proteins, vol. 77, No. 4, (Dec. 2009), 812-822.

Wang, et al., "Reengineering of cellular retinol binding protein Ii into a rhodopsin protein mimic", Michigan State Univeristy, (Mar. 21, 2010), 1 pg.

| GFP | CRBP |
| GFP | CRBP | RB |
*FIG. 4A*
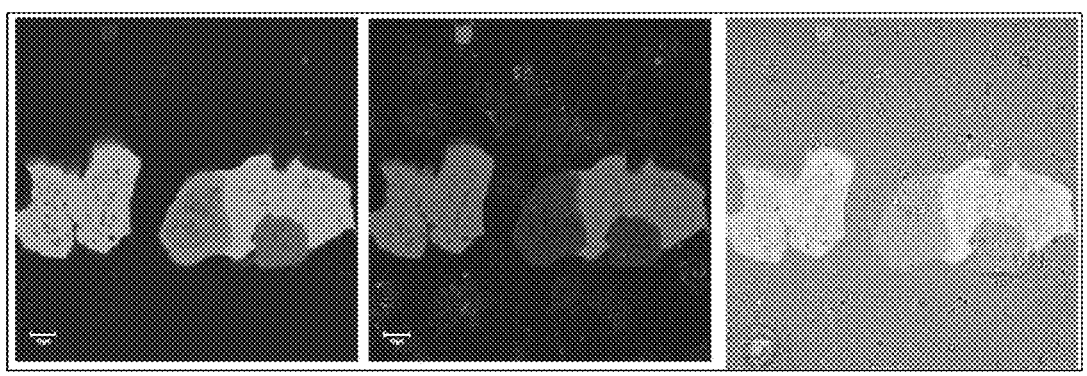
*FIG. 4B*
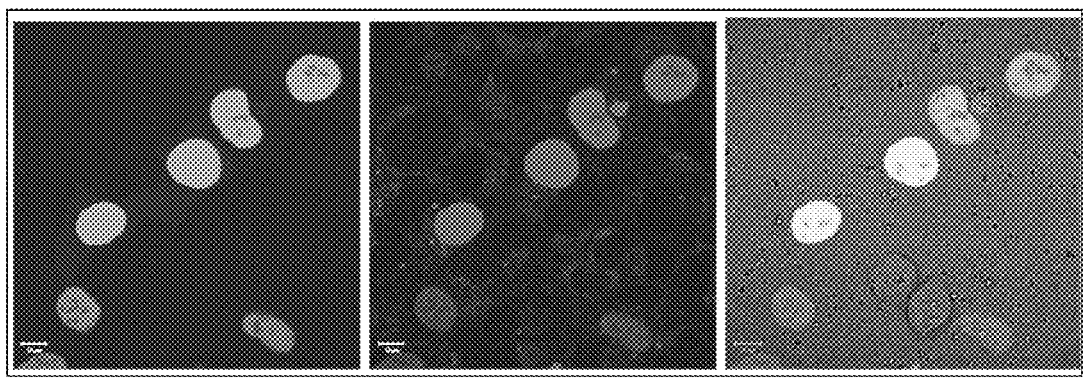
*FIG. 4C*

SEQUENCE LISTING

<160> NUMBER OF SEQ ID NOS: 47

<210> SEQ ID NO 1
<211> LENGTH: 134
<212> TYPE: PRT
<213> ORGANISM: Homo sapiens

<400> SEQUENCE: 1

```
Met Thr Arg Asp Gln Asn Gly Thr Trp Glu Met Glu Ser Asn Glu Asn
1               5                   10                  15

Phe Glu Gly Tyr Met Lys Ala Leu Asp Ile Asp Phe Ala Thr Arg Lys
            20                  25                  30

Ile Ala Val Arg Leu Thr Gln Thr Lys Val Ile Asp Gln Asp Gly Asp
        35                  40                  45

Asn Phe Lys Thr Lys Thr Thr Ser Thr Phe Arg Asn Tyr Asp Val Asp
50                  55                  60

Phe Thr Val Gly Val Glu Phe Asp Glu Tyr Thr Lys Ser Leu Asp Asn
65                  70                  75                  80

Arg His Val Lys Ala Leu Val Thr Trp Glu Gly Asp Val Leu Val Cys
                85                  90                  95

Val Gln Lys Gly Glu Lys Glu Asn Arg Gly Trp Lys Gln Trp Ile Glu
            100                 105                 110

Gly Asp Lys Leu Tyr Leu Glu Leu Thr Cys Gly Asp Gln Val Cys Arg
        115                 120                 125

Gln Val Phe Lys Lys Lys
    130
```

<210> SEQ ID NO 2
<211> LENGTH: 700
<212> TYPE: PRT
<213> ORGANISM: Homo sapiens

<400> SEQUENCE: 2

```
Cys Cys Thr Gly Cys Thr Cys Thr Thr Gly Cys Cys Ala Thr Cys
1               5                   10                  15

Cys Ala Cys Cys Ala Cys Ala Ala Cys Cys Cys Thr Cys Ala Cys
            20                  25                  30

Cys Gly Ala Ala Cys Ala Gly Thr Gly Gly Cys Cys Ala Cys Cys
        35                  40                  45

Ala Cys Cys Ala Thr Gly Ala Cys Ala Gly Gly Ala Cys Cys
    50                  55                  60

Ala Gly Ala Ala Thr Gly Gly Ala Ala Cys Cys Thr Gly Gly Gly Ala
65                  70                  75                  80

Gly Ala Thr Gly Gly Ala Gly Ala Gly Thr Ala Ala Thr Gly Ala Ala
                85                  90                  95

Ala Ala Cys Thr Thr Thr Gly Ala Gly Gly Gly Cys Thr Ala Cys Ala
            100                 105                 110

Thr Gly Ala Ala Gly Gly Cys Cys Cys Thr Gly Gly Ala Thr Ala Thr
        115                 120                 125

Thr Gly Ala Thr Thr Thr Thr Gly Cys Cys Ala Cys Cys Gly Cys
        130                 135                 140

Ala Ala Gly Ala Thr Thr Gly Cys Ala Gly Thr Ala Cys Gly Thr Cys
145                 150                 155                 160

Thr Cys Ala Cys Thr Cys Ala Gly Ala Cys Gly Ala Ala Gly Gly Thr
                165                 170                 175

Thr Ala Thr Thr Gly Ala Thr Cys Ala Ala Gly Ala Thr Gly Gly Thr
```

```
                180              185              190
Gly Ala Thr Ala Ala Cys Thr Thr Cys Ala Gly Ala Cys Ala Ala
            195              200              205
Ala Ala Ala Cys Cys Ala Cys Thr Ala Gly Cys Ala Cys Ala Thr Thr
        210              215              220
Cys Cys Gly Cys Ala Ala Cys Thr Ala Thr Gly Ala Thr Gly Thr Gly
225              230              235              240
Gly Ala Thr Thr Thr Cys Ala Cys Thr Gly Thr Thr Gly Gly Ala Gly
                245              250              255
Thr Ala Gly Ala Gly Thr Thr Thr Gly Ala Cys Gly Ala Gly Thr Ala
            260              265              270
Cys Ala Cys Ala Ala Ala Gly Ala Gly Cys Cys Thr Gly Gly Ala Thr
        275              280              285
Ala Ala Cys Cys Gly Gly Cys Ala Thr Gly Thr Ala Ala Gly Gly
        290              295              300
Cys Ala Cys Thr Gly Gly Thr Cys Ala Cys Cys Thr Gly Gly Ala
305              310              315              320
Ala Gly Gly Thr Gly Ala Thr Gly Thr Cys Cys Thr Thr Gly Thr Gly
                325              330              335
Thr Gly Thr Gly Thr Gly Cys Ala Ala Ala Gly Gly Gly Gly Gly
            340              345              350
Ala Gly Ala Ala Gly Gly Ala Gly Ala Ala Cys Cys Gly Cys Gly Gly
        355              360              365
Cys Thr Gly Gly Ala Ala Gly Cys Ala Gly Thr Gly Ala Thr Thr
    370              375              380
Gly Ala Gly Gly Gly Gly Ala Cys Ala Ala Gly Cys Thr Gly Thr
385              390              395              400
Ala Cys Cys Thr Gly Gly Ala Gly Cys Thr Gly Ala Cys Thr Gly
                405              410              415
Thr Gly Gly Thr Gly Ala Cys Cys Ala Gly Gly Thr Thr Gly Cys
            420              425              430
Cys Gly Thr Cys Ala Ala Gly Thr Gly Thr Thr Cys Ala Ala Ala Ala
        435              440              445
Ala Gly Ala Ala Ala Thr Gly Ala Thr Gly Gly Cys Gly Ala Cys Gly
    450              455              460
Thr Gly Gly Gly Ala Gly Gly Cys Cys Thr Gly Cys Ala Ala Gly
465              470              475              480
Cys Ala Cys Ala Ala Gly Cys Thr Cys Cys Cys Ala Cys Thr Gly
            485              490              495
Cys Cys Cys Ala Cys Ala Cys Thr Gly Ala Gly Thr Gly Gly Thr Cys
        500              505              510
Thr Ala Cys Thr Gly Gly Cys Thr Thr Thr Gly Ala Gly Ala Ala Ala
    515              520              525
Cys Ala Gly Cys Thr Gly Thr Gly Gly Gly Ala Cys Cys Thr Thr
        530              535              540
Cys Cys Cys Ala Cys Thr Cys Thr Thr Gly Ala Cys Ala Gly Ala
545              550              555              560
Cys Cys Cys Cys Ala Thr Thr Ala Ala Gly Gly Cys Ala Thr Cys Thr
                565              570              575
Gly Gly Gly Thr Gly Gly Gly Thr Thr Thr Thr Ala Ala Ala Cys Ala
            580              585              590
Gly Ala Ala Thr Gly Cys Cys Thr Ala Thr Gly Thr Ala Gly Cys Ala
        595              600              605
```

```
Gly Thr Gly Ala Thr Ala Gly Ala Cys Ala Thr Ala Thr Cys Cys
        610                 615                 620

Cys Cys Thr Cys Cys Thr Thr Thr Gly Ala Ala Ala Cys Cys Thr Ala
625                 630                 635                 640

Gly Cys Ala Thr Thr Ala Ala Ala Thr Gly Gly Ala Ala Ala Ala
        645                 650                 655

Cys Ala Ala Ala Ala Thr Thr Ala Cys Thr Cys Cys Cys Ala Thr
        660                 665                 670

Ala Thr Thr Thr Thr Gly Ala Ala Cys Cys Cys Thr Thr Thr Ala
        675                 680                 685

Ala Ala Ala Ala Ala Ala Ala Ala Ala Ala Ala Ala Ala
        690                 695                 700

<210> SEQ ID NO 3
<211> LENGTH: 134
<212> TYPE: PRT
<213> ORGANISM: Homo sapiens

<400> SEQUENCE: 3

Met Thr Arg Asp Gln Asn Gly Thr Trp Glu Met Glu Ser Asn Glu Asn
1               5                   10                  15

Phe Glu Gly Tyr Met Lys Ala Leu Asp Ile Asp Phe Ala Thr Pro Lys
            20                  25                  30

Ile Ala Val Arg Leu Thr Gln Thr Lys Val Ile Asp Gln Asp Gly Asp
        35                  40                  45

Asn Phe Lys Thr Lys Thr Thr Ser Thr Phe Arg Asn Tyr Asp Val Asp
50                  55                  60

Phe Thr Val Gly Val Glu Phe Asp Glu Tyr Thr Lys Ser Leu Asp Asn
65                  70                  75                  80

Arg His Val Lys Ala Leu Val Thr Trp Glu Gly Asp Val Leu Val Cys
                85                  90                  95

Val Gln Lys Gly Glu Lys Glu Asn Arg Gly Trp Lys Gln Trp Ile Glu
            100                 105                 110

Gly Asp Lys Leu Tyr Leu Glu Leu Thr Cys Gly Asp Gln Val Cys Arg
        115                 120                 125

Gln Val Phe Lys Lys Lys
    130

<210> SEQ ID NO 4
<211> LENGTH: 700
<212> TYPE: PRT
<213> ORGANISM: Homo sapiens

<400> SEQUENCE: 4

Cys Cys Thr Gly Cys Thr Cys Cys Thr Gly Cys Cys Ala Thr Cys
1               5                   10                  15

Cys Ala Cys Cys Ala Cys Ala Ala Ala Cys Cys Thr Cys Ala Cys
            20                  25                  30

Cys Gly Ala Ala Cys Cys Ala Gly Thr Gly Gly Cys Cys Ala Cys Cys
        35                  40                  45

Ala Cys Cys Ala Thr Gly Ala Cys Ala Ala Gly Gly Ala Cys Cys
50                  55                  60

Ala Gly Ala Ala Thr Gly Gly Ala Ala Cys Cys Thr Gly Gly Ala
65                  70                  75                  80

Gly Ala Thr Gly Gly Ala Gly Ala Gly Thr Ala Ala Thr Gly Ala Ala
                85                  90                  95
```

```
Ala Ala Cys Thr Thr Gly Ala Gly Gly Cys Thr Cys Ala
            100                 105                 110
Thr Gly Ala Ala Gly Gly Cys Cys Thr Gly Gly Ala Thr Ala Thr
            115                 120                 125
Thr Gly Ala Thr Thr Thr Gly Cys Cys Ala Cys Cys Gly Cys
            130                 135                 140
Ala Ala Gly Ala Thr Thr Gly Cys Ala Gly Thr Ala Cys Gly Thr Cys
145             150                 155                 160
Thr Cys Ala Cys Thr Cys Ala Gly Ala Cys Gly Ala Ala Gly Thr
                165                 170                 175
Thr Ala Thr Thr Gly Ala Thr Cys Ala Ala Gly Ala Thr Gly Gly Thr
            180                 185                 190
Gly Ala Thr Ala Ala Cys Thr Thr Cys Ala Ala Gly Ala Cys Ala Ala
            195                 200                 205
Ala Ala Ala Cys Cys Ala Cys Thr Ala Gly Cys Ala Cys Ala Thr Thr
210                 215                 220
Cys Cys Gly Cys Ala Ala Cys Thr Ala Thr Gly Ala Thr Gly Thr Gly
225                 230                 235                 240
Gly Ala Thr Thr Thr Cys Ala Cys Thr Gly Thr Thr Gly Gly Ala Gly
                245                 250                 255
Thr Ala Gly Ala Gly Thr Thr Thr Gly Ala Cys Gly Ala Gly Thr Ala
            260                 265                 270
Cys Ala Cys Ala Ala Ala Gly Ala Gly Cys Cys Thr Gly Gly Ala Thr
    275                 280                 285
Ala Ala Cys Cys Gly Gly Cys Ala Thr Gly Thr Thr Ala Ala Gly Gly
290                 295                 300
Cys Ala Cys Thr Gly Gly Thr Cys Ala Cys Cys Thr Gly Gly Gly Ala
305                 310                 315                 320
Ala Gly Gly Thr Gly Ala Thr Gly Thr Cys Cys Thr Thr Gly Thr Gly
                325                 330                 335
Thr Gly Thr Gly Thr Gly Cys Ala Ala Ala Ala Gly Gly Gly Gly Gly
            340                 345                 350
Ala Gly Ala Ala Gly Gly Ala Gly Ala Ala Cys Cys Gly Cys Gly Gly
            355                 360                 365
Cys Thr Gly Gly Ala Ala Gly Cys Ala Gly Thr Gly Gly Ala Thr Thr
    370                 375                 380
Gly Ala Gly Gly Gly Gly Gly Ala Cys Ala Ala Gly Cys Thr Gly Thr
385                 390                 395                 400
Ala Cys Cys Thr Gly Gly Ala Gly Cys Thr Gly Ala Cys Cys Thr Gly
                405                 410                 415
Thr Gly Gly Thr Gly Ala Cys Cys Ala Gly Thr Gly Thr Gly Cys
            420                 425                 430
Cys Gly Thr Cys Ala Ala Gly Thr Gly Thr Cys Ala Ala Ala Ala
    435                 440                 445
Ala Gly Ala Ala Ala Thr Gly Ala Thr Gly Gly Cys Ala Cys Gly
    450                 455                 460
Thr Gly Gly Ala Gly Gly Cys Cys Thr Cys Cys Ala Ala Gly
465                 470                 475                 480
Cys Ala Cys Ala Ala Gly Cys Thr Cys Cys Cys Ala Cys Thr Gly
                485                 490                 495
Cys Cys Cys Ala Cys Ala Cys Thr Gly Ala Gly Thr Gly Gly Thr Cys
                500                 505                 510
```

```
Thr Ala Cys Thr Gly Gly Cys Thr Thr Gly Ala Gly Ala Ala Ala
            515                 520                 525
Cys Ala Gly Cys Thr Gly Thr Gly Gly Gly Ala Cys Cys Thr Thr
530                 535                 540
Cys Cys Cys Ala Cys Thr Cys Thr Thr Gly Ala Cys Ala Gly Ala Gly
545                 550                 555                 560
Cys Cys Cys Cys Ala Thr Thr Ala Ala Gly Gly Cys Ala Thr Cys Thr
                565                 570                 575
Gly Gly Gly Thr Gly Gly Gly Thr Thr Thr Ala Ala Ala Cys Ala
                580                 585                 590
Gly Ala Ala Thr Gly Cys Cys Thr Ala Thr Gly Ala Gly Cys Ala
            595                 600                 605
Gly Thr Gly Ala Thr Ala Gly Ala Cys Ala Thr Ala Thr Cys Cys
            610                 615                 620
Cys Cys Thr Cys Cys Thr Thr Gly Ala Ala Ala Cys Cys Thr Ala
625                 630                 635                 640
Gly Cys Ala Thr Thr Ala Ala Ala Thr Gly Gly Ala Ala Ala Ala Ala
                645                 650                 655
Cys Ala Ala Ala Ala Thr Thr Ala Cys Thr Cys Cys Cys Ala Thr
                660                 665                 670
Ala Thr Thr Thr Thr Gly Ala Ala Ala Cys Cys Cys Thr Thr Thr Ala
            675                 680                 685
Ala Ala Ala Ala Ala Ala Ala Ala Ala Ala
            690                 695                 700

<210> SEQ ID NO 5
<211> LENGTH: 133
<212> TYPE: PRT
<213> ORGANISM: Homo sapiens

<400> SEQUENCE: 5

Thr Arg Asp Gln Asn Gly Thr Trp Glu Met Glu Ser Asn Glu Asn Phe
  1               5                  10                  15
Glu Gly Tyr Met Lys Ala Leu Asp Ile Asp Phe Ala Thr Arg Lys Ile
             20                  25                  30
Ala Val Arg Leu Thr Gln Thr Lys Val Ile Asp Gln Asp Gly Asp Asn
         35                  40                  45
Phe Lys Thr Lys Thr Thr Ser Thr Phe Arg Asn Tyr Asp Val Asp Phe
     50                  55                  60
Thr Val Gly Val Glu Phe Asp Glu Tyr Thr Lys Ser Leu Asp Asn Arg
 65                  70                  75                  80
His Val Lys Ala Leu Val Thr Trp Glu Gly Asp Val Leu Val Cys Val
                 85                  90                  95
Gln Lys Gly Glu Lys Glu Asn Arg Gly Trp Lys Gln Trp Ile Glu Gly
            100                 105                 110
Asp Lys Leu Tyr Leu Glu Leu Thr Cys Gly Asp Gln Val Cys Arg Gln
        115                 120                 125
Val Phe Lys Lys Lys
        130

<210> SEQ ID NO 6
<211> LENGTH: 133
<212> TYPE: PRT
<213> ORGANISM: Artificial Sequence
<220> FEATURE:
<223> OTHER INFORMATION: A synthetic peptide
```

<400> SEQUENCE: 6

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Lys Val Ile Asp Gln Asp Gly Asp Asn
        35                  40                  45

Phe Lys Thr Lys Thr Thr Ser Thr Phe Arg Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 7
<211> LENGTH: 133
<212> TYPE: PRT
<213> ORGANISM: Artificial Sequence
<220> FEATURE:
<223> OTHER INFORMATION: A synthetic peptide

<400> SEQUENCE: 7

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Leu Val Ile Asp Gln Asp Gly Asp Asn
        35                  40                  45

Phe Lys Thr Lys Thr Thr Ser Thr Phe Arg Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 8
<211> LENGTH: 133
<212> TYPE: PRT
<213> ORGANISM: Artificial Sequence
<220> FEATURE:
<223> OTHER INFORMATION: A synthetic peptide

<400> SEQUENCE: 8

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Lys Val Ile Asp Gln Asp Gly Asp Asn
        35                  40                  45

Phe Lys Asp Lys Thr Thr Ser Thr Phe Arg Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 9
<211> LENGTH: 133
<212> TYPE: PRT
<213> ORGANISM: Artificial Sequence
<220> FEATURE:
<223> OTHER INFORMATION: A synthetic peptide

<400> SEQUENCE: 9

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Leu Val Ile Asp Gln Asp Gly Asp Asn
        35                  40                  45

Phe Lys Thr Lys Thr Thr Ser Thr Phe Arg Asn Trp Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 10
<211> LENGTH: 133
<212> TYPE: PRT
<213> ORGANISM: Artificial Sequence
<220> FEATURE:
<223> OTHER INFORMATION: A synthetic peptide

<400> SEQUENCE: 10

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Leu Val Ile Asp Gln Asp Gly Asp Asn
        35                  40                  45

```
Phe Lys Val Lys Thr Thr Ser Thr Phe Arg Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
            115                 120                 125

Val Phe Lys Lys Lys
    130

<210> SEQ ID NO 11
<211> LENGTH: 133
<212> TYPE: PRT
<213> ORGANISM: Artificial Sequence
<220> FEATURE:
<223> OTHER INFORMATION: A synthetic peptide

<400> SEQUENCE: 11

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
                20                  25                  30

Ala Val Arg Leu Thr Gln Thr Leu Val Ile Asp Gln Asp Gly Asp Asn
            35                  40                  45

Phe Lys Thr Lys Thr Ser Thr Phe Phe Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
            115                 120                 125

Val Phe Lys Lys Lys
    130

<210> SEQ ID NO 12
<211> LENGTH: 133
<212> TYPE: PRT
<213> ORGANISM: Artificial Sequence
<220> FEATURE:
<223> OTHER INFORMATION: A synthetic peptide

<400> SEQUENCE: 12

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
                20                  25                  30

Ala Val Arg Leu Thr Gln Thr Leu Val Ile Asp Gln Asp Gly Asp Asn
            35                  40                  45

Phe Lys Thr Lys Thr Thr Ser Thr Phe Tyr Asn Tyr Asp Val Asp Phe
    50                  55                  60

Thr Val Gly Val Glu Phe Asp Glu Tyr Thr Lys Ser Leu Asp Asn Arg
```

```
                65                  70                  75                  80
His Val Lys Ala Leu Val Thr Trp Glu Gly Asp Val Leu Val Cys Val
                        85                  90                  95

Gln Lys Gly Glu Lys Glu Asn Arg Gly Trp Lys Lys Trp Ile Glu Gly
                    100                 105                 110

Asp Lys Leu Tyr Leu Glu Leu Thr Cys Gly Asp Gln Val Cys Arg Gln
                115                 120                 125

Val Phe Lys Lys Lys
            130

<210> SEQ ID NO 13
<211> LENGTH: 133
<212> TYPE: PRT
<213> ORGANISM: Artificial Sequence
<220> FEATURE:
<223> OTHER INFORMATION: A synthetic peptide

<400> SEQUENCE: 13

Thr Arg Asp Gln Asn Gly Thr Trp Glu Met Glu Ser Asn Glu Asn Phe
  1               5                  10                  15

Glu Gly Tyr Met Lys Ala Leu Asp Ile Asp Phe Ala Thr Arg Lys Ile
                 20                  25                  30

Ala Val Arg Leu Thr Gln Thr Leu Val Ile Asp Gln Asp Gly Asp Asn
             35                  40                  45

Phe Lys Val Lys Thr Thr Ser Thr Phe Tyr Asn Tyr Asp Val Asp Phe
         50                  55                  60

Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
                        85                  90                  95

Gln Lys Gly Glu Lys Glu Asn Arg Gly Trp Lys Lys Trp Ile Glu Gly
                    100                 105                 110

Asp Lys Leu Tyr Leu Glu Leu Thr Cys Gly Asp Gln Val Cys Arg Gln
                115                 120                 125

Val Phe Lys Lys Lys
            130

<210> SEQ ID NO 14
<211> LENGTH: 133
<212> TYPE: PRT
<213> ORGANISM: Artificial Sequence
<220> FEATURE:
<223> OTHER INFORMATION: A synthetic peptide

<400> SEQUENCE: 14

Thr Arg Asp Gln Asn Gly Thr Trp Glu Met Glu Ser Asn Glu Asn Phe
  1               5                  10                  15

Glu Gly Tyr Met Lys Ala Leu Asp Ile Asp Phe Ala Thr Arg Lys Ile
                 20                  25                  30

Ala Val Arg Leu Thr Gln Thr Leu Val Ile Asp Gln Asp Gly Asp Asn
             35                  40                  45

Phe Lys Val Lys Thr Thr Ser Thr Phe Trp Asn Tyr Asp Val Asp Phe
         50                  55                  60

Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
                        85                  90                  95
```

Gln Lys Gly Glu Lys Glu Asn Arg Gly Trp Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 15
<211> LENGTH: 133
<212> TYPE: PRT
<213> ORGANISM: Artificial Sequence
<220> FEATURE:
<223> OTHER INFORMATION: A synthetic peptide

<400> SEQUENCE: 15

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 16
<211> LENGTH: 133
<212> TYPE: PRT
<213> ORGANISM: Artificial Sequence
<220> FEATURE:
<223> OTHER INFORMATION: A synthetic peptide

<400> SEQUENCE: 16

Thr Arg Asp Gln Asn Gly Thr Trp Glu Met Glu Ser Asn Glu Asn Phe
1               5                   10                  15

Glu Gly Tyr Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Trp Ile Glu Gly
            100                 105                 110

Asp Lys Leu Tyr Leu Glu Leu Thr Cys Gly Asp Gln Val Cys Arg Gln
        115                 120                 125

```
Val Phe Lys Lys Lys
    130

<210> SEQ ID NO 17
<211> LENGTH: 133
<212> TYPE: PRT
<213> ORGANISM: Artificial Sequence
<220> FEATURE:
<223> OTHER INFORMATION: A synthetic peptide

<400> SEQUENCE: 17

Thr Arg Asp Gln Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 18
<211> LENGTH: 133
<212> TYPE: PRT
<213> ORGANISM: Artificial Sequence
<220> FEATURE:
<223> OTHER INFORMATION: A synthetic peptide

<400> SEQUENCE: 18

Thr Arg Asp Arg Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130
```

```
<210> SEQ ID NO 19
<211> LENGTH: 133
<212> TYPE: PRT
<213> ORGANISM: Artificial Sequence
<220> FEATURE:
<223> OTHER INFORMATION: A synthetic peptide

<400> SEQUENCE: 19

Thr Arg Asp Arg Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
50                  55                  60

Thr Val Gly Val Glu Phe Asp Glu Tyr Thr Lys Ser Leu Asp Asn Arg
65              70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
        130

<210> SEQ ID NO 20
<211> LENGTH: 133
<212> TYPE: PRT
<213> ORGANISM: Artificial Sequence
<220> FEATURE:
<223> OTHER INFORMATION: A synthetic peptide

<400> SEQUENCE: 20

Thr Arg Asp Trp Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
50                  55                  60

Thr Val Gly Val Glu Phe Asp Glu Tyr Thr Lys Ser Leu Asp Asn Arg
65              70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
        130

<210> SEQ ID NO 21
<211> LENGTH: 133
<212> TYPE: PRT
<213> ORGANISM: Artificial Sequence
<220> FEATURE:
```

<223> OTHER INFORMATION: A synthetic peptide

<400> SEQUENCE: 21

Thr Arg Asp Asn Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 22
<211> LENGTH: 133
<212> TYPE: PRT
<213> ORGANISM: Artificial Sequence
<220> FEATURE:
<223> OTHER INFORMATION: A synthetic peptide

<400> SEQUENCE: 22

Thr Arg Asp Thr Asn Gly Thr Trp Glu Met Glu Ser Asn Glu Asn Phe
1               5                   10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
        35                  40                  45

Phe Lys Val Lys Cys Thr Ser Thr Phe Trp Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130

<210> SEQ ID NO 23
<211> LENGTH: 133
<212> TYPE: PRT
<213> ORGANISM: Artificial Sequence
<220> FEATURE:
<223> OTHER INFORMATION: A synthetic peptide

<400> SEQUENCE: 23

Thr Arg Asp Glu Asn Gly Thr Trp Glu Met Glu Ser Asn Glu Asn Phe

```
                 1               5                   10                  15
            Glu Gly Trp Met Lys Ala Leu Asp Ile Asp Phe Ala Leu Arg Lys Ile
                            20                  25                  30

Ala Val Arg Leu Thr Gln Thr Leu Val Ile Asp Gln Asp Gly Asp Asn
                            35                  40                  45

Phe Lys Val Lys Cys Thr Ser Thr Phe Trp Asn Tyr Asp Val Asp Phe
                            50                  55                  60

Thr Val Gly Val Glu Phe Asp Glu Tyr Thr Lys Ser Leu Asp Asn Arg
             65                  70                  75                  80

His Val Lys Ala Leu Val Thr Trp Glu Gly Asp Val Leu Val Cys Val
                            85                  90                  95

Gln Lys Gly Glu Lys Glu Asn Arg Gly Trp Lys Lys Trp Ile Glu Gly
                            100                 105                 110

Asp Lys Leu Tyr Leu Glu Leu Thr Cys Gly Asp Gln Val Cys Arg Gln
                            115                 120                 125

Val Phe Lys Lys Lys
                            130

<210> SEQ ID NO 24
<211> LENGTH: 133
<212> TYPE: PRT
<213> ORGANISM: Artificial Sequence
<220> FEATURE:
<223> OTHER INFORMATION: A synthetic peptide

<400> SEQUENCE: 24

Thr Arg Asp His Asn Gly Thr Trp Glu Met Glu Ser Asn Glu Asn Phe
             1               5                   10                  15

Glu Gly Trp Met Lys Ala Leu Asp Ile Asp Phe Ala Leu Arg Lys Ile
                            20                  25                  30

Ala Val Arg Leu Thr Gln Thr Leu Val Ile Asp Gln Asp Gly Asp Asn
                            35                  40                  45

Phe Lys Val Lys Cys Thr Ser Thr Phe Trp Asn Tyr Asp Val Asp Phe
                            50                  55                  60

Thr Val Gly Val Glu Phe Asp Glu Tyr Thr Lys Ser Leu Asp Asn Arg
             65                  70                  75                  80

His Val Lys Ala Leu Val Thr Trp Glu Gly Asp Val Leu Val Cys Val
                            85                  90                  95

Gln Lys Gly Glu Lys Glu Asn Arg Gly Trp Lys Lys Trp Ile Glu Gly
                            100                 105                 110

Asp Lys Leu Tyr Leu Glu Leu Thr Cys Gly Asp Gln Val Cys Arg Gln
                            115                 120                 125

Val Phe Lys Lys Lys
                            130

<210> SEQ ID NO 25
<211> LENGTH: 133
<212> TYPE: PRT
<213> ORGANISM: Artificial Sequence
<220> FEATURE:
<223> OTHER INFORMATION: A synthetic peptide

<400> SEQUENCE: 25

Thr Arg Asp Lys Asn Gly Thr Trp Glu Met Glu Ser Asn Glu Asn Phe
             1               5                   10                  15

Glu Gly Trp Met Lys Ala Leu Asp Ile Asp Phe Ala Leu Arg Lys Ile
                            20                  25                  30
```

Ala Val Arg Leu Thr Gln Thr Leu Val Ile Asp Gln Asp Gly Asp Asn
            35                  40                  45

Phe Lys Val Lys Cys Thr Ser Thr Phe Trp Asn Tyr Asp Val Asp Phe
 50                  55                  60

Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
            85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
            115                 120                 125

Val Phe Lys Lys Lys
            130

<210> SEQ ID NO 26
<211> LENGTH: 133
<212> TYPE: PRT
<213> ORGANISM: Artificial Sequence
<220> FEATURE:
<223> OTHER INFORMATION: A synthetic peptide

<400> SEQUENCE: 26

Thr Arg Asp Leu Asn Gly Thr Trp Glu Met Glu Ser Asn Glu Asn Phe
 1                   5                  10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
            35                  40                  45

Phe Lys Val Lys Cys Thr Ser Thr Phe Trp Asn Tyr Asp Val Asp Phe
 50                  55                  60

Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
            85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
            115                 120                 125

Val Phe Lys Lys Lys
            130

<210> SEQ ID NO 27
<211> LENGTH: 133
<212> TYPE: PRT
<213> ORGANISM: Artificial Sequence
<220> FEATURE:
<223> OTHER INFORMATION: A synthetic peptide

<400> SEQUENCE: 27

Thr Arg Asp Phe Asn Gly Thr Trp Glu Met Glu Ser Asn Glu Asn Phe
 1                   5                  10                  15

Glu Gly Trp Met Lys Ala Leu Asp Ile Asp Phe Ala Leu Arg Lys Ile
            20                  25                  30

Ala Val Arg Leu Thr Gln Thr Leu Val Ile Asp Gln Asp Gly Asp Asn
            35                  40                  45

Phe Lys Val Lys Cys Thr Ser Thr Phe Trp Asn Tyr Asp Val Asp Phe
 50                  55                  60

```
Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
                 85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
        130

<210> SEQ ID NO 28
<211> LENGTH: 133
<212> TYPE: PRT
<213> ORGANISM: Artificial Sequence
<220> FEATURE:
<223> OTHER INFORMATION: A synthetic peptide

<400> SEQUENCE: 28

Thr Arg Asp Arg Asn Gly Thr Trp Glu Met Glu Ser Asn Glu Asn Phe
 1               5                  10                  15

Glu Gly Trp Met Lys Ala Leu Asp Ile Asp Phe Ala Leu Arg Lys Ile
             20                  25                  30

Trp Val Arg Leu Thr Gln Thr Leu Val Ile Asp Gln Asp Gly Asp Asn
         35                  40                  45

Phe Lys Val Lys Cys Thr Ser Thr Phe Trp Asn Tyr Asp Val Asp Phe
 50                  55                  60

Thr Val Gly Val Glu Phe Asp Glu Tyr Thr Lys Ser Leu Asp Asn Arg
 65                  70                  75                  80

His Val Lys Ala Leu Val Thr Trp Glu Gly Asp Val Leu Val Cys Val
                 85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
        130

<210> SEQ ID NO 29
<211> LENGTH: 133
<212> TYPE: PRT
<213> ORGANISM: Rattus norvegicus

<400> SEQUENCE: 29

Thr Lys Asp Gln Asn Gly Thr Trp Glu Met Glu Ser Asn Glu Asn Phe
 1               5                  10                  15

Glu Gly Tyr Met Lys Ala Leu Asp Ile Asp Phe Ala Thr Arg Lys Ile
             20                  25                  30

Ala Val Arg Leu Thr Gln Thr Lys Ile Ile Val Gln Asp Gly Asp Asn
         35                  40                  45

Phe Lys Thr Lys Thr Asn Ser Thr Phe Arg Asn Tyr Asp Leu Asp Phe
 50                  55                  60

Thr Val Gly Val Glu Phe Asp Glu His Thr Lys Gly Leu Asp Gly Arg
 65                  70                  75                  80

Asn Val Lys Thr Leu Val Thr Trp Glu Gly Asn Thr Leu Val Cys Val
                 85                  90                  95
```

-continued

Gln Lys Gly Glu Lys Glu Asn Arg Gly Trp Lys Gln Trp Val Glu Gly
                100                 105                 110

Asp Lys Leu Tyr Leu Glu Leu Thr Cys Gly Asp Gln Val Cys Arg Gln
            115                 120                 125

Val Phe Lys Lys Lys
            130

<210> SEQ ID NO 30
<211> LENGTH: 674
<212> TYPE: PRT
<213> ORGANISM: Rattus norvegicus

<400> SEQUENCE: 30

Gly Cys Ala Gly Cys Thr Thr Gly Thr Thr Cys Cys Thr Thr Cys Ala
1               5                   10                  15

Cys Gly Gly Thr Cys Ala Cys Cys Ala Ala Cys Gly Thr Cys Cys
            20                  25                  30

Gly Cys Ala Thr Cys Ala Ala Ala Cys Cys Ala Gly Ala Gly Gly Cys
            35                  40                  45

Cys Gly Cys Cys Ala Thr Cys Ala Thr Gly Ala Cys Gly Ala Ala Gly
        50                  55                  60

Gly Ala Cys Cys Ala Gly Ala Ala Thr Gly Gly Ala Ala Cys Cys Thr
65                  70                  75                  80

Gly Gly Gly Ala Ala Thr Gly Gly Ala Gly Ala Gly Thr Ala Ala
            85                  90                  95

Thr Gly Ala Gly Ala Ala Cys Thr Thr Thr Gly Ala Ala Gly Gly Cys
            100                 105                 110

Thr Ala Cys Ala Thr Gly Ala Ala Gly Gly Cys Cys Cys Thr Ala Gly
            115                 120                 125

Ala Thr Ala Thr Thr Gly Ala Thr Thr Thr Gly Cys Cys Ala Cys
            130                 135                 140

Cys Cys Gly Cys Ala Ala Gly Ala Thr Gly Cys Ala Gly Thr Gly
145                 150                 155                 160

Cys Gly Thr Cys Thr Gly Ala Cys Thr Cys Ala Gly Ala Cys Gly Ala
            165                 170                 175

Ala Gly Ala Thr Cys Ala Thr Cys Gly Thr Cys Ala Ala Gly Ala
            180                 185                 190

Cys Gly Gly Thr Gly Ala Thr Ala Ala Cys Thr Thr Cys Ala Ala Gly
            195                 200                 205

Ala Cys Ala Ala Ala Ala Cys Cys Ala Ala Cys Ala Gly Cys Ala
            210                 215                 220

Cys Gly Thr Thr Cys Cys Gly Cys Ala Ala Cys Thr Ala Thr Gly Ala
225                 230                 235                 240

Cys Cys Thr Ala Gly Ala Thr Thr Thr Cys Ala Cys Ala Gly Thr Gly
            245                 250                 255

Gly Gly Gly Gly Thr Gly Gly Ala Gly Thr Thr Thr Gly Ala Cys Gly
            260                 265                 270

Ala Ala Cys Ala Cys Ala Cys Ala Ala Gly Gly Gly Thr Cys Thr
            275                 280                 285

Gly Gly Ala Thr Gly Gly Cys Cys Gly Gly Ala Ala Cys Gly Thr Cys
            290                 295                 300

Ala Ala Gly Ala Cys Cys Cys Thr Ala Gly Thr Cys Ala Cys Thr
305                 310                 315                 320

Gly Gly Gly Ala Ala Gly Gly Ala Ala Ala Cys Ala Cys Cys Cys Thr
            325                 330                 335

Gly Gly Thr Gly Thr Gly Thr Gly Cys Ala Gly Ala Ala Ala
            340                 345                 350

Gly Gly Gly Gly Ala Gly Ala Ala Gly Gly Ala Gly Ala Thr Cys
        355                 360                 365

Gly Thr Gly Gly Cys Thr Gly Gly Ala Gly Cys Ala Gly Thr Gly
    370                 375                 380

Gly Gly Thr Cys Gly Ala Gly Gly Ala Gly Ala Cys Ala Ala Gly
385                 390                 395                 400

Cys Thr Gly Thr Ala Cys Cys Thr Gly Ala Gly Cys Thr Gly Ala
            405                 410                 415

Cys Cys Thr Gly Cys Gly Gly Thr Gly Ala Cys Ala Gly Gly Thr
        420                 425                 430

Gly Thr Gly Thr Cys Gly Ala Cys Ala Ala Gly Thr Gly Thr Cys
    435                 440                 445

Ala Ala Ala Ala Ala Gly Ala Ala Gly Thr Gly Ala Thr Gly Gly
        450                 455                 460

Cys Cys Cys Ala Gly Gly Gly Ala Ala Gly Cys Cys Thr Gly Gly
465                 470                 475                 480

Ala Ala Cys Ala Thr Gly Thr Gly Thr Ala Gly Ala Gly Thr Cys
            485                 490                 495

Thr Cys Thr Gly Cys Cys Ala Thr Thr Cys Thr Gly Ala Ala Ala
        500                 505                 510

Gly Cys Ala Gly Cys Ala Thr Thr Gly Gly Gly Ala Cys Thr Cys
    515                 520                 525

Cys Thr Gly Gly Thr Thr Cys Cys Thr Gly Ala Cys Ala Gly Ala
        530                 535                 540

Cys Cys Cys Cys Cys Cys Thr Thr Gly Cys Ala Thr Cys Ala Cys
545                 550                 555                 560

Thr Gly Cys Cys Thr Gly Gly Thr Thr Gly Ala Ala Ala Cys
            565                 570                 575

Ala Gly Gly Gly Thr Gly Thr Gly Thr Thr Ala Ala Ala Gly Gly Ala
        580                 585                 590

Ala Cys Cys Thr Ala Cys Cys Cys Cys Thr Cys Cys Cys Cys
            595                 600                 605

Thr Thr Ala Gly Ala Ala Cys Cys Thr Ala Thr Thr Ala Thr Ala
        610                 615                 620

Ala Ala Thr Ala Ala Ala Ala Ala Ala Cys Ala Ala Ala Ala Cys
625                 630                 635                 640

Ala Thr Cys Cys Thr Cys Thr Cys Gly Gly Cys Cys Thr Thr Gly
            645                 650                 655

Ala Ala Ala Ala Ala Ala Ala Ala Ala Ala Ala Ala Ala Ala Ala
        660                 665                 670

Ala Ala

<210> SEQ ID NO 31
<211> LENGTH: 133
<212> TYPE: PRT
<213> ORGANISM: Mus musculus

<400> SEQUENCE: 31

Thr Lys Asp Gln Asn Gly Thr Trp Glu Met Glu Ser Asn Glu Asn Phe
1               5                   10                  15

Glu Gly Tyr Met Lys Ala Leu Asp Ile Asp Phe Ala Thr Arg Lys Ile
            20                  25                  30

Ala Val Arg Leu Thr Gln Thr Lys Ile Ile Thr Gln Asp Gly Asp Asn
         35                   40                  45

Phe Lys Thr Lys Thr Asn Ser Thr Phe Arg Asn Tyr Asp Leu Asp Phe
 50                   55                  60

Thr Val Gly Val Glu Phe Asp Glu His Thr Lys Gly Leu Asp Gly Arg
 65                   70                  75                  80

His Val Lys Thr Leu Val Thr Trp Glu Gly Asn Thr Leu Val Cys Val
                 85                  90                  95

Gln Lys Gly Glu Lys Glu Asn Arg Gly Trp Lys Gln Trp Val Glu Gly
                100                 105                 110

Asp Lys Leu Tyr Leu Glu Leu Thr Cys Gly Asp Gln Val Cys Arg Gln
                115                 120                 125

Val Phe Lys Lys Lys
        130

<210> SEQ ID NO 32
<211> LENGTH: 672
<212> TYPE: PRT
<213> ORGANISM: Mus musculus

<400> SEQUENCE: 32

Ala Thr Thr Thr Ala Gly Cys Ala Thr Ala Gly Thr Cys Thr Cys Cys
  1               5                  10                  15

Cys Thr Gly Cys Ala Gly Cys Cys Gly Thr Thr Cys Cys Thr Thr Thr
             20                  25                  30

Cys Ala Cys Ala Thr Cys Ala Cys Cys Gly Ala Ala Cys Cys Gly Thr
             35                  40                  45

Cys Cys Ala Cys Ala Thr Cys Ala Ala Ala Cys Cys Ala Gly Ala Gly
         50                  55                  60

Gly Cys Cys Ala Cys Cys Ala Thr Cys Ala Thr Gly Ala Cys Gly Ala
 65                  70                  75                  80

Ala Gly Gly Ala Cys Cys Ala Ala Ala Thr Gly Gly Ala Ala Ala Cys
                 85                  90                  95

Cys Thr Gly Gly Gly Ala Ala Thr Gly Gly Ala Gly Ala Gly Thr
                100                 105                 110

Ala Ala Thr Gly Ala Gly Ala Ala Cys Thr Thr Thr Gly Ala Ala Gly
                115                 120                 125

Gly Cys Thr Ala Cys Ala Thr Gly Ala Ala Gly Gly Cys Cys Cys Thr
            130                 135                 140

Ala Gly Ala Thr Ala Thr Thr Gly Ala Thr Thr Thr Gly Cys Cys
145                 150                 155                 160

Ala Cys Cys Cys Gly Cys Ala Ala Gly Ala Thr Cys Gly Cys Ala Gly
                165                 170                 175

Thr Gly Cys Gly Thr Cys Thr Gly Ala Cys Thr Cys Ala Gly Ala Cys
                180                 185                 190

Gly Ala Ala Gly Ala Thr Cys Ala Thr Cys Ala Cys Ala Ala
                195                 200                 205

Gly Ala Cys Gly Gly Thr Gly Ala Thr Ala Ala Cys Thr Thr Cys Ala
            210                 215                 220

Ala Gly Ala Cys Gly Ala Ala Ala Cys Ala Cys Ala Gly
225                 230                 235                 240

Cys Ala Cys Gly Thr Thr Cys Cys Gly Cys Ala Ala Cys Thr Ala Cys
                245                 250                 255

Gly Ala Cys Cys Thr Gly Gly Ala Thr Thr Thr Cys Ala Cys Cys Gly

```
                260                 265                 270
Thr Cys Gly Gly Gly Thr Gly Gly Ala Gly Thr Thr Gly Ala
            275                 280                 285
Cys Gly Ala Ala Cys Ala Cys Ala Cys Ala Ala Gly Gly Gly Cys
            290                 295                 300
Cys Thr Gly Gly Ala Cys Gly Gly Cys Cys Gly Ala Cys Ala Thr Gly
305                 310                 315                 320
Thr Cys Ala Ala Gly Ala Cys Cys Thr Gly Gly Thr Cys Ala Cys
                325                 330                 335
Cys Thr Gly Gly Gly Ala Ala Gly Gly Cys Ala Ala Cys Ala Cys Cys
            340                 345                 350
Cys Thr Cys Gly Thr Gly Thr Gly Thr Gly Cys Ala Gly Ala
            355                 360                 365
Ala Ala Gly Gly Gly Gly Ala Gly Ala Ala Gly Gly Ala Gly Ala Ala
            370                 375                 380
Cys Cys Gly Thr Gly Gly Cys Thr Gly Gly Ala Ala Gly Cys Ala Gly
385                 390                 395                 400
Thr Gly Gly Gly Thr Gly Gly Ala Gly Gly Ala Gly Ala Cys Ala
                405                 410                 415
Ala Gly Cys Thr Gly Thr Ala Cys Cys Thr Gly Gly Ala Gly Cys Thr
                420                 425                 430
Gly Ala Cys Cys Thr Gly Cys Gly Gly Cys Gly Ala Cys Cys Ala Gly
                435                 440                 445
Gly Thr Gly Thr Gly Cys Cys Gly Ala Cys Ala Ala Gly Thr Gly Thr
            450                 455                 460
Thr Cys Ala Ala Ala Ala Gly Ala Ala Gly Thr Gly Ala Thr Gly
465                 470                 475                 480
Gly Gly Cys Ala Cys Gly Gly Ala Ala Gly Cys Cys Thr Gly
                485                 490                 495
Gly Ala Ala Cys Ala Thr Gly Thr Gly Cys Ala Gly Ala Gly Thr Thr
                500                 505                 510
Cys Thr Cys Thr Gly Cys Cys Ala Gly Thr Thr Cys Cys Cys Cys Ala
            515                 520                 525
Ala Ala Gly Cys Ala Gly Cys Ala Thr Gly Gly Gly Ala Cys Thr
            530                 535                 540
Cys Cys Thr Cys Cys Ala Thr Thr Cys Cys Thr Gly Ala Cys Ala
545                 550                 555                 560
Gly Ala Gly Cys Cys Cys Cys Thr Thr Ala Cys Ala Thr Cys Ala
                565                 570                 575
Thr Cys Thr Gly Cys Cys Thr Gly Gly Gly Thr Thr Ala Ala Ala
            580                 585                 590
Cys Thr Gly Gly Ala Gly Thr Gly Thr Ala Thr Ala Ala Ala Gly
            595                 600                 605
Gly Ala Ala Cys Cys Thr Ala Cys Cys Cys Cys Cys Thr Cys Cys
            610                 615                 620
Cys Ala Gly Cys Cys Cys Cys Cys Cys Cys Cys Ala Ala
625                 630                 635                 640
Gly Cys Thr Thr Gly Thr Thr Ala Thr Ala Ala Gly Ala Ala
                645                 650                 655
Ala Cys Ala Ala Ala Thr Gly Thr Cys Cys Thr Cys Thr Cys Ala
                660                 665                 670
```

<210> SEQ ID NO 33

```
<211> LENGTH: 138
<212> TYPE: PRT
<213> ORGANISM: Homo sapiens

<400> SEQUENCE: 33

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Ala Val Ala Ala Ala Ser Lys Pro Ala Val Glu Ile Lys Gln Glu Gly
        35                  40                  45

Asp Thr Phe Tyr Ile Lys Thr Ser Thr Thr Val Arg Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Arg
            100                 105                 110

Glu Leu Thr Asn Asp Gly Glu Leu Ile Leu Thr Met Thr Ala Asp Asp
        115                 120                 125

Val Val Cys Thr Arg Val Tyr Val Arg Glu
    130                 135

<210> SEQ ID NO 34
<211> LENGTH: 1075
<212> TYPE: PRT
<213> ORGANISM: Homo sapiens

<400> SEQUENCE: 34

Gly Ala Thr Thr Cys Ala Ala Gly Thr Gly Cys Thr Gly Gly Cys Thr
1               5                   10                  15

Thr Thr Gly Cys Gly Thr Cys Cys Gly Cys Thr Thr Cys Cys Cys Cys
            20                  25                  30

Ala Thr Cys Cys Ala Cys Thr Thr Ala Cys Thr Ala Gly Cys Gly Cys
        35                  40                  45

Ala Gly Gly Ala Gly Ala Ala Gly Gly Cys Thr Ala Thr Cys Thr Cys
    50                  55                  60

Gly Gly Thr Cys Cys Cys Ala Gly Ala Gly Ala Ala Gly Cys Cys
65                  70                  75                  80

Thr Gly Gly Ala Cys Cys Cys Ala Cys Ala Cys Gly Cys Gly Gly Gly
                85                  90                  95

Cys Thr Ala Gly Ala Thr Cys Ala Gly Ala Gly Ala Ala Cys Cys
            100                 105                 110

Thr Gly Ala Cys Gly Ala Cys Cys Cys Gly Gly Cys Ala Cys Gly
            115                 120                 125

Gly Cys Gly Ala Cys Gly Thr Cys Thr Cys Thr Thr Thr Thr Gly Ala
        130                 135                 140

Cys Thr Ala Ala Ala Ala Gly Ala Cys Ala Gly Thr Gly Thr Cys Cys
145                 150                 155                 160

Ala Gly Thr Gly Cys Thr Cys Cys Ala Gly Cys Cys Thr Ala Gly Gly
                165                 170                 175

Ala Gly Thr Cys Thr Ala Cys Gly Gly Gly Gly Ala Cys Cys Gly Cys
            180                 185                 190

Cys Thr Cys Cys Cys Gly Cys Gly Cys Cys Gly Cys Ala Cys Cys
        195                 200                 205
```

```
Ala Thr Gly Cys Cys Cys Ala Ala Cys Thr Thr Cys Thr Cys Thr Gly
            210                 215                 220
Gly Cys Ala Ala Cys Thr Gly Gly Ala Ala Ala Thr Cys Ala Thr
225                 230                 235                 240
Cys Cys Gly Ala Thr Cys Gly Gly Ala Ala Ala Cys Thr Thr Cys
                245                 250                 255
Gly Ala Gly Gly Ala Ala Thr Thr Gly Cys Thr Cys Ala Ala Ala Gly
                260                 265                 270
Thr Gly Cys Thr Gly Gly Gly Gly Thr Gly Ala Ala Thr Gly Thr
            275                 280                 285
Gly Ala Thr Gly Cys Thr Gly Ala Gly Gly Ala Gly Ala Thr Thr
            290                 295                 300
Gly Cys Thr Gly Thr Gly Gly Cys Thr Gly Cys Ala Gly Cys Gly Thr
305                 310                 315                 320
Cys Cys Ala Ala Gly Cys Cys Ala Gly Cys Ala Gly Thr Gly Gly Ala
                325                 330                 335
Gly Ala Thr Cys Ala Ala Ala Cys Ala Gly Gly Ala Gly Gly Gly Ala
                340                 345                 350
Gly Ala Cys Ala Cys Thr Thr Thr Cys Thr Ala Cys Ala Thr Cys Ala
            355                 360                 365
Ala Ala Ala Cys Cys Thr Cys Cys Ala Cys Ala Cys Cys Gly Thr
370                 375                 380
Gly Cys Gly Cys Ala Cys Cys Ala Cys Ala Gly Ala Gly Ala Thr Thr
385                 390                 395                 400
Ala Ala Cys Thr Thr Cys Ala Ala Gly Gly Thr Thr Gly Gly Gly Gly
            405                 410                 415
Ala Gly Gly Ala Gly Thr Thr Thr Gly Ala Gly Gly Ala Gly Cys Ala
            420                 425                 430
Gly Ala Cys Thr Gly Thr Gly Gly Ala Thr Gly Gly Ala Gly Gly
            435                 440                 445
Cys Cys Cys Thr Gly Thr Ala Ala Gly Ala Gly Cys Cys Thr Gly Gly
            450                 455                 460
Thr Gly Ala Ala Ala Thr Gly Gly Gly Ala Gly Ala Gly Thr Gly Ala
465                 470                 475                 480
Gly Ala Ala Thr Ala Ala Ala Thr Gly Gly Thr Cys Thr Gly Thr
            485                 490                 495
Gly Ala Gly Cys Ala Gly Ala Ala Gly Cys Thr Cys Thr Gly Ala
            500                 505                 510
Ala Gly Gly Gly Ala Gly Ala Gly Gly Cys Cys Cys Cys Ala Ala
            515                 520                 525
Gly Ala Cys Cys Thr Cys Gly Thr Gly Ala Cys Cys Ala Gly Ala
            530                 535                 540
Gly Ala Ala Cys Thr Gly Ala Cys Cys Ala Cys Gly Ala Thr Gly
545                 550                 555                 560
Gly Gly Gly Ala Ala Cys Thr Gly Ala Thr Cys Cys Thr Gly Ala Cys
                565                 570                 575
Cys Ala Thr Gly Ala Cys Gly Gly Cys Gly Gly Ala Thr Gly Ala Cys
            580                 585                 590
Gly Thr Thr Gly Thr Gly Thr Gly Cys Ala Cys Cys Ala Gly Gly Gly
        595                 600                 605
Thr Cys Thr Ala Cys Gly Thr Cys Cys Gly Ala Gly Ala Gly Thr Gly
            610                 615                 620
```

-continued

```
Ala Gly Thr Gly Gly Cys Ala Cys Ala Gly Thr Ala Gly Ala
625                 630             635             640

Ala Cys Cys Gly Cys Gly Gly Cys Cys Gly Ala Ala Gly Cys Cys Cys
                645             650                 655

Ala Cys Cys Ala Cys Thr Gly Gly Cys Cys Ala Thr Gly Cys Thr Cys
                660             665                 670

Ala Cys Cys Gly Cys Cys Cys Thr Gly Cys Thr Thr Cys Ala Cys Thr
                675             680                 685

Gly Cys Cys Cys Cys Cys Thr Cys Cys Gly Thr Cys Cys Ala Cys
    690             695             700

Cys Cys Cys Cys Thr Cys Cys Thr Thr Cys Thr Ala Gly Gly Ala Thr
705             710             715                 720

Ala Gly Cys Gly Cys Thr Cys Cys Cys Thr Thr Ala Cys Cys Cys
                725             730                 735

Cys Ala Gly Thr Cys Ala Cys Thr Thr Cys Thr Gly Gly Gly Gly
            740             745             750

Thr Cys Ala Cys Thr Gly Gly Gly Ala Thr Gly Cys Cys Thr Cys Thr
        755             760                 765

Thr Gly Cys Ala Gly Gly Gly Thr Cys Thr Thr Gly Cys Thr Thr Thr
        770             775                 780

Cys Thr Thr Thr Gly Ala Cys Cys Thr Cys Thr Thr Cys Thr Cys Thr
785                 790             795             800

Cys Cys Thr Cys Cys Cys Cys Thr Ala Cys Cys Ala Cys Ala Ala Cys
            805             810                 815

Ala Ala Ala Gly Ala Gly Gly Ala Ala Thr Gly Gly Cys Thr Gly Cys
            820             825             830

Ala Ala Gly Ala Gly Cys Cys Cys Ala Gly Ala Thr Cys Ala Cys Cys
            835             840                 845

Cys Ala Thr Thr Cys Cys Gly Gly Gly Thr Thr Cys Ala Cys Thr Cys
        850             855             860

Cys Cys Cys Gly Cys Cys Thr Cys Cys Cys Ala Ala Gly Thr Cys
865             870             875                 880

Ala Gly Cys Ala Gly Thr Cys Cys Thr Ala Gly Cys Cys Cys Cys Ala
            885             890             895

Ala Ala Cys Cys Ala Gly Cys Cys Cys Ala Gly Ala Gly Cys Ala Gly
            900             905             910

Gly Gly Thr Cys Thr Cys Thr Cys Thr Ala Ala Gly Gly Gly Gly
        915             920             925

Ala Cys Thr Thr Gly Ala Gly Gly Gly Cys Cys Thr Gly Ala Gly Cys
            930             935             940

Ala Gly Gly Ala Ala Ala Gly Ala Cys Thr Gly Gly Cys Cys Cys Thr
945                 950             955             960

Cys Thr Ala Gly Cys Thr Thr Cys Thr Ala Cys Cys Cys Thr Thr Thr
        965             970             975

Gly Thr Cys Cys Cys Thr Gly Thr Ala Gly Cys Cys Thr Ala Thr Ala
        980             985             990

Cys Ala Gly Thr Thr Thr Ala Gly Ala Ala Thr Ala Thr Thr Thr Ala
        995             1000            1005

Thr Thr Thr Gly Thr Thr Ala Thr Thr Thr Thr Ala Thr Thr Ala
    1010            1015            1020

Ala Ala Ala Thr Gly Cys Thr Thr Thr Ala Ala Ala Ala Ala Ala
1025            1030            1035            1040

Thr Ala Ala Ala Ala Ala Ala Ala Ala Ala Ala Ala Ala Ala Ala
```

Ala Ala Ala Ala Ala Ala Ala Ala Ala Ala Ala Ala
            1045              1050              1055

Ala Ala Ala Ala Ala Ala Ala Ala Ala Ala Ala Ala
        1060              1065              1070

Ala Ala Ala
    1075

<210> SEQ ID NO 35
<211> LENGTH: 138
<212> TYPE: PRT
<213> ORGANISM: Homo sapiens

<400> SEQUENCE: 35

Met Pro Asn Phe Ser Gly Asn Trp Lys Ile Ile Arg Ser Glu Asn Phe
  1               5                  10                  15

Glu Glu Leu Leu Lys Val Leu Gly Val Asn Val Met Leu Arg Lys Ile
             20                  25                  30

Ala Val Ala Ala Ala Ser Lys Pro Ala Val Glu Ile Lys Gln Glu Gly
         35                  40                  45

Asp Thr Phe Tyr Ile Lys Thr Ser Thr Thr Val Arg Thr Thr Glu Ile
 50                  55                  60

Asn Phe Lys Val Gly Glu Glu Phe Glu Glu Gln Thr Val Asp Gly Arg
 65                  70                  75                  80

Pro Cys Lys Ser Leu Val Lys Trp Glu Ser Glu Asn Lys Met Val Cys
                 85                  90                  95

Glu Gln Lys Leu Leu Lys Gly Glu Gly Pro Lys Thr Ser Trp Thr Arg
            100                 105                 110

Glu Leu Thr Asn Asp Gly Glu Leu Ile Leu Thr Met Thr Ala Asp Asp
            115                 120                 125

Val Val Cys Thr Arg Val Tyr Val Arg Glu
        130                 135

<210> SEQ ID NO 36
<211> LENGTH: 1075
<212> TYPE: PRT
<213> ORGANISM: Homo sapiens

<400> SEQUENCE: 36

Gly Ala Thr Thr Cys Ala Ala Gly Thr Gly Thr Gly Cys Thr
  1               5                  10                  15

Thr Thr Gly Cys Gly Thr Cys Cys Gly Cys Thr Thr Cys Cys Cys
             20                  25                  30

Ala Thr Cys Cys Ala Cys Thr Thr Ala Cys Thr Ala Gly Cys Gly Cys
         35                  40                  45

Ala Gly Gly Ala Gly Ala Ala Gly Gly Cys Thr Ala Thr Cys Thr Cys
 50                  55                  60

Gly Gly Thr Cys Cys Cys Ala Gly Ala Gly Ala Ala Gly Cys Cys
 65                  70                  75                  80

Thr Gly Gly Ala Cys Cys Ala Cys Ala Cys Gly Cys Gly Gly Gly
                 85                  90                  95

Cys Thr Ala Gly Ala Thr Cys Cys Ala Gly Ala Ala Cys Cys
            100                 105                 110

Thr Gly Ala Cys Gly Ala Cys Cys Gly Gly Cys Gly Ala Cys Gly
            115                 120                 125

Gly Cys Gly Ala Cys Gly Thr Cys Thr Cys Thr Thr Thr Gly Ala
        130                 135                 140

Cys Thr Ala Ala Ala Ala Gly Ala Cys Ala Gly Thr Gly Thr Cys Cys

```
         145                 150                 155                 160
Ala Gly Thr Gly Cys Thr Cys Cys Ala Gly Cys Cys Thr Ala Gly Gly
                 165                 170                 175
Ala Gly Thr Cys Thr Ala Cys Gly Gly Gly Ala Cys Cys Gly Cys
         180                 185                 190
Cys Thr Cys Cys Cys Gly Cys Gly Cys Cys Gly Cys Cys Ala Cys Cys
                 195                 200                 205
Ala Thr Gly Cys Cys Cys Ala Ala Cys Thr Thr Cys Thr Cys Thr Gly
         210                 215                 220
Gly Cys Ala Ala Cys Thr Gly Gly Ala Ala Ala Thr Cys Ala Thr
225                 230                 235                 240
Cys Cys Gly Ala Thr Cys Gly Gly Ala Ala Ala Cys Thr Thr Cys
                 245                 250                 255
Gly Ala Gly Gly Ala Ala Thr Thr Gly Cys Thr Cys Ala Ala Ala Gly
                 260                 265                 270
Thr Gly Cys Thr Gly Gly Gly Gly Thr Gly Ala Ala Thr Gly Thr
         275                 280                 285
Gly Ala Thr Gly Cys Thr Gly Ala Gly Gly Ala Ala Gly Ala Thr Thr
         290                 295                 300
Gly Cys Thr Gly Thr Gly Gly Cys Thr Gly Cys Ala Gly Cys Gly Thr
305                 310                 315                 320
Cys Cys Ala Ala Gly Cys Cys Ala Gly Cys Ala Gly Thr Gly Gly Ala
                 325                 330                 335
Gly Ala Thr Cys Ala Ala Ala Cys Ala Gly Gly Ala Gly Gly Gly Ala
                 340                 345                 350
Gly Ala Cys Ala Cys Thr Thr Thr Cys Thr Ala Cys Ala Thr Cys Ala
                 355                 360                 365
Ala Ala Ala Cys Cys Thr Cys Cys Ala Cys Cys Ala Cys Cys Gly Thr
         370                 375                 380
Gly Cys Gly Cys Ala Cys Cys Ala Cys Ala Gly Ala Gly Ala Thr Thr
385                 390                 395                 400
Ala Ala Cys Thr Thr Cys Ala Ala Gly Gly Thr Thr Gly Gly Gly Gly
                 405                 410                 415
Ala Gly Gly Ala Gly Thr Thr Thr Gly Ala Gly Gly Ala Gly Cys Ala
                 420                 425                 430
Gly Ala Cys Thr Gly Thr Gly Gly Ala Thr Gly Gly Ala Gly Gly
         435                 440                 445
Cys Cys Cys Thr Gly Thr Ala Ala Gly Ala Gly Cys Cys Thr Gly Gly
         450                 455                 460
Thr Gly Ala Ala Ala Thr Gly Gly Gly Ala Gly Ala Gly Thr Gly Ala
465                 470                 475                 480
Gly Ala Ala Thr Ala Ala Ala Ala Thr Gly Gly Thr Cys Thr Gly Thr
                 485                 490                 495
Gly Ala Gly Cys Ala Gly Ala Ala Gly Cys Thr Cys Cys Thr Gly Ala
                 500                 505                 510
Ala Gly Gly Gly Ala Gly Ala Gly Gly Cys Cys Cys Ala Ala
                 515                 520                 525
Gly Ala Cys Cys Thr Cys Gly Thr Gly Gly Ala Cys Cys Ala Gly Ala
         530                 535                 540
Gly Ala Ala Cys Thr Gly Ala Cys Cys Ala Cys Gly Ala Thr Gly
545                 550                 555                 560
Gly Gly Gly Ala Ala Cys Thr Gly Ala Thr Cys Cys Thr Gly Ala Cys
                 565                 570                 575
```

-continued

```
Cys Ala Thr Gly Ala Cys Gly Gly Cys Gly Ala Thr Gly Ala Cys
                580                 585                 590
Gly Thr Thr Gly Thr Gly Thr Gly Cys Ala Cys Cys Ala Gly Gly Gly
            595                 600                 605
Thr Cys Thr Ala Cys Gly Thr Cys Cys Gly Ala Gly Ala Gly Thr Gly
            610                 615                 620
Ala Gly Thr Gly Gly Cys Cys Ala Cys Ala Gly Gly Thr Ala Gly Ala
625                 630                 635                 640
Ala Cys Cys Gly Cys Gly Gly Cys Cys Gly Ala Ala Gly Cys Cys Cys
                645                 650                 655
Ala Cys Cys Ala Cys Thr Gly Gly Cys Cys Ala Thr Gly Cys Thr Cys
                660                 665                 670
Ala Cys Cys Gly Cys Cys Cys Thr Gly Cys Thr Thr Cys Ala Cys Thr
                675                 680                 685
Gly Cys Cys Cys Cys Cys Thr Cys Cys Gly Thr Cys Cys Cys Ala Cys
            690                 695                 700
Cys Cys Cys Cys Thr Cys Thr Thr Cys Thr Ala Gly Gly Ala Cys Thr
705                 710                 715                 720
Ala Gly Cys Gly Cys Thr Cys Cys Cys Cys Thr Thr Ala Cys Cys Cys
                725                 730                 735
Cys Ala Gly Thr Cys Ala Cys Thr Thr Cys Thr Gly Gly Gly Gly Gly
                740                 745                 750
Thr Cys Ala Cys Thr Gly Gly Gly Ala Thr Gly Cys Cys Thr Cys Thr
            755                 760                 765
Thr Gly Cys Ala Gly Gly Gly Thr Cys Thr Thr Thr Gly Cys Thr Thr Thr
        770                 775                 780
Cys Thr Thr Thr Gly Ala Cys Cys Thr Cys Thr Thr Cys Thr Cys Thr
785                 790                 795                 800
Cys Cys Thr Cys Cys Cys Thr Ala Cys Ala Cys Cys Ala Ala Cys
                805                 810                 815
Ala Ala Ala Gly Ala Gly Gly Ala Ala Thr Gly Gly Cys Thr Gly Cys
                820                 825                 830
Ala Ala Gly Ala Gly Cys Cys Ala Gly Ala Thr Cys Ala Cys Cys
                835                 840                 845
Cys Ala Thr Thr Cys Cys Gly Gly Gly Thr Thr Cys Ala Cys Thr Cys
            850                 855                 860
Cys Cys Cys Gly Cys Cys Thr Cys Cys Cys Ala Ala Gly Thr Cys
865                 870                 875                 880
Ala Gly Cys Ala Gly Thr Cys Cys Thr Ala Gly Cys Cys Cys Cys Ala
                885                 890                 895
Ala Ala Cys Cys Ala Gly Cys Cys Cys Ala Gly Ala Gly Cys Ala Gly
                900                 905                 910
Gly Gly Thr Cys Thr Cys Thr Cys Thr Ala Ala Gly Gly Gly Gly
            915                 920                 925
Ala Cys Thr Thr Gly Ala Gly Gly Cys Cys Thr Gly Ala Gly Cys
                930                 935                 940
Ala Gly Gly Ala Ala Ala Gly Ala Cys Thr Gly Gly Cys Cys Cys Thr
945                 950                 955                 960
Cys Thr Ala Gly Cys Thr Thr Cys Thr Ala Cys Cys Thr Thr Thr
            965                 970                 975
Gly Thr Cys Cys Cys Thr Gly Thr Ala Gly Cys Cys Thr Ala Thr Ala
                980                 985                 990
```

```
Cys Ala Gly Thr Thr Thr Ala Gly Ala Ala Thr Thr Thr Ala
        995                 1000                1005

Thr Thr Thr Gly Thr Thr Ala Ala Thr Thr Thr Ala Thr Thr Ala
        1010                1015                1020

Ala Ala Ala Thr Gly Cys Thr Thr Ala Ala Ala Ala Ala Ala
1025                1030                1035                1040

Thr Ala Ala Ala Ala Ala Ala Ala Ala Ala Ala Ala Ala Ala
            1045                1050                1055

Ala Ala Ala Ala Ala Ala Ala Ala Ala Ala Ala Ala Ala Ala
            1060                1065                1070

Ala Ala Ala
        1075

<210> SEQ ID NO 37
<211> LENGTH: 138
<212> TYPE: PRT
<213> ORGANISM: Homo sapiens

<400> SEQUENCE: 37

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Ala Val Ala Ala Ala Ser Lys Pro Ala Val Glu Ile Lys Gln Glu Gly
        35                  40                  45

Asp Thr Phe Tyr Ile Lys Thr Ser Thr Thr Val Arg Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Arg
            100                 105                 110

Glu Leu Thr Asn Asp Gly Glu Leu Ile Leu Thr Met Thr Ala Asp Asp
        115                 120                 125

Val Val Cys Thr Arg Val Tyr Val Arg Glu
        130                 135

<210> SEQ ID NO 38
<211> LENGTH: 1088
<212> TYPE: DNA
<213> ORGANISM: Homo sapiens

<400> SEQUENCE: 38
ggagcgggag gcggggccac ttcaatcctg ggcaggggcg gttccgtaca gggtataaaa      60
gctgtccgcg cgggagccca ggccagcttt ggggttgtcc ctggacttgt cttggttcca     120
gaacctgacg acccggcgac ggcgacgtct cttttgacta aaagacagtg tccagtgctc     180
cagcctagga gtctacgggg accgcctccc gcgccgccac catgcccaac ttctctggca     240
actggaaaat catccgatcg gaaaacttcg aggaattgct caaagtgctg ggggtgaatg     300
tgatgctgag gaagattgct gtggctgcag cgtccaagcc agcagtggag atcaaacagg     360
agggagacac tttctacatc aaaacctcca ccaccgtgcg caccacagag attaacttca     420
aggttgggga ggagtttgag agcagactg tggatgggag gccctgtaag agcctggtga     480
aatgggagag tgagaataaa atggtctgtg agcagaagct cctgaaggga gagggcccca     540
```

-continued

```
agacctcgtg gaccagagaa ctgaccaacg atggggaact gatcctgacc atgacggcgg    600
atgacgttgt gtgcaccagg gtctacgtcc gagagtgagt ggccacaggt agaaccgcgg    660
ccgaagccca ccactggcca tgctcaccgc cctgcttcac tgcccccctcc gtcccacccc   720 ctccttctag gatagcgctc cccttacccc agtcacttct gggggtcact gggatgcctc    780
ttgcagggtc ttgctttctt tgacctcttc tctcctcccc tacaccaaca agaggaatg    840 gctgcaagag cccagatcac ccattccggg ttcactcccc gcctcccaa gtcagcagtc    900 ctagccccaa accagcccag agcagggtct ctctaaaggg gacttgaggg cctgagcagg    960
aaagactggc cctctagctt ctacccttttg tccctgtagc ctatacagtt tagaatattt   1020
atttgttaat tttattaaaa tgctttaaaa aaataaaaaa aaaaaaaaaa aaaaaaaaaa   1080
aaaaaaaa                                                            1088
```

<210> SEQ ID NO 39
<211> LENGTH: 133
<212> TYPE: PRT
<213> ORGANISM: Artificial Sequence
<220> FEATURE:
<223> OTHER INFORMATION: A synthetic peptide

<400> SEQUENCE: 39

```
Thr Arg Asp Gln Asn Gly Thr Trp Glu Met Glu Ser Asn Glu Asn Phe
 1               5                  10                  15

Glu Gly Tyr Met Lys Ala Leu Asp Ile Asp Phe Ala Thr Arg Lys Ile
            20                  25                  30

Ala Val Arg Leu Thr Gln Thr Leu Val Ile Asp Gln Asp Gly Asp Asn
        35                  40                  45

Phe Lys Val Lys Thr Thr Ser Thr Phe Phe Asn Tyr Asp Val Asp Phe
    50                  55                  60

Thr Val Gly Val Glu Phe Asp Glu Tyr Thr Lys Ser Leu Asp Asn Arg
65                  70                  75                  80

His Val Lys Ala Leu Val Thr Trp Glu Gly Asp Val Leu Val Cys Val
                85                  90                  95

Gln Lys Gly Glu Lys Glu Asn Arg Gly Trp Lys Lys Trp Ile Glu Gly
            100                 105                 110

Asp Lys Leu Tyr Leu Glu Leu Thr Cys Gly Asp Gln Val Cys Arg Gln
        115                 120                 125

Val Phe Lys Lys Lys
    130
```

<210> SEQ ID NO 40
<211> LENGTH: 134
<212> TYPE: PRT
<213> ORGANISM: Artificial Sequence
<220> FEATURE:
<223> OTHER INFORMATION: A synthetic peptide

<400> SEQUENCE: 40

```
Met Thr Arg Asp Gln Asn Gly Thr Trp Glu Met Glu Ser Asn Glu Asn
 1               5                  10                  15

Phe Glu Gly Tyr Met Lys Ala Leu Asp Ile Asp Phe Ala Thr Arg Lys
            20                  25                  30

Ile Ala Val Arg Leu Thr Gln Thr Leu Val Ile Asp Gln Asp Gly Asp
        35                  40                  45

Asn Phe Lys Val Lys Thr Thr Ser Thr Phe Phe Asn Tyr Asp Val Asp
    50                  55                  60
```

Phe Thr Val Gly Val Glu Phe Asp Glu Tyr Thr Lys Ser Leu Asp Asn
65                  70                  75                  80

Arg His Val Lys Ala Leu Val Thr Trp Glu Gly Asp Val Leu Val Cys
                85                  90                  95

Val Gln Lys Gly Glu Lys Glu Asn Arg Gly Trp Lys Lys Trp Ile Glu
            100                 105                 110

Gly Asp Lys Leu Tyr Leu Glu Leu Thr Cys Gly Asp Gln Val Cys Arg
            115                 120                 125

Gln Val Phe Lys Lys Lys
            130

<210> SEQ ID NO 41
<211> LENGTH: 138
<212> TYPE: PRT
<213> ORGANISM: Artificial Sequence
<220> FEATURE:
<223> OTHER INFORMATION: A synthetic peptide

<400> SEQUENCE: 41

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Trp Val Ala Ala Ser Lys Pro Ala Val Glu Ile Lys Gln Glu Gly Gly
        35                  40                  45

Asp Thr Phe Tyr Ile Lys Val Ser Thr Thr Val Trp Thr Thr Glu Ile
    50                  55                  60

Asn Phe Lys Val Gly Glu Glu Phe Glu Ala Gln Thr Val Asp Gly Arg
65                  70                  75                  80

Pro Cys Lys Ser Leu Val Lys Trp Glu Ser Glu Asn Lys Leu Val Cys
                85                  90                  95

Glu Gln Lys Leu Leu Lys Gly Glu Gly Pro Lys Thr Ser Trp Thr Lys
            100                 105                 110

Glu Leu Thr Asn Asp Gly Glu Leu Ile Leu Thr Met Thr Ala Asp Asp
            115                 120                 125

Val Val Cys Thr Gln Val Phe Val Arg Glu
            130                 135

<210> SEQ ID NO 42
<211> LENGTH: 137
<212> TYPE: PRT
<213> ORGANISM: Artificial Sequence
<220> FEATURE:
<223> OTHER INFORMATION: A synthetic peptide

<400> SEQUENCE: 42

Pro Asn Phe Ser Gly Asn Trp Lys Ile Ile Arg Ser Glu Asn Phe Glu
1               5                   10                  15

Glu Leu Leu Lys Val Leu Gly Val Asn Val Met Leu Arg Lys Ile Trp
            20                  25                  30

Val Ala Ala Ser Lys Pro Ala Val Glu Ile Lys Gln Glu Gly Asp
        35                  40                  45

Thr Phe Tyr Ile Lys Val Ser Thr Thr Val Trp Thr Thr Glu Ile Asn
    50                  55                  60

Phe Lys Val Gly Glu Glu Phe Glu Ala Gln Thr Val Asp Gly Arg Pro
65                  70                  75                  80

Cys Lys Ser Leu Val Lys Trp Glu Ser Glu Asn Lys Leu Val Cys Glu
                85                  90                  95

```
Gln Lys Leu Leu Lys Gly Glu Gly Pro Lys Thr Ser Trp Thr Lys Glu
            100                 105                 110

Leu Thr Asn Asp Gly Glu Leu Ile Leu Thr Met Thr Ala Asp Asp Val
        115                 120                 125

Val Cys Thr Gln Val Phe Val Arg Glu
    130                 135

<210> SEQ ID NO 43
<211> LENGTH: 138
<212> TYPE: PRT
<213> ORGANISM: Artificial Sequence
<220> FEATURE:
<223> OTHER INFORMATION: A synthetic peptide

<400> SEQUENCE: 43

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Trp Val Ala Ala Ser Lys Pro Ala Val Glu Ile Lys Gln Glu Gly
        35                  40                  45

Asp Thr Phe Tyr Ile Lys Val Ser Thr Thr Val Trp Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Lys
            100                 105                 110

Glu Leu Thr Asn Asp Gly Glu Leu Ile Leu Thr Met Thr Ala Asp Asp
        115                 120                 125

Val Val Cys Thr Leu Val Phe Val Arg Glu
    130                 135

<210> SEQ ID NO 44
<211> LENGTH: 138
<212> TYPE: PRT
<213> ORGANISM: Artificial Sequence
<220> FEATURE:
<223> OTHER INFORMATION: A synthetic peptide

<400> SEQUENCE: 44

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Trp Val Ala Ala Ser Lys Pro Ala Val Glu Ile Lys Gln Glu Gly
        35                  40                  45

Asp Thr Phe Tyr Ile Lys Val Ser Thr Thr Val Tyr Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Lys
            100                 105                 110

Glu Leu Thr Asn Asp Gly Glu Leu Ile Leu Thr Met Thr Ala Asp Asp
```

```
                    115                 120                 125

Val Val Cys Thr Leu Val Phe Val Arg Glu
    130                 135

<210> SEQ ID NO 45
<211> LENGTH: 138
<212> TYPE: PRT
<213> ORGANISM: Artificial Sequence
<220> FEATURE:
<223> OTHER INFORMATION: A synthetic peptide

<400> SEQUENCE: 45

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Ala Val Ala Ala Ala Ser Lys Pro Ala Val Glu Ile Lys Gln Glu Gly
        35                  40                  45

Asp Thr Phe Tyr Ile Lys Thr Ser Thr Thr Val Arg Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Lys
            100                 105                 110

Glu Leu Thr Asn Asp Gly Glu Leu Ile Leu Thr Met Thr Ala Asp Asp
        115                 120                 125

Val Val Cys Thr Leu Val Phe Val Arg Glu
    130                 135

<210> SEQ ID NO 46
<211> LENGTH: 138
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 4, 10, 13, 16, 20, 25, 33, 36-40, 46, 55, 57-60, 62, 74,
      75, 77, 79, 82, 94, 96, 122, 124, 131, 133, 135
<223> OTHER INFORMATION: Xaa = any amino acid

<400> SEQUENCE: 46

Met Pro Asn Xaa Ser Gly Asn Trp Lys Xaa Ile Arg Xaa Glu Asn Xaa
1               5                   10                  15

Glu Glu Leu Xaa Lys Val Leu Gly Xaa Asn Val Met Leu Arg Lys Ile
            20                  25                  30

Xaa Val Ala Xaa Xaa Xaa Xaa Xaa Ala Val Glu Ile Lys Xaa Glu Gly
        35                  40                  45

Asp Thr Phe Tyr Ile Lys Xaa Ser Xaa Xaa Xaa Thr Xaa Glu Ile
    50                  55                  60

Asn Phe Lys Val Gly Glu Glu Phe Glu Xaa Xaa Thr Xaa Asp Xaa Arg
65                  70                  75                  80

Pro Xaa Lys Ser Leu Val Lys Trp Glu Ser Glu Asn Lys Xaa Val Xaa
                85                  90                  95

Glu Gln Lys Leu Leu Lys Gly Glu Gly Pro Lys Thr Ser Trp Thr Lys
            100                 105                 110

Glu Leu Thr Asn Asp Gly Glu Leu Ile Xaa Thr Xaa Thr Ala Asp Asp
```

```
                115                 120                 125
Val Val Xaa Thr Xaa Val Xaa Val Arg Glu
        130                 135

<210> SEQ ID NO 47
<211> LENGTH: 133
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 2, 4, 16, 19, 20, 25, 29, 33, 38, 40, 42, 51, 53, 55,
      57, 58, 60, 62, 64, 72, 76, 77, 95, 97, 104, 106, 108, 117, 119,
      128, 130
<223> OTHER INFORMATION: Xaa = any amino acid

<400> SEQUENCE: 47

Thr Xaa Asp Xaa Asn Gly Thr Trp Glu Met Glu Ser Asn Glu Asn Xaa
 1               5                  10                  15

Glu Gly Xaa Xaa Lys Ala Leu Asp Xaa Asp Phe Ala Xaa Arg Lys Ile
            20                  25                  30

Xaa Val Arg Leu Thr Xaa Thr Xaa Val Xaa Asp Gln Asp Gly Asp Asn
            35                  40                  45

Phe Lys Xaa Lys Xaa Thr Xaa Thr Xaa Xaa Asn Xaa Asp Xaa Asp Xaa
 50                  55                  60

Thr Val Gly Val Glu Phe Asp Xaa Tyr Thr Lys Xaa Xaa Asp Asn Arg
 65                  70                  75                  80

His Val Lys Ala Leu Val Thr Trp Glu Gly Asp Val Leu Val Xaa Val
             85                  90                  95

Xaa Lys Gly Glu Lys Glu Asn Xaa Gly Xaa Lys Xaa Trp Ile Glu Gly
            100                 105                 110

Asp Lys Leu Tyr Xaa Glu Xaa Thr Cys Gly Asp Gln Val Cys Arg Xaa
            115                 120                 125

Val Xaa Lys Lys Lys
        130
```

COLORIMETRIC AND FLUORESCENT PROTEINS

This application is a Continuation of U.S. patent application Ser. No. 13/636,499, filed Mar. 7, 2013, which was a National Stage filing of Patent Cooperation Treaty serial number PCT/US2011/029616, filed Mar. 23, 2011, which claims benefit of the priority filing date of U.S. Provisional Application Ser. No. 61/340,831, filed Mar. 23, 2010, the contents of which are specifically incorporated herein by reference in their entirety.

GOVERNMENT SUPPORT

This invention was made with government support under R01 GM067311 awarded by the National Institutes of Health. The government has certain rights in the invention.

BACKGROUND OF THE INVENTION

The complex functions of biological molecules are difficult to ascertain, in part because it is difficult to observe these molecules within functioning biological systems. Thus, the locus of a biomolecule's activity and the factors that actually interact with the biomolecule may not be apparent because it is difficult to distinguish one biomolecule from another within a living cell or tissue.

Labeled antibodies have been employed to identify specific factors within cells and tissues. But antibodies are large molecules that do not readily penetrate cells and binding of antibodies can often inhibit or modulate the functioning of the molecule to which it is bound.

Dyes have also been used to 'color' different cells and cellular factors. But researchers may not be able to distinguish one biomolecule from another, or trace the activity and functioning of a particular biomolecule, when using dyes because those dyes generally color many cellular structures and/or interrupt the functioning of the cells and/or biomolecules of interest.

Labeled antibodies and dyes also fail to provide sufficient signal strength to permit real-time observation of biomolecule activity. For example, while green fluorescent protein (GFP) has been used to observe the location of particular biomolecules within cells and/or tissues, GFP can require several hours to manifest fluorescence. Hence, the movements and interactions of GFP-linked biomolecules cannot be adequately traced in dynamic in vivo systems. Moreover, GFP cannot be used to observe several factors or biomolecules at once because GFP emits only one fluorescence color (green) and cannot be used to distinguish one biomolecule from another. GFP also requires oxygen, which is either not available or not plentiful in many cell types.

Therefore, new tools are needed that will permit real-time visualization of multiple biomolecules and factors at once.

SUMMARY OF THE INVENTION

The invention relates to modified proteins in the intracellular lipid binding protein (iLBP) family that are characterized by large hydrophobic internal binding cavities and that specifically bind a variety of ligands as protonated Schiff bases with high affinity. These iLBP proteins have been modified such that the absorbance and light transmission of a chromophore ligand (e.g., a retinoid or dye) can be modulated across the visual range and into the near infrared range. These proteins are remarkably stable and can be recombinantly generated and expressed as fusion proteins.

One aspect of the invention is an isolated nucleic acid encoding a modified polypeptide that is a member of the intracellular lipid binding protein (iLBP) family, wherein the modified polypeptide transmits or emits light when bound to a retinoid or fluorescent dye molecule, and wherein the intracellular lipid binding protein has been modified so that an amino acid at any of positions 102-135 can form a Schiff base with a retinoid (e.g., retinal). In some embodiments, the retinoid or a fluorescent dye binds specifically to the modified iLBP protein and forms a Schiff base upon binding. For example, such an isolated nucleic acid can encode a modified polypeptide that has been modified by replacement of the amino acid at any of positions 102-135 with a lysine. Such a Schiff base-forming iLBP polypeptide can be further modified to include amino acid substitutions at a variety of positions to modulate the light transmission/emission properties of the modified polypeptide:retinoid/dye complex. In fact, as illustrated herein, by a variety of amino acid substitutions can be made to yield iLBP polypeptides that transmit or emit light over the entire visible spectrum of light.

In some embodiments, the isolated nucleic acid encodes a modified polypeptide that has been modified by replacement of a glutamine at any of amino acid positions 107, 108 or 109 with a lysine. In other embodiments, the isolated nucleic acid encodes a modified polypeptide that has been modified by replacement of an arginine at any of amino acid positions 110, 111 or 112 with a lysine. In further embodiments, the isolated nucleic acid can encode a modified polypeptide that has been modified by replacement of an arginine at any of amino acid positions 131, 132 or 133 with a lysine. In another embodiment, the isolated nucleic can encode a modified intracellular lipid binding protein that is modified by replacement of a lysine at any of amino acid positions 39, 40 or 41 with a leucine, serine or asparagine. In other embodiments, the isolated nucleic acid can encode a modified intracellular lipid binding protein that is modified by replacement of an arginine at any of amino acid positions 131, 132 or 133 with a glutamine. In further embodiments, the isolated nucleic acid can encode a modified intracellular lipid binding protein that is modified by replacement of a threonine at any of amino acid positions 50, 51, 52, 53, 54 or 55 with an aspartic acid, asparagine, cysteine or a valine. In another embodiment, the isolated nucleic acid can encode a modified intracellular lipid binding protein that is modified by replacement of a tyrosine at any of amino acid positions 59, 60 or 61 with a tryptophan, histidine, threonine, asparagine or phenylalanine. In other embodiments, the isolated nucleic acid can encode a modified intracellular lipid binding protein that is modified by replacement of an arginine at any of amino acid positions 57, 58, 59 or 60 with a phenylalanine, tyrosine, tryptophan, leucine, glutamine, glutamic acid, aspartic acid or alanine. In a further embodiment, the isolated nucleic acid can encode a modified intracellular lipid binding protein that is modified by replacement of a tyrosine at any of amino acid positions 133, 134 or 135 with a phenylalanine. In another embodiment, the isolated nucleic acid can encode a modified intracellular lipid binding protein that is modified by replacement of a threonine at any of amino acid positions 28, 29 or 30 with a leucine, tryptophan, glutamic acid or aspartic acid. In a further embodiment, the isolated nucleic acid can encode a modified intracellular lipid binding protein that is modified by replacement of an alanine at any of amino acid positions 30, 31, 32 or 33 with a tryptophan, phenylalanine, tyrosine, serine, histidine, glutamic acid or leucine. In other embodiments, the isolated nucleic acid can encode a modified intracellular lipid binding protein that is modified by replacement of a tyrosine at any of amino acid positions 18, 19 or 20 with a tryptophan or phenylalanine. In further embodiments, the isolated nucleic acid can encode a modified intracellular lipid binding protein that is modified by replacement of a glutamine at any of amino acid positions 3, 4 or 5 with an arginine, asparagine, phenylalanine, leucine, alanine, tryptophan, threonine, glutamic acid, histidine, or lysine. In another embodiment, the isolated nucleic acid can encode a modified intracellular lipid binding protein that is modified by replacement of a methionine at any of amino acid positions 92, 93 or 94 with a leucine. In other embodiments, the isolated nucleic acid can encode a modified intracellular lipid binding protein that is modified by replacement of a glutamic acid at any of amino acid positions 72, 73 or 74 with an alanine or leucine. In other embodiments, the isolated nucleic acid can encode a modified intracellular lipid binding protein that is modified by replacement of a glutamine at any of amino acid positions 36, 37 or 38 with a leucine, methionine or tryptophan. In other embodiments, the isolated nucleic acid can encode a modified intracellular lipid binding protein that is modified by replacement of a glutamine at any of amino acid positions 128, 129 or 130 with n leucine, lysine, glutamic acid or tryptophan.

In some embodiments, the isolated nucleic acid encodes a modified intracellular lipid binding protein that is a modified cellular retinoic acid binding protein II (CRABPII) or a modified cellular retinol binding protein II (CRBPII).

Another aspect of the invention is a modified intracellular lipid binding protein (iLBP) that transmits or emits light when bound to a retinoid or fluorescent dye molecule, wherein the intracellular lipid binding protein has been modified so that an amino acid at any of positions 102-135 can form a Schiff base with a retinoid. Such a modified iLBP polypeptide can be modified by replacement of the amino acid at any of positions 102-135 with a lysine. In some embodiments, the modified intracellular lipid binding protein is a modified cellular retinoic acid binding protein II (CRABPII) or a modified cellular retinol binding protein II (CRBPII).

The modified iLBP polypeptide can be modified by replacement of a glutamine at any of amino acid positions 107, 108 or 109 with a lysine. In other embodiments, the modified iLBP polypeptide can be modified by replacement of an arginine at any of amino acid positions 110, 111 or 112 with a lysine. In further embodiments, the modified iLBP polypeptide can be modified by replacement of an arginine at any of amino acid positions 131, 132 or 133 with a lysine. In another embodiment, the modified iLBP polypeptide can be modified by replacement of a lysine at any of amino acid positions 39, 40 or 41 with a leucine, serine or asparagine. In other embodiments, the modified iLBP polypeptide can be modified by replacement of an arginine at any of amino acid positions 131, 132 or 133 with a glutamine. In further embodiments, the modified iLBP polypeptide can be modified by replacement of a threonine at any of amino acid positions 50, 51, 52, 53, 54 or 55 with an aspartic acid, asparagine, cysteine or a valine. In another embodiment, the modified iLBP polypeptide can be modified by replacement of a tyrosine at any of amino acid positions 59, 60 or 61 with a tryptophan, histidine, threonine, asparagine or phenylalanine. In other embodiments, the modified iLBP polypeptide can be modified by replacement of an arginine at any of amino acid positions 57, 58, 59 or 60 with a phenylalanine, tyrosine, tryptophan, leucine, glutamine, glutamic acid, aspartic acid or alanine. In a further embodiment, the modified iLBP polypeptide can be modified by replacement of a tyrosine at any of amino acid positions 133, 134 or 135 with a phenylalanine. In another embodiment, the modified iLBP polypeptide can be modified by replacement of a threonine at any of amino acid positions 28, 29 or 30 with a leucine, tryptophan, glutamic acid or aspartic acid. In a further embodiment, the modified iLBP polypeptide can be modified by replacement of an alanine at any of amino acid positions 30, 31, 32 or 33 with a tryptophan, phenylalanine, tyrosine, serine, histidine, glutamic acid or leucine. In other embodiments, the modified iLBP polypeptide can be modified by replacement of a tyrosine at any of amino acid positions 18, 19 or 20 with a tryptophan or phenylalanine. In further embodiments, the modified iLBP polypeptide can be modified by replacement of a glutamine at any of amino acid positions 3, 4 or 5 with an arginine, asparagine, phenylalanine, leucine, alanine, tryptophan, threonine, glutamic acid, histidine, or lysine. In another embodiment, the modified iLBP polypeptide can be modified by replacement of a methionine at any of amino acid positions 92, 93 or 94 with a leucine. In other embodiments, the modified iLBP polypeptide can be modified by replacement of a glutamic acid at any of amino acid positions 72, 73 or 74 with an alanine or leucine. In other embodiments, the modified iLBP polypeptide can be modified by replacement of a glutamine at any of amino acid positions 36, 37 or 38 with a leucine, methionine or tryptophan. In other embodiments, the modified iLBP polypeptide can be modified by replacement of a glutamine at any of amino acid positions 128, 129 or 130 with a leucine, lysine, glutamic acid or tryptophan.

In some embodiments, the modified polypeptide comprises an amino acid sequence selected from the group consisting of SEQ ID NO:6-28, 39-47, or a combination thereof.

Another aspect of the invention is a hybrid nucleic acid comprising an isolated (modified) iLBP nucleic acid joined to a fusion partner nucleic acid that encodes a fusion partner polypeptide. In such a hybrid nucleic acid, the isolated (modified) iLBP nucleic acid can be joined in frame to the fusion partner nucleic acid.

Another aspect of the invention is a fusion protein comprising a modified iLBP of the invention joined to a fusion partner polypeptide. In such a fusion protein, the modified iLBP of the invention can be joined in frame to the fusion partner.

Another aspect of the invention is an expression cassette comprising an isolated (modified) iLBP nucleic acid of the invention and at least one nucleic acid segment encoding a regulatory element.

Another aspect of the invention is a vector comprising an isolated (modified) iLBP nucleic acid of the invention. In some embodiments, the vector comprised an expression cassette comprising an isolated (modified) iLBP nucleic acid of the invention and at least one nucleic acid segment encoding a regulatory element.

Another aspect of the invention is a host cell comprising an isolated (modified) iLBP nucleic acid of the invention and at least one nucleic acid segment encoding a regulatory element. In some embodiments, the isolated nucleic acid within the host cell is within an expression cassette, a vector or a combination thereof.

Another aspect of the invention is a method of observing a target protein in vivo comprising contacting a living cell with a retinoid or dye that binds a modified polypeptide encoded by the isolated nucleic acid of claim 1, wherein the cell expresses a fusion protein comprising the modified polypeptide fused in frame with the target protein.

DESCRIPTION OF THE FIGURES

FIG. 1B shows various CRBPII modified polypeptides bound to retinal that were loaded onto an anion-exchange column. This figure illustrates that the modified CRBPII polypeptides described herein can be used as a colorimetric tag for protein purification.

FIG. 3A shows wild type cells treated with merocyanine dye ligand (no CRBP protein is present in these cells). FIG. 3B shows *E. coli* cells expressing wild-type human CRBPII, which does not bind the fluorescent ligand. Although the merocyanine dye was added to the cells, it does not form a complex with the wild-type CRBP and no fluorescence is observed. FIG. 3C shows *E. coli* cells expressing modified human CRBPII treated with merocyanine dye ligand. The modified human CRBPII polypeptide binds the merocyanine dye and fluorescence within the cells is clearly visible.

FIG. 4A-C illustrates the in vivo fluorescence of modified CRBP fusion proteins in the presence of a merocyanine dye ligand. FIG. 4A is a schematic diagram of the fusion proteins used to conduct the experiments in FIGS. 4B and 4C, respectively. FIG. 4B shows confocal micrographs of human osteosarcoma cells transfected with pEGFP-CRBP vector, where the merocyanine dye was added. As shown, the GFP-CRBP fusion product is expressed and fluorescence is detected throughout the cell from both the GFP (left panel: Excitation with blue light) and the CRBP segment (middle panel: excitation with 594 nm light). The right panel shows and overlay of green and red and bright-field pictures, further illustrating that the GFP and CRBP fluorescence co-localizes. FIG. 4C shows confocal micrograph of human osteosarcoma cells transfected with pEGFP-CRBP-RB vector, where the merocyanine dye was also present. RB (retinoblastoma protein) directs the protein complex of GFP-CRBP-RB to the nucleus. Thus, the GFP-CRBP-RB fusion product is expressed and localized in the nucleus as shown in FIG. 4C. Fluorescence is detected in the nucleus of the cell from both the GFP (left panel: Excitation with blue light) and the CRBP polypeptide segments (middle panel: excitation with 594 nm). The right panel shows and overlay of green and red and bright-field pictures, further illustrating that the GFP and CRBP fluorescence co-localizes. Note also that while the merocyanine dye is likely present throughout the cell, the fluorescent signal is observed only within the cell nuclei, indicating that binding between the CRBP polypeptide and the dye is needed to generate a signal.

FIG. 5A shows absorption spectra taken over a wide range of pH conditions. FIG. 5B shows a titration curve made from the data provided in FIG. 5A, illustrating that light absorption varies with pH. As shown, the smallest absorption corresponds to the highest pH and the lowest absorption corresponds to the lowest pH. FIG. 5C shows fluorescence spectra of a mutant CRABPII/merocyanine dye complex at pH 7.3 (the highest emission) and at pH 8.6 (the lowest emission), the structure of the associated pH sensitive merocyanine dye upon formation of the Schiff base with the protein is shown below.

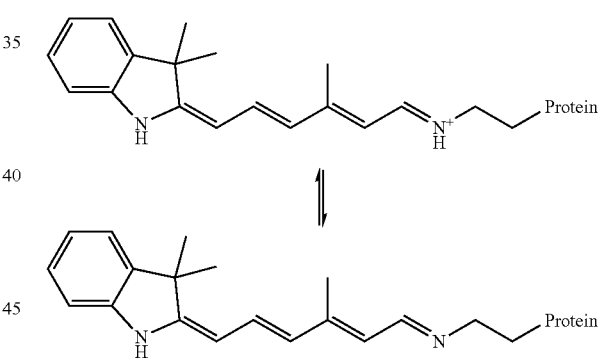

Figure 6B:
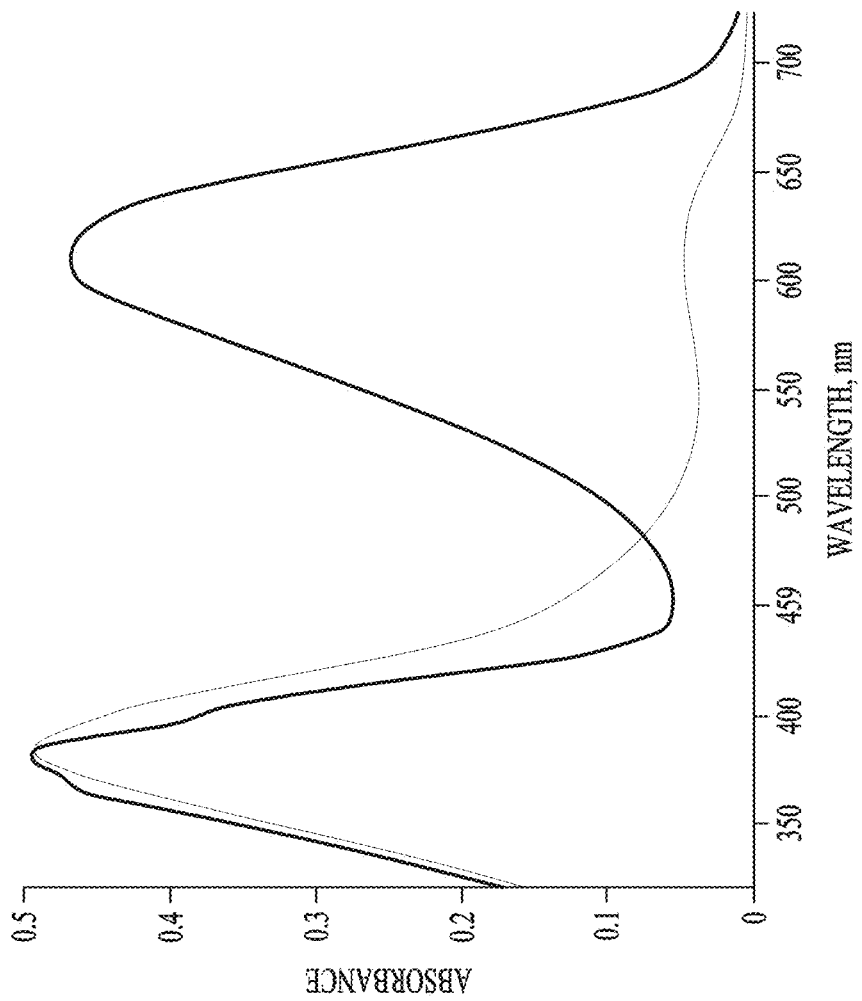
Figure 6A:
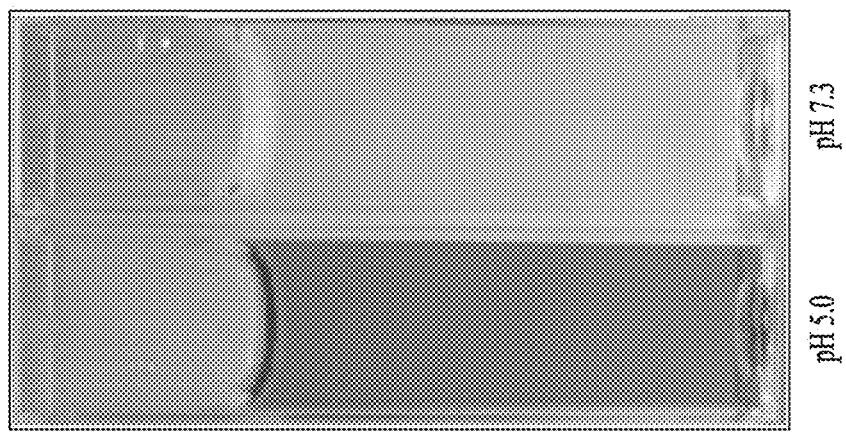
Figure 6D:
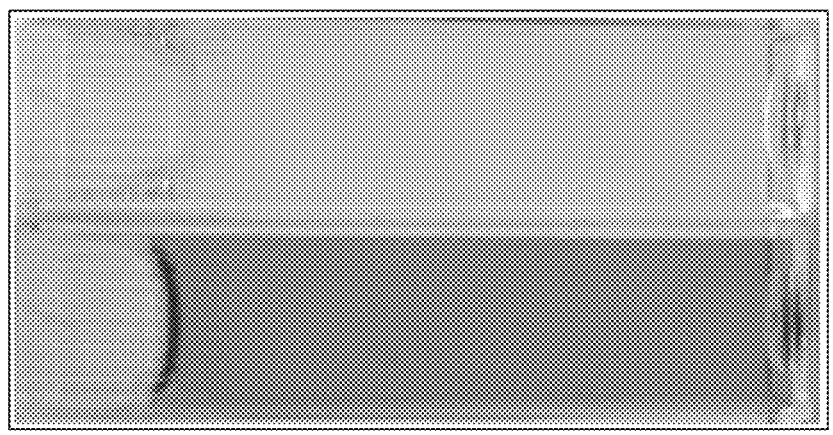
Figure 6C:
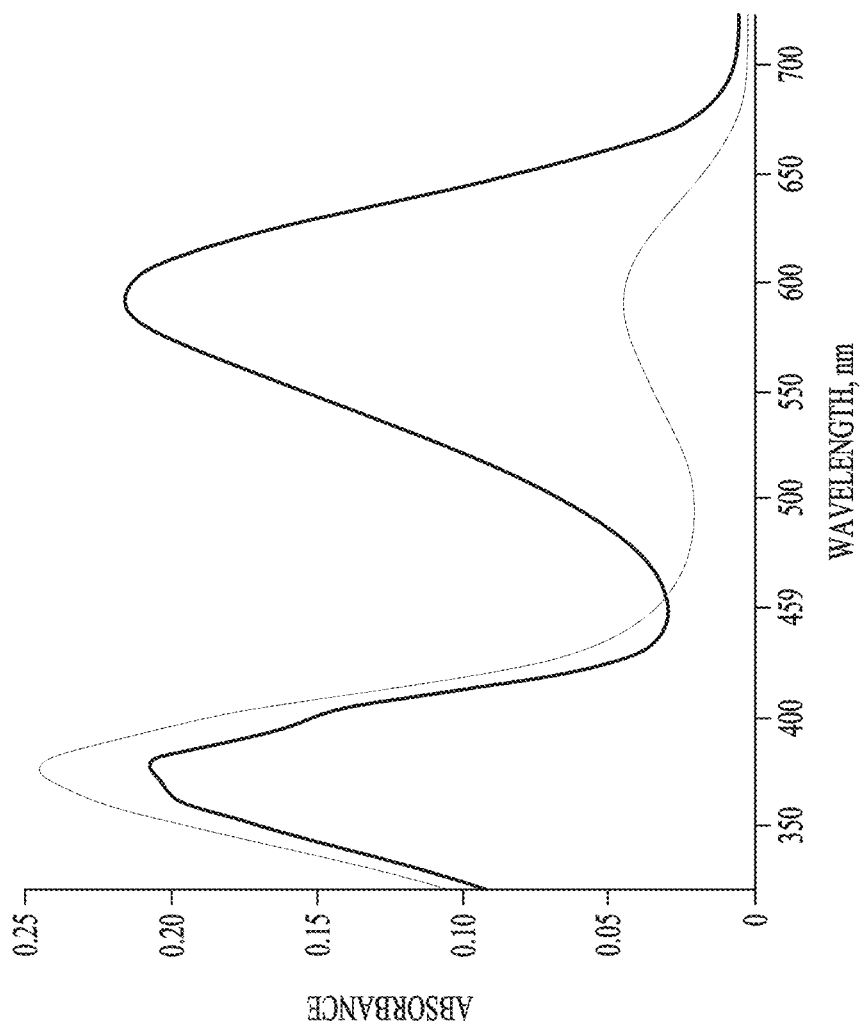

FIG. 6A-D illustrates the light absorption and transmission properties of two modified CRABPII polypeptides in the presence of retinal at pH 5.0 and pH 7.3. FIG. 6A shows that the first modified CRABPII polypeptide (SEQ ID NO:43) has a darker color (blue when seen in color) at pH 5.0 and a lighter color (pale yellow when seen in color) at pH 7.3. FIG. 6B shows the absorption spectrum of this first modified CRABPII polypeptide (SEQ ID NO:43). Note that the first modified CRABPII polypeptide has two strong absorption maxima at pH 5.0, one at about 400 nm and the other at about 610 nm. However, the absorption at about 610 nm of this first CRABPII polypeptide is greatly reduced at pH 7.3. FIG. 6C shows the absorption spectrum of a second modified CRABPII polypeptide (SEQ ID NO:44), which also has two strong absorption maxima at pH 5.0, one at about 375 nm and the other at about 600 nm. However, the absorption at about 600 nm of this second modified CRABPII polypeptide (SEQ ID NO:44) is greatly reduced at pH 7.3. FIG. 6D shows that the second modified CRABPII polypeptide (SEQ ID NO:44) has a darker color (purple when seen in color) at pH 5.0 and a lighter color (pale orange when seen in color) at pH 7.3. Thus, these modified CRABPII polypeptides are colorimetric protein-based pH sensors capable of changing their light absorption and transmission properties in response to pH changes over a range of pH conditions spanning at least pH 5.0-7.5.

Figure 7A:
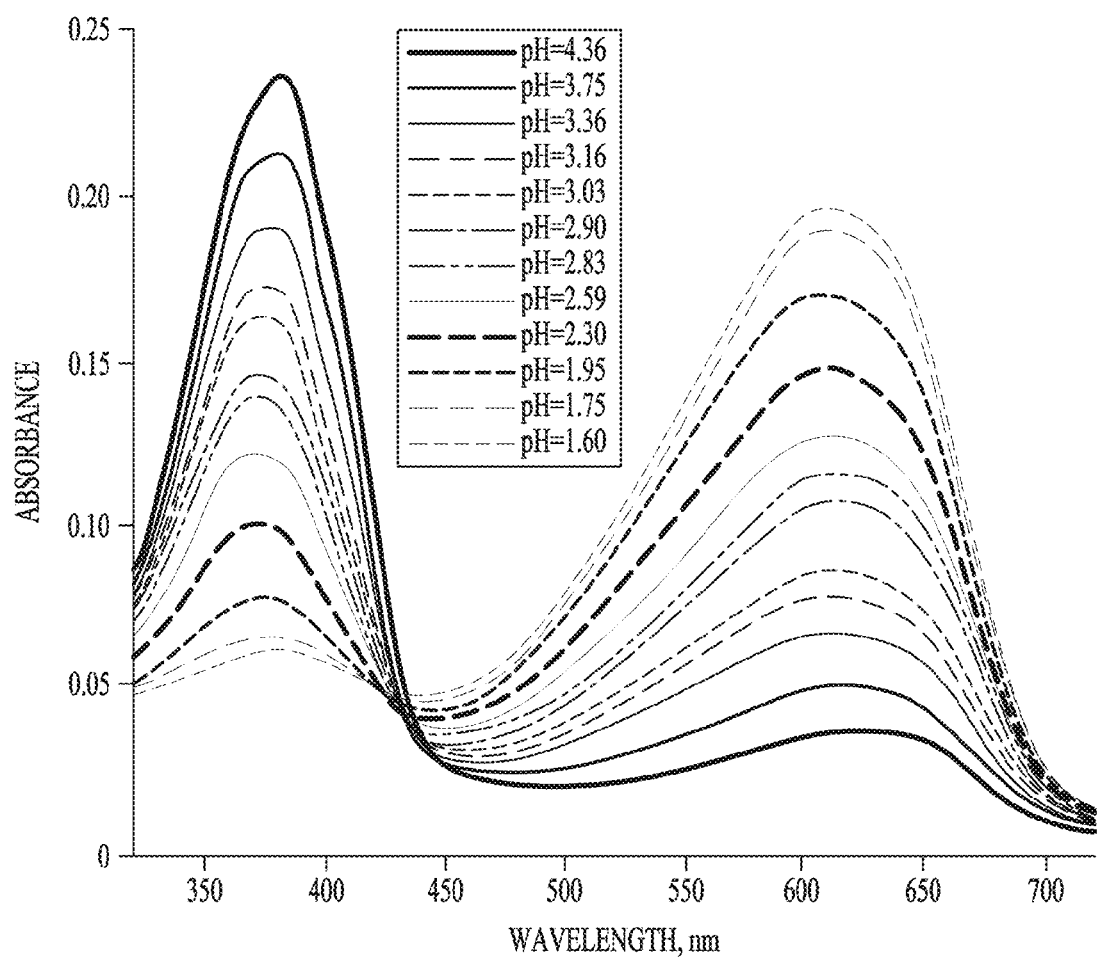
Figure 7B:
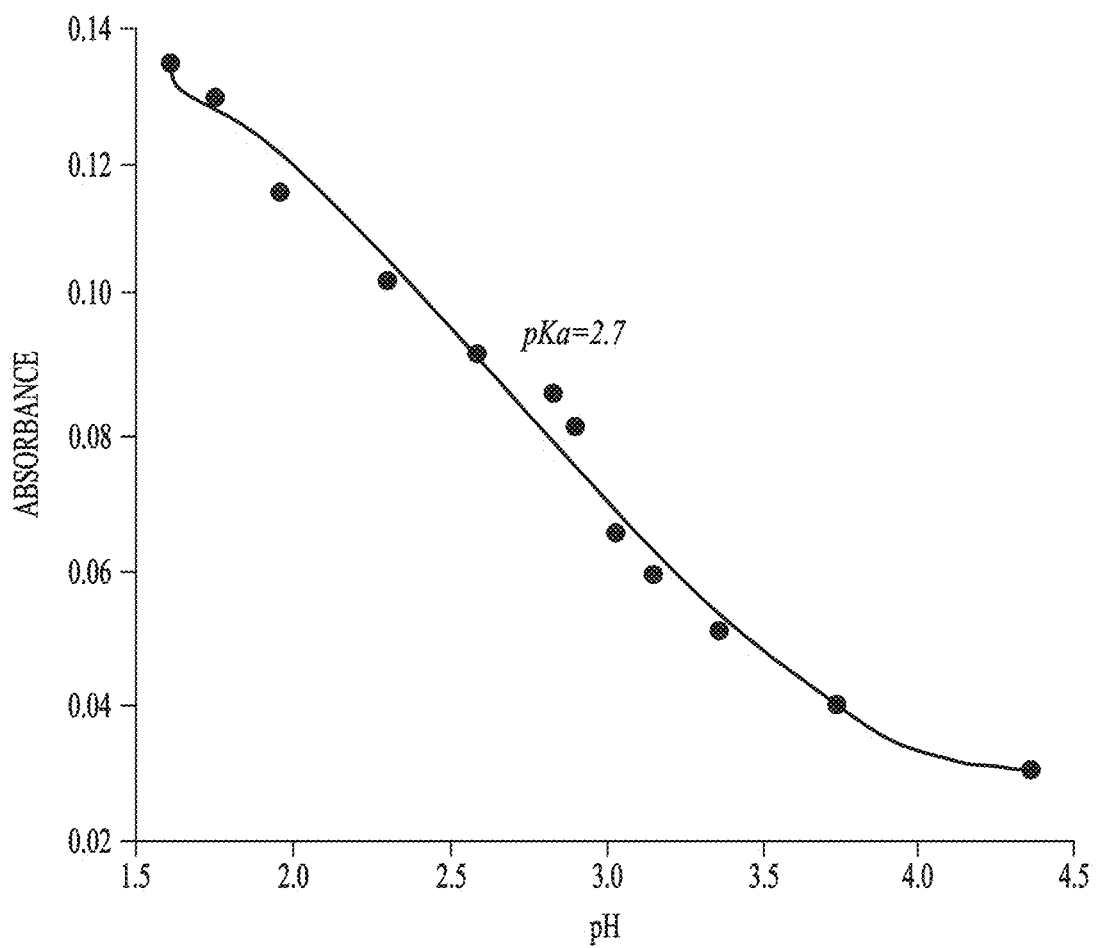

FIGS. 7A and B shows that modified CRABPII polypeptides are remarkably stable to acid. The absorption of a selected modified CRABPII polypeptide (SEQ ID NO:42) under various pH conditions in the presence of retinal was measured. FIG. 7A shows that the polypeptide retains secondary and tertiary structures contributing to the unique light absorption properties of the polypeptide over a wide range of pH values. Thus, the polypeptide exhibits extraordinary stability towards acidification down to pH 1.6. FIG. 7B graphically illustrates the shift in maximal wavelength of absorption with pH for this modified CRABPII polypeptide (SEQ ID NO:42).

Figure 8:
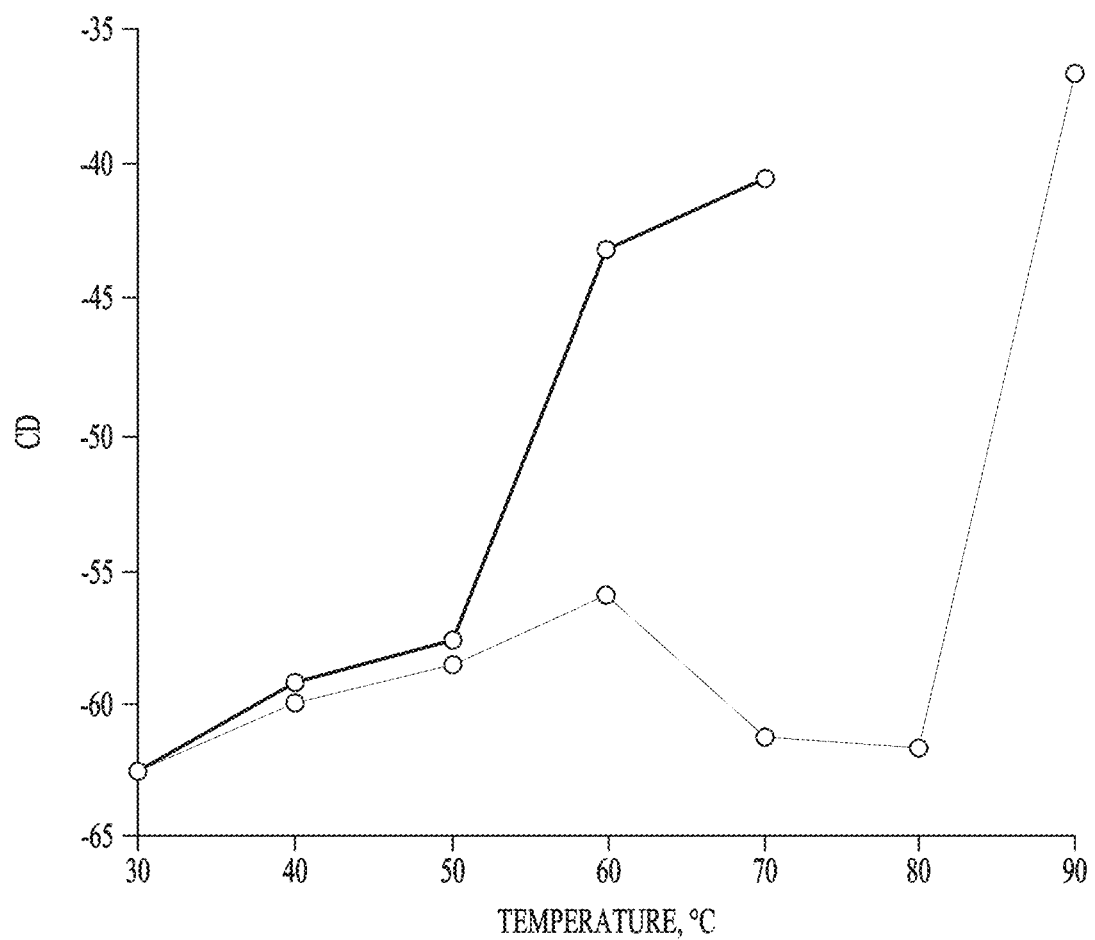

FIG. 8 shows that modified CRABPII polypeptides are remarkably stable to temperature. The CD spectrum shows that while a CRABPII polypeptide with SEQ ID NO:45 unfolds at around 50° C., the modified CRABPII polypeptide with SEQ ID NO:42 is stable up to 80° C. Increasing values along the y-axis represent increased disorder in the secondary and/or tertiary structures of the polypeptides. Thus, the modified CRABPII polypeptides described herein can be stabilized by introduction of specific amino acid changes (e.g., selected from those in the modified CRABPII polypeptide with SEQ ID NO:42).

DETAILED DESCRIPTION OF THE INVENTION

The invention described herein relates to intracellular lipid binding proteins (iLBPs) that are modified to absorb, emit, fluoresce and/or transmit light in a variety of wavelengths when bound to a retinoid or fluorescent dye, and nucleic acids encoding such modified iLBPs. Such modified iLBPs are useful colorimetric and/or fluorescent labeling agents that can be fused to other molecules of interest. For example, the modified iLBPs of the invention can be used to label target biomolecules in vivo to permit observation and analysis of the biomolecules' location, interactions and activities. Because the colorimetric/fluorescent iLBP proteins of the invention are readily modified to emit light at different wavelengths, several target biomolecules can be monitored at once by employing different colorimetric/fluorescent proteins.

In general, according to the invention, the wavelength of light transmitted or emitted depends upon the polarity of the iLBP pocket that binds a retinoid or other dye ligand. Thus, for example, increased negative polarity in the pocket near a ring moiety of the retinoid or dye ligand and/or decreased negative polarity in the region of a Schiff base formed between the iLBP and the dye ligand yields an iLBP:ligand complex that transmits light with a longer (more red) wavelength. Conversely, the light transmitted by an iLBP:ligand complex is more blue-shifted (shorter wavelength) when the Schiff base region has more negative polarity and the ring of the retinoid/dye ligand has decreased negative polarity. The inventors have modulated the sequences of iLBP proteins to generate modified iLBP polypeptides that transmit or emit light at a variety of wavelengths.

Intracellular Lipid Binding Proteins and Nucleic Acids

According to the invention, intracellular lipid binding proteins (iLBPs) can be modified to form fluorescent and colorimetric labeling agents that absorb and transmit light at diverse wavelengths when bound to a retinoid or fluorescent dye ligand. As illustrated herein, a wild type intracellular lipid binding protein typically does not transmit significant light, especially when the wild type iLBP does not bind a retinoid or fluorescent dye ligand via a Schiff base.

iLBPs are low molecular mass proteins (14-16 kDa) that generally have a common structural fold. The iLBP family likely arose through duplication and diversification of an ancestral iLBP gene. Members of the family of intracellular lipid binding proteins (iLBPs) can facilitate cytoplasmic transport of lipophilic ligands, such as long-chain fatty acids and retinoids. Thus, iLBPs naturally form a complex with long-chain fatty acids and retinoids. However, wild type iLBPs typically do not form a Schiff base linkage to the associated long-chain fatty acid or retinoid molecule.

As illustrated herein, when an iLBP does bind a retinoid or dye ligand via Schiff base formation, a stable iLBP:ligand complex forms that transmits or emits light. By modulating the polarity of the retinoid/dye ligand binding pocket through substitution of one or more iLBP amino acids, the wavelength as which the iLBP:ligand complex transmits or emits light can also be modulated.

Examples of iLBP proteins that can be used to generate colorimetric/fluorescent protein:ligand complexes include the cellular retinoic acid binding protein II (CRABPII), cellular retinol binding protein II (CRBPII), liver-type fatty acid binding protein (L-FABP), the intestinal fatty acid binding protein (I-FABP), and the ileal lipid binding protein (ilbp). In some embodiments, the iLBP selected for generating a fluorescent and colorimetric protein:ligand complex is a Cellular Retinoic Acid Binding Protein II (CRABPII) and/or Cellular Retinol Binding Protein II (CRBPII).

As used herein, a colorimetric and/or fluorescent protein or labeling agent is a member of the intracellular lipid binding protein (iLBP) family that has a modified amino acid sequence thereby generating what is referred to as a modified iLBP polypeptide. Such a modified iLBP polypeptide can transmit or emit light when bound to a retinoid or fluorescent dye molecule. In some embodiments, the iLBP polypeptide has been modified so that an amino acid at any of positions 102-135 can form a Schiff base with a retinoid (e.g., retinal) or a fluorescent dye ligand. Also in some embodiments, the iLBP family member is CRABPII or CRBPII, which is modified to generate a colorimetric and/or fluorescent protein or labeling agent (also referred to as a modified iLBP polypeptide).

Examples of amino acid and nucleic acid sequences for different types and species of iLBPs, including CRABPII and CRBPII polypeptides can be found in the art, for example, in the National Center for Biotechnology Information (NCBI) database. See website at ncbi.nlm.nih.gov. The amino acid sequences for various iLBPs can have a methionine at the N-terminus. However, as is known to one of skill in the art, the methionine can be removed by post-translational processing, particularly in eukaryotic cells. Therefore, in some embodiments the N-terminal methionine is removed or is not present on the polypeptide sequences described and claimed herein.

One sequence for a wild type human cellular retinol binding protein II (hCRBPII) polypeptide is provided by the NCBI database as accession number P50120.3 (GI: 62297500), which is readily used as a basis for generating iLBP fluorescent and colorimetric labeling agents. The sequence for this P50120.3 (GI: 62297500) polypeptide is provided below for easy reference as SEQ ID NO:1.

```
  1 MTRDQNGTWE MESNENFEGY MKALDIDFAT RKIAVRLTQT

41 KVIDQDGDNF KTKTTSTFRN YDVDFTVGVE FDEYTKSLDN

81 RHVKALVTWE GDVLVCVQKG EKENRGWKQW IEGDKLYLEL

121 TCGDQVCRQV FKKK
```

A nucleic acid sequence for this wild type human cellular retinol binding protein II polypeptide is available in the NCBI database as accession number NM_004164.2 (GI: 40354213). This sequence is provided below for easy reference as SEQ ID NO:2.

```
  1 CCTGCTCCTT GCCATCCACC ACAAACCCTC ACCGAACCAG

41 TGGCCACCAC CATGACAAGG GACCAGAATG GAACCTGGGA

81 GATGGAGAGT AATGAAAACT TTGAGGGCTA CATGAAGGCC

121 CTGGATATTG ATTTTGCCAC CCGCAAGATT GCAGTACGTC

161 TCACTCAGAC GAAGGTTATT GATCAAGATG GTGATAACTT

201 CAAGACAAAA ACCACTAGCA CATTCCGCAA CTATGATGTG

241 GATTTCACTG TTGGAGTAGA GTTTGACGAG TACACAAAGA

281 GCCTGGATAA CCGGCATGTT AAGGCACTGG TCACCTGGGA

321 AGGTGATGTC CTTGTGTGTG TGCAAAAGGG GGAGAAGGAG

361 AACCGCGGCT GGAAGCAGTG GATTGAGGGG GACAAGCTGT

401 ACCTGGAGCT GACCTGTGGT GACCAGGTGT GCCGTCAAGT

441 GTTCAAAAAG AAATGATGGC GACGTGGGAG GCCTGCCAAG

481 CACAAGCTCC CCACTGCCCA CACTGAGTGG TCTACTGGCT

521 TTGAGAAACA GCTGTGGGGA CCTTCCCACT CTTGACAGAG

561 CCCCATTAAG GCATCTGGGT GGGTTTTAAA CAGAATGCCT

601 ATGTAGCAGT GATAGACATA TTCCCCTCCT TTGAAACCTA

641 GCATTAAATG GAAAAACAAA AATTACTCCC ATATTTTGAA

681 ACCCTTTAAA AAAAAAAAA
```

This wild type hCRBPII nucleic acid, as well as other wild type iLBP nucleic acids, are useful for making modified nucleic acids that encode modified iLBP polypeptides with useful light absorption and transmission properties. Thus, a selected wild type iLBP nucleic acid can be modified by procedures available to those of skill in the art to encode modified iLBP polypeptides. Recombinant expression of the encoded modified iLBPs not only yields useful quantities of colorimetric/fluorescent iLBP polypeptides but also can be used for in vivo analysis of biological processes and biological products, as described in more detail below.

Other CRBPII sequences in addition to the SEQ ID NO:1 sequence can be used as a basis for generating modified iLBPs that are useful as fluorescent and colorimetric labeling agents. Thus, another human CRBPII polypeptide sequence that is available in the NCBI database as accession number AAC50162.1 (GI: 535390). This sequence is provided below for easy reference as SEQ ID NO:3.

```
  1 MTRDQNGTWE MESNENFEGY MKALDIDFAT PKIAVRLTQT

41 KVIDQDGDNF KTKTTSTFRN YDVDFTVGVE FDEYTKSLDN

81 RHVKALVTWE GDVLVCVQKG EKENRGWKQW IEGDKLYLEL

121 TCGDQVCRQV FKKK
```

A nucleic acid sequence for this human cellular retinol binding protein II polypeptide is available in the NCBI database as accession number NM_004164.2 (GI: 40354213). This sequence is provided below for easy reference as SEQ ID NO:4.

```
  1 CCTGCTCCTT GCCATCCACC ACAAACCCTC ACCGAACCAG

41 TGGCCACCAC CATGACAAGG GACCAGAATG GAACCTGGGA

81 GATGGAGAGT AATGAAAACT TTGAGGGCTA CATGAAGGCC

121 CTGGATATTG ATTTTGCCAC CCGCAAGATT GCAGTACGTC

161 TCACTCAGAC GAAGGTTATT GATCAAGATG GTGATAACTT

201 CAAGACAAAA ACCACTAGCA CATTCCGCAA CTATGATGTG

241 GATTTCACTG TTGGAGTAGA GTTTGACGAG TACACAAAGA

281 GCCTGGATAA CCGGCATGTT AAGGCACTGG TCACCTGGGA

321 AGGTGATGTC CTTGTGTGTG TGCAAAAGGG GGAGAAGGAG

361 AACCGCGGCT GGAAGCAGTG GATTGAGGGG GACAAGCTGT

401 ACCTGGAGCT GACCTGTGGT GACCAGGTGT GCCGTCAAGT

441 GTTCAAAAAG AAATGATGGC GACGTGGGAG GCCTGCCAAG

481 CACAAGCTCC CCACTGCCCA CACTGAGTGG TCTACTGGCT

521 TTGAGAAACA GCTGTGGGGA CCTTCCCACT CTTGACAGAG

561 CCCCATTAAG GCATCTGGGT GGGTTTTAAA CAGAATGCCT

601 ATGTAGCAGT GATAGACATA TTCCCCTCCT TTGAAACCTA

641 GCATTAAATG GAAAAACAAA AATTACTCCC ATATTTTGAA

681 ACCCTTTAAA AAAAAAAAA
```

In some cases the modified polypeptides of the invention have a methionine at their N-terminus, but in other cases the methionine is not present. For example, when the methionine is removed from the N-terminus of the SEQ ID NO:1 hCRBPII polypeptide, this polypeptide has the following sequence (SEQ ID NO:5).

```
  1 TRDQNGTWEM ESNENFEGYM KALDIDFATR KIAVRLTQTK

41 VIDQDGDNFK TKTTSTFRNY DVDFTVGVEF DEYTKSLDNR

81 HVKALVTWEG DVLVCVQKGE KENRGWKQWI EGDKLYLELT

121 CGDQVCRQVF KKK
```

As illustrated herein, the light absorption and transmission properties of such an hCRBPII polypeptide can be modulated by modulating the sequence of hCRBPII polypeptide. This can be done by procedures available in the art, for example, by recombinant manipulation or site-directed mutagenesis of a nucleic acid encoding the hCRBPII. Thus, for example, when a glutamine (Q) amino acid at about positions 107-109 (preferably position 108) is replaced with a lysine (K) amino acid, a modified hCRBPII polypeptide is generated with somewhat different physical and chemical properties, in addition to somewhat different light absorption/transmission properties. One example of such a modified CRBPII polypeptide is called a Q108K hCRBPII polypeptide, which can have the following sequence (SEQ ID NO: 6).

```
  1 TRDQNGTWEM ESNENFEGYM KALDIDFATR KIAVRLTQTK
 41 VIDQDGDNFK TKTTSTFRNY DVDFTVGVEF DEYTKSLDNR
 81 HVKALVTWEG DVLVCVQKGE KENRGWKKWI EGDKLYLELT
121 CGDQVCRQVF KKK
```

Note that the Q108K nomenclature means that while a glutamine (Q) at about position 108 is present in the wild type protein that glutamine has been replaced by a lysine (K) in the Q108K hCRBPII polypeptide identified as SEQ ID NO:6.

Such a Q108K hCRBPII polypeptide maximally absorbs light at 506 nm and adopts a favorable three-dimensional structure for positioning the lysine at position 108 to attack the retinal aldehyde to form a protonated Schiff base. However, the folding of this protein brings a lysine residue at about position 39-41 close to the Schiff base that forms between the retinal aldehyde and the nitrogen of the lysine at position 108. This lysine at position 39-41 perturbs the $pK_a$ of the protonated Schiff base, which affects the light absorption/transmission properties of the polypeptide as well as the stability of the complex formed between retinal and the Q108K hCRBPII polypeptide. To restore the pKa a counter ion can be introduced or the lysine at position 39-41 can be replaced with a less charged amino acid.

In some embodiments, the lysine at position 39-41 is replaced with a leucine. For example, when the lysine (K) at position 40 of the Q108K hCRBPII polypeptide is replaced with a leucine (L) amino acid, a modified Q108K; K40L hCRBPII polypeptide is formed, which has the following sequence (SEQ ID NO: 7).

```
  1 TRDQNGTWEM ESNENFEGYM KALDIDFATR KIAVRLTQTL
 41 VIDQDGDNFK TKTTSTFRNY DVDFTVGVEF DEYTKSLDNR
 81 HVKALVTWEG DVLVCVQKGE KENRGWKKWI EGDKLYLELT
121 CGDQVCRQVF KKK
```

The wavelength at which the Q108K; K40L hCRBPII polypeptide in combination with retinal maximally absorbs light is 508 nm Another modified hCRBPII polypeptide with not only the Q108K substitution but also a replacement of threonine (T) with aspartic acid (D) at position 50-52 (e.g., position 51) also has useful light absorption and transmission properties. The sequence of this Q108K; T51D hCRBPII polypeptide is shown below (SEQ ID NO:8).

```
  1 TRDQNGTWEM ESNENFEGYM KALDIDFATR KIAVRLTQTK
 41 VIDQDGDNFK DKTTSTFRNY DVDFTVGVEF DEYTKSLDNR
 81 HVKALVTWEG DVLVCVQKGE KENRGWKKWI EGDKLYLELT
121 CGDQVCRQVF KKK
```

The wavelength at which the Q108K; T51D hCRBPII polypeptide in combination with retinal maximally absorbs light is 474 nm Studies indicate that the Q108K; K40L hCRBPII polypeptide is more stable than the Q108K; T51D hCRBPII polypeptide. Hence, in some embodiments Q108K; K40L hCRBPII polypeptides are used a platform for generating other modified iLBP colorimetric/fluorescent proteins.

To generate a variety of fluorescent and colorimetric labeling agents that absorb and transmit light at a variety of different wavelengths the hCRBPII polypeptide (e.g. the Q108K; K40L hCRBPII polypeptide) sequence can be altered in a variety of ways.

For example, the tyrosine at any of positions 59-61 can be changed to a tryptophan. When this is done at position 60 of the Q108K; K40L hCRBPII polypeptide, a polypeptide that maximally absorbs light at 512 nm is generated that is called the Q108K; K40L; Y60W hCRBPII polypeptide, with the following sequence (SEQ ID NO:9).

```
  1 TRDQNGTWEM ESNENFEGYM KALDIDFATR KIAVRLTQTL
 41 VIDQDGDNFK TKTTSTFRNW DVDFTVGVEF DEYTKSLDNR
 81 HVKALVTWEG DVLVCVQKGE KENRGWKKWI EGDKLYLELT
121 CGDQVCRQVF KKK
```

In another example, the threonine at any of positions 50-52 (e.g., position 51) can be replaced with a valine. For example, if the threonine (T) at position 51 of the Q108K; K40L hCRBPII polypeptide is replaced with a valine (V), the resulting Q108K; K40L; T51V hCRBPII polypeptide has the following sequence (SEQ ID NO:10).

```
  1 TRDQNGTWEM ESNENFEGYM KALDIDFATR KIAVRLTQTL
 41 VIDQDGDNFK VKTTSTFRNY DVDFTVGVEF DEYTKSLDNR
 81 HVKALVTWEG DVLVCVQKGE KENRGWKKWI EGDKLYLELT
121 CGDQVCRQVF KKK
```

The wavelength at which the Q108K; K40L; T51V hCRBPII polypeptide, in combination with retinal, maximally absorbs light is 533 nm.

A replacement of the arginine at any of positions 57-59 with another amino acid can also modulate the wavelength at which an hCRBPII polypeptide absorbs and/or transmits light. For example, if the arginine (R) at position 58 of the Q108K; K40L hCRBPII polypeptide is replaced with a phenylalanine (F), the resulting Q108K; K40L; R58F hCRBPII polypeptide maximally absorbs light at 524 nm, and has the following sequence (SEQ ID NO:11).

```
  1 TRDQNGTWEM ESNENFEGYM KALDIDFATR KIAVRLTQTL
 41 VIDQDGDNFK TKTTSTFFNY DVDFTVGVEF DEYTKSLDNR
 81 HVKALVTWEG DVLVCVQKGE KENRGWKKWI EGDKLYLELT
121 CGDQVCRQVF KKK
```

But if the arginine (R) at position 58 of the Q108K; K40L hCRBPII polypeptide is replaced with a tyrosine (Y), the resulting Q108K; K40L; R58Y hCRBPII polypeptide maximally absorbs light at 535 nm, and has the following sequence (SEQ ID NO:12).

```
  1 TRDQNGTWEM ESNENFEGYM KALDIDFATR KIAVRLTQTL
 41 VIDQDGDNFK TKTTSTFYNY DVDFTVGVEF DEYTKSLDNR
```

```
 81 HVKALVTWEG DVLVCVQKGE KENRGWKKWI EGDKLYLELT

121 CGDQVCRQVF KKK
```

Still further modulation of the light absorption and transmission properties of CRBPII polypeptides can be achieved by making several amino acid replacements at once. Thus, for example, if the arginine (R) at position 58 of a Q108K; K40L; T51V hCRBPII polypeptide is replaced with a tyrosine (Y) the resulting Q108K; K40L; T51V; R58Y hCRBPII polypeptide maximally absorbs light is 563 nm as opposed to 533 nm for the Q108K; K40L; T51V hCRBPII or at 524 nm for the Q108K; K40L; R58F hCRBPII polypeptide. The sequence of the Q108K; K40L; T51V; R58Y hCRBPII polypeptide is as follows (SEQ ID NO:13).

```
  1 TRDQNGTWEM ESNENFEGYM KALDIDFATR KIAVRLTQTL

41 VIDQDGDNFK VKTTSTFYNY DVDFTVGVEF DEYTKSLDNR

81 HVKALVTWEG DVLVCVQKGE KENRGWKKWI EGDKLYLELT

121 CGDQVCRQVF KKK
```

Changing the arginine (R) at position 58 of a Q108K; K40L; T51V hCRBPII polypeptide to a tryptophan (W) results in a Q108K; K40L; T51V; R58W hCRBPII polypeptide with the following sequence (SEQ ID NO:14).

```
  1 TRDQNGTWEM ESNENFEGYM KALDIDFATR KIAVRLTQTL

41 VIDQDGDNFK VKTTSTFWNY DVDFTVGVEF DEYTKSLDNR

81 HVKALVTWEG DVLVCVQKGE KENRGWKKWI EGDKLYLELT

121 CGDQVCRQVF KKK
```

The light absorption and transmission properties of CRBPII polypeptides can also be modulated by replacement of a threonine at any of positions 52-54. For example, replacement of the threonine at position 53 of the Q108K; K40L; T51V; R58W hCRBPII polypeptide yields a polypeptide that maximally absorbs light at 585 nm that is referred as the Q108K; K40L; T51V; R58W; T53C hCRBPII polypeptide, which has the following sequence (SEQ ID NO:15).

```
  1 TRDQNGTWEM ESNENFEGYM KALDIDFATR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Replacement of a threonine at any of positions 28-30 with another amino acid also modulates the light absorption and transmission properties. For example, replacing a threonine (T) at position 29 of the Q108K; K40L; T51V; R58W; T53C hCRBPII polypeptide with a leucine, yields a polypeptide with the following sequence (SEQ ID NO:16), that is referred to as the Q108K; K40L; T51V; R58W; T53C; T29L hCRBPII polypeptide.

```
  1 TRDQNGTWEM ESNENFEGYM KALDIDFALR KIAVRLTQTL

41 VIDQDGDNFK VKCTSTFWNY DVDFTVGVEF DEYTKSLDNR
```

```
 81 HVKALVTWEG DVLVCVQKGE KENRGWKKWI EGDKLYLELT

121 CGDQVCRQVF KKK
```

Replacement of a tyrosine at any of positions 18-20 can also modulate the light absorption and transmission properties. For example, when a tyrosine at position 19 of the Q108K; K40L; T51V; R58W; T53C; T29L hCRBPII polypeptide is replaced with a tryptophan, a polypeptide with a light absorption maximum of 591 is generated, which is referred to as the Q108K; K40L; T51V; R58W; T53C; T29L; Y19W hCRBPII polypeptide. This polypeptide has the following sequence (SEQ ID NO:17).

```
  1 TRDQNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Replacement of a glutamine (Q) amino acid at any of positions 3-5 can also modulate the light absorption and transmission properties. For example, when a glutamine at position 4 of the Q108K; K40L; T51V; R58W; T53C; T29L; Y19W hCRBPII polypeptide is changed to a arginine (R), a polypeptide with a light absorption maximum of 622 nm is generated, which is referred to as the Q108K; K40L; T51V; R58W; T53C; T29L; Y19W; Q4R hCRBPII polypeptide. This polypeptide has the following sequence (SEQ ID NO:18).

```
  1 TRDRNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

The following table summarizes the light absorption/transmission properties of various CRBPII polypeptides that are complexed with retinal.

TABLE 1

Maximum Absorption Wavelength, Kd/nM and pKa Values for Modified CRBPII polypeptides

| Modified CRBPII | $\lambda_{max}$ (nm) | $K_d$/nM | $pK_a$ |
|---|---|---|---|
| Q108K | 506 | 48 ± 4 | <6.0 |
| Q108K; T51D | 474 | 67 ± 6 | 9.2 |
| Q108K; K40L | 508 | 29 ± 5 | 7.9 |
| Q108K; K40L; Y60W | 512 | 4 ± 8 | 7.1 |
| Q108K; K40L; T51V | 533 | 19 ± 7 | 8.3 |
| Q108K; K40L; R58F | 524 | 27 ± 6 | 8.6 |
| Q108K; K40L; R58Y | 535 | 10 ± 7 | 9.5 |
| Q108K; K40L; T51V; R58Y | 563 | 40 ± 5 | 10.1 |
| Q108K; K40L; T51V; R58Y; Y19W | 565 | 47 ± 5 | 10.3 |
| Q108K; K40L; T51V; R58W; T53C; T29L; Y19W | 591 | 38 ± 10 | 8.2 |
| Q108K; K40L; T51V; R58W; T53C; T29L; Y19W; Q4R | 622 | 183 ± 11 | 6.5 |

As illustrated by the data in Table 1, a large increase in the pKa value of the CRBPII polypeptide is observed when the arginine at any of positions 57-59 is replaced with another amino acid (e.g., at position 58, R58Y), even though the amino acid at position 58 is distant from the locus of Schiff base formation.

Moreover, the type of amino acid selected for replacement alters the light absorption and transmission properties of the polypeptide:retinoid complex. For example, when a variety of different amino acids are used instead of a glutamine at any of positions 3-5, the resulting CRBPII polypeptide absorbs/transmits light at a variety of different wavelengths.

As indicated above, when the glutamine at position 4 of the Q108K; K40L; T51V; R58W; T53C; T29L; Y19W hCRBPII polypeptide is changed to an arginine (R) a polypeptide with a light absorption maximum of 622 nm is generated, which is referred to as the Q108K; K40L; T51V; R58W; T53C; T29L; Y19W; Q4R hCRBPII polypeptide. This polypeptide has the following sequence (SEQ ID NO:19).

```
  1 TRDRNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

However, when the glutamine at position 4 of the Q108K; K40L; T51V; R58W; T53C; T29L; Y19W hCRBPII polypeptide is changed to an tryptophan (W) a polypeptide with a light absorption maximum of 613 nm is generated, which is referred to as the Q108K; K40L; T51V; R58W; T53C; T29L; Y19W; Q4W hCRBPII polypeptide. This polypeptide has the following sequence (SEQ ID NO:20).

```
  1 TRDWNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

When the glutamine at position 4 of the Q108K; K40L; T51V; R58W; T53C; T29L; Y19W hCRBPII polypeptide is changed to an asparagine (N) a polypeptide with the same light absorption maximum of 613 nm is generated, which is referred to as the Q108K; K40L; T51V; R58W; T53C; T29L; Y19W; Q4N hCRBPII polypeptide. This polypeptide has the following sequence (SEQ ID NO:21).

```
  1 TRDNNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Use of a threonine (T) at the position of the glutamine at position 4 of the Q108K; K40L; T51V; R58W; T53C; T29L; Y19W hCRBPII polypeptide yields a polypeptide with a light absorption maximum of 610 nm, which is referred to as the Q108K; K40L; T51V; R58W; T53C; T29L; Y19W; Q4T hCRBPII polypeptide. This polypeptide has the following sequence (SEQ ID NO:22).

```
  1 TRDTNGTWEM ESNENFEGWM KALDIDFALR KIAVRLTQTL

41 VIDQDGDNFK VKCTSTFWNY DVDFTVGVEF DEYTKSLDNR
```

-continued
```
 81 HVKALVTWEG DVLVCVQKGE KENRGWKKWI EGDKLYLELT

121 CGDQVCRQVF KKK
```

Use of a glutamic acid (E) at the position of the glutamine at position 4 of the Q108K; K40L; T51V; R58W; T53C; T29L; Y19W hCRBPII polypeptide yields a polypeptide with a light absorption maximum of 590 nm, which is referred to as the Q108K; K40L; T51V; R58W; T53C; T29L; Y19W; Q4E hCRBPII polypeptide. This polypeptide has the following sequence (SEQ ID NO:23).

```
  1 TRDENGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Use of a histidine (H) at the position of the glutamine at position 4 of the Q108K; K40L; T51V; R58W; T53C; T29L; Y19W hCRBPII polypeptide yields a polypeptide with a light absorption maximum of 585 nm, which is referred to as the Q108K; K40L; T51V; R58W; T53C; T29L; Y19W; Q4H hCRBPII polypeptide. This polypeptide has the following sequence (SEQ ID NO:24).

```
  1 TRDHNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Use of a lysine (K) at the position of the glutamine at position 4 of the Q108K; K40L; T51V; R58W; T53C; T29L; Y19W hCRBPII polypeptide yields a polypeptide with a light absorption maximum of 616 nm, which is referred to as the Q108K; K40L; T51V; R58W; T53C; T29L; Y19W; Q4K hCRBPII polypeptide. This polypeptide has the following sequence (SEQ ID NO:25).

```
  1 TRDKNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Use of a lysine (K) at the position of the glutamine at position 4 of the Q108K; K40L; T51V; R58W; T53C; T29L; Y19W hCRBPII polypeptide yields a polypeptide with a light absorption maximum of 614 nm, which is referred to as the Q108K; K40L; T51V; R58W; T53C; T29L; Y19W; Q4L hCRBPII polypeptide. This polypeptide has the following sequence (SEQ ID NO:26).

```
  1 TRDLNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

Use of a phenylalanine (F) at the position of the glutamine at position 4 of the Q108K; K40L; T51V; R58W; T53C;

T29L; Y19W hCRBPII polypeptide yields a polypeptide with a light absorption maximum of 613 nm, which is referred to as the Q108K; K40L; T51V; R58W; T53C; T29L; Y19W; Q4F hCRBPII polypeptide. This polypeptide has the following sequence (SEQ ID NO:27).

```
  1 TRDFNGTWEM ESNENFEGWM KALDIDFALR KIAVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQVF KKK
```

The following table summarizes the light absorption/transmission properties of various Q108K; K40L; T51V; R58W; T53C; T29L; Y19W CRBPII polypeptides where the glutamine at position 4 is replaced with a variety of different amino acids and the resulting polypeptide is complexed with retinal.

TABLE 2

Maximum Absorption Wavelength, Kd/nM and pKa Values for Q108K; K40L; T51V; R58W; T53C; T29L; Y19W; Q4 CRBPII polypeptides

| Modified CRBPII | $\lambda_{max}$ (nm) | $K_d$/nM | $pK_a$ |
|---|---|---|---|
| Q108K; K40L; T51V; R58W; T53C; T29L; Y19W; Q4 (no replacement of the glutamine at position 4) | 591 | 38 ± 10 | 8.2 |
| Q108K; K40L; T51V; R58W; T53C; T29L; Y19W; Q4W | 613 | 103 ± 10 | 7.7 |
| Q108K; K40L; T51V; R58W; T53C; T29L; Y19W; Q4F | 614 | 57 ± 8 | 7.9 |
| Q108K; K40L; T51V; R58W; T53C; T29L; Y19W; Q4L | 613 | 58 ± 12 | 7.5 |
| Q108K; K40L; T51V; R58W; T53C; T29L; Y19W; Q4N | 613 | 65 ± 12 | 7.2 |
| Q108K; K40L; T51V; R58W; T53C; T29L; Y19W; Q4T | 610 | 63 ± 8 | 7.8 |
| Q108K; K40L; T51V; R58W; T53C; T29L; Y19W; Q4E | 590 | 162 ± 20 | ND |
| Q108K; K40L; T51V; R58W; T53C; T29L; Y19W; Q4H | 585 | 18 ± 5 | 7.9 |
| Q108K; K40L; T51V; R58W; T53C; T29L; Y19W; Q4K | 616 | 12 ± 8 | 7.2 |
| Q108K; K40L; T51V; R58W; T53C; T29L; Y19W; Q4R | 622 | 183 ± 11 | 6.5 |

Thus, modulating not only the position of the amino acid replacement, but also the type of amino acid placed in a position modulates the light absorption and transmission properties of a CRBPII polypeptide:retinoid complex. In the example above, the glutamine at position 4 of the CRBPII polypeptide is about 4.5 Å away from the Schiff base formed between the polypeptide and retinal. As shown in Table 2, replacement of this glutamine at position 4 has a large effect on the wavelength of light absorbed and transmitted as well as a significant effect upon the pKa of the protonated Schiff base (PSB) formed between retinal and the lysine (or glutamine) at position 108. Removal of the glutamine at position 4 destabilizes the ground state of the protonated Schiff base, resulting in a lower pKa and a more red-shifted CRBPII: retinal complex. Placement of a positive charge at position 4 (e.g., with arginine) generates a very red-shifted CRBPII: retinal complex, but this complex also has a low pKa.

Replacement of a threonine at any of positions 32-34 with another amino acid also modulates the light absorption and transmission properties. For example, replacing an alanine (A) at position 33 of the Q108K; K40L; T51V; R58W; T53C; T29L; Y19W; Q4R hCRBPII polypeptide with a tryptophan, yields a polypeptide with the following sequence (SEQ ID NO: 28), that is referred to as the Q108K; K40L; T51V; R58W; T53C; T29L; Y19W; Q4R; A33W hCRBPII polypeptide. This polypeptide is an even more red-shifted CRBPII; retinal complex, with a maximal wavelength of absorption at 644 nm.

```
  1 TRDRNGTWEM ESNENFEGWM KALDIDFALR KIWVRLTQTL

41 VIDQDGDNFK VKCTSTFWNY DVDFTVGVEF DEYTKSLDNR

81 HVKALVTWEG DVLVCVQKGE KENRGWKKWI EGDKLYLELT

121 CGDQVCRQV FKKK
```

As is known to the skilled artisan, sequence variation can occur across species. Thus, a rat cellular retinol binding protein II polypeptide sequence with an NCBI accession number of P06768.3 (GI: 132399) has a slightly different sequence than the human cellular retinol binding protein II polypeptide sequences. This rat sequence is provided below for easy reference as SEQ ID NO:29.

```
  1 TKDQNGTWEM ESNENFEGYM KALDIDFATR KIAVRLTQTK

41 IIVQDGDNFK TKTNSTFRNY DLDFTVGVEF DEHTKGLDGR

81 NVKTLVTWEG NTLVCVQKGE KENRGWKQWV EGDKLYLELT

121 CGDQVCRQV FKKK
```

A nucleic acid sequence for this rat cellular retinol binding protein II polypeptide is available in the NCBI database as accession number NM_012640.2 (GI: 78126162). This sequence is provided below for easy reference as SEQ ID NO:30.

```
  1 GCAGCTTGTT CCTTCACGGT CACCAAACGT CCGCATCAAA

41 CCAGAGGCCG CCATCATGAC GAAGGACCAG AATGGAACCT

81 GGGAAATGGA GAGTAATGAG AACTTTGAAG GCTACATGAA

121 GGCCCTAGAT ATTGATTTTG CCACCCGCAA GATTGCAGTG

161 CGTCTGACTC AGACGAAGAT CATCGTTCAA GACGGTGATA

201 ACTTCAAGAC AAAAACCAAC AGCACGTTCC GCAACTATGA

241 CCTAGATTTC ACAGTGGGGG TGGAGTTTGA CGAACACACA

281 AAGGGTCTGG ATGGCCGGAA CGTCAAGACC CTAGTCACCT

321 GGGAAGGAAA CACCCTGGTG TGTGTGCAGA AAGGGGAGAA

361 GGAGAATCGT GGCTGGAAGC AGTGGGTCGA GGGAGACAAG

401 CTGTACCTGG AGCTGACCTG CGGTGACCAG GTGTGTCGAC

441 AAGTGTTCAA AAAGAAGTGA TGGGCCCAGG GGAAGCCTGG

481 AACATGTGTA GAGTTCTCTG CCATTCTGAA AAGCAGCATT

521 GGGACTCCCT GGTTCCTGAC AGAGCCCCCC TTGCATCACC

561 TGCCTGGGTT TGAAACAGGG TGTGTTAAAG GAACCTACCC

601 CCTCCCCCTT AGAACCTATT ATTAAATAAA AAAACAAAAC

641 ATCCTCTCGG CCTTTGAAAA AAAAAAAAA AAAA
```

A mouse cellular retinol binding protein II polypeptide sequence is available in the NCBI database as accession number Q08652.2 (GI: 730494). This sequence is provided below for easy reference as SEQ ID NO:31.

```
  1 TKDQNGTWEM ESNENFEGYM KALDIDFATR KIAVRLTQTK
 41 IITQDGDNFK TKTNSTFRNY DLDFTVGVEF DEHTKGLDGR
 81 HVKTLVTWEG NTLVCVQKGE KENRGWKQWV EGDKLYLELT
121 CGDQVCRQV FKKK
```

A nucleic acid sequence for this mouse cellular retinol binding protein II polypeptide is available in the NCBI database as accession number NM_009034.4 (GI: 255759937). This sequence is provided below for easy reference as SEQ ID NO:32.

```
  1 ATTTAGCATA GTCTCCCTGC AGCCTGTTCC TTCACAGTCA
 41 CCGAACGTCC ACATCAAACC AGAGGCCACC ATCATGACGA
 81 AGGACCAAAA TGGAACCTGG GAAATGGAGA GTAATGAGAA
121 CTTTGAAGGC TACATGAAGG CCCTAGATAT TGATTTTGCC
161 ACCCGCAAGA TCGCAGTGCG TCTGACTCAG ACGAAGATCA
201 TCACTCAAGA CGGTGATAAC TTCAAGACGA AAACCAACAG
241 CACGTTCCGC AACTACGACC TGGATTTCAC CGTCGGGGTG
281 GAGTTTGACG AACACACAAA GGGCCTGGAC GGCCGACATG
321 TCAAGACCCT GGTCACCTGG GAAGGCAACA CCCTCGTGTG
361 TGTGCAGAAA GGGGAGAAGG AGAACCGTGG CTGGAAGCAG
401 TGGGTGGAGG GAGACAAGCT GTACCTGGAG CTGACCTGCG
441 GCGACCAGGT GTGCCGACAA GTGTTCAAAA AGAAGTGATG
481 GGCACGGGAA AGCCTGGAAC ATGTGCAGAG TTCTCTGCCA
521 GTTCCCCAAA GCAGCATGGG GACTCCTCCC ATTCCTGACA
561 GAGCCCCCTT ACATCATCTG CCTGGGTTTA AACTGGAGTG
601 TATAAAAGGA ACCTACCCCC CTCCCAGCCC CCCCCCCCAA
641 GCTTGTTATT AAAGAAACAA AATGTCCTCT CA
```

Other types of polypeptides, which bind vitamin A-like molecules can be used for making fluorescent and colorimetric labeling agents. For example, cellular retinoic acid-binding protein 2 polypeptides (CRABPII) can be used for making fluorescent and colorimetric labeling agents.

One sequence for a human cellular retinoic acid-binding protein 2 amino acid sequence (hCRABPII) polypeptide is provided in the NCBI database as accession number NP_001186652.1 (GI: 315013542). This sequence is provided below for easy reference as SEQ ID NO:33.

```
  1 MPNFSGNWKI IRSENFEELL KVLGVNVMLR KIAVAAASKP
 41 AVEIKQEGDT FYIKTSTTVR TTEINFKVGE EFEEQTVDGR
 81 PCKSLVKWES ENKMVCEQKL LKGEGPKTSW TRELTNDGEL
121 ILTMTADDVV CTRVYVRE
```

A nucleic acid sequence for this human cellular retinoic acid-binding protein 2 polypeptide is available in the NCBI database as accession number NM_001199723.1 (GI: 315013541). This sequence is provided below for easy reference as SEQ ID NO:34.

```
   1 GATTCAAGTG CTGGCTTTGC GTCCGCTTCC CCATCCACTT
  41 ACTAGCGCAG GAGAAGGCTA TCTCGGTCCC CAGAGAAGCC
  81 TGGACCCACA CGCGGGCTAG ATCCAGAGAA CCTGACGACC
 121 CGGCGACGGC GACGTCTCTT TTGACTAAAA GACAGTGTCC
 161 AGTGCTCCAG CCTAGGAGTC TACGGGGACC GCCTCCCGCG
 201 CCGCCACCAT GCCCAACTTC TCTGGCAACT GGAAAATCAT
 241 CCGATCGGAA AACTTCGAGG AATTGCTCAA AGTGCTGGGG
 281 GTGAATGTGA TGCTGAGGAA GATTGCTGTG GCTGCAGCGT
 321 CCAAGCCAGC AGTGGAGATC AAACAGGAGG GAGACACTTT
 361 CTACATCAAA ACCTCCACCA CCGTGCGCAC CACAGAGATT
 401 AACTTCAAGG TTGGGGAGGA GTTTGAGGAG CAGACTGTGG
 441 ATGGGAGGCC CTGTAAGAGC CTGGTGAAAT GGGAGAGTGA
 481 GAATAAAATG GTCTGTGAGC AGAAGCTCCT GAAGGGAGAG
 521 GGCCCCAAGA CCTCGTGGAC CAGAGAACTG ACCAACGATG
 561 GGGAACTGAT CCTGACCATG ACGGCGGATG ACGTTGTGTG
 601 CACCAGGGTC TACGTCCGAG AGTGAGTGGC CACAGGTAGA
 641 ACCGCGGCCG AAGCCCACCA CTGGCCATGC TCACCGCCCT
 681 GCTTCACTGC CCCCTCCGTC CCACCCCCTC CTTCTAGGAT
 721 AGCGCTCCCC TTACCCCAGT CACTTCTGGG GGTCACTGGG
 761 ATGCCTCTTG CAGGGTCTTG CTTTCTTTGA CCTCTTCTCT
 801 CCTCCCCTAC ACCAACAAAG AGGAATGGCT GCAAGAGCCC
 841 AGATCACCCA TTCCGGGTTC ACTCCCCGCC TCCCCAAGTC
 881 AGCAGTCCTA GCCCCAAACC AGCCCAGAGC AGGGTCTCTC
 921 TAAAGGGGAC TTGAGGGCCT GAGCAGGAAA GACTGGCCCT
 961 CTAGCTTCTA CCCTTTGTCC CTGTAGCCTA TACAGTTTAG
1001 AATATTTATT TGTTAATTTT ATTAAAATGC TTTAAAAAAA
1041 TAAAAAAAAA AAAAAAAAAA AAAAAAAAA AAAAA
```

Another human CRABPII polypeptide sequences is available in the NCBI database as accession number CAI16339.1 (GI: 55960771). This sequence is provided below for easy reference as SEQ ID NO:35.

```
  1 MPNFSGNWKI IRSENFEELL KVLGVNVMLR KIAVAAASKP
 41 AVEIKQEGDT FYIKTSTTVR TTEINFKVGE EFEEQTVDGR
 81 PCKSLVKWES ENKMVCEQKL LKGEGPKTSW TRELTNDGEL
121 ILTMTADDVV CTRVYVRE
```

A nucleic acid sequence for this human cellular retinoic acid-binding protein 2 (CRABPII) polypeptide is available in the NCBI database as accession number NM_001199723.1 (GI: 315013541). This sequence is provided below for easy reference as SEQ ID NO:36.

```
  1 GATTCAAGTG CTGGCTTTGC GTCCGCTTCC CCATCCACTT
 41 ACTAGCGCAG GAGAAGGCTA TCTCGGTCCC CAGAGAAGCC
```

-continued

```
 81 TGGACCCACA CGCGGGCTAG ATCCAGAGAA CCTGACGACC
121 CGGCGACGGC GACGTCTCTT TTGACTAAAA GACAGTGTCC
161 AGTGCTCCAG CCTAGGAGTC TACGGGGACC GCCTCCCGCG
201 CCGCCACCAT GCCCAACTTC TCTGGCAACT GGAAAATCAT
241 CCGATCGGAA AACTTCGAGG AATTGCTCAA AGTGCTGGGG
281 GTGAATGTGA TGCTGAGGAA GATTGCTGTG GCTGCAGCGT
321 CCAAGCCAGC AGTGGAGATC AAACAGGAGG GAGACACTTT
361 CTACATCAAA ACCTCCACCA CCGTGCGCAC CACAGAGATT
401 AACTTCAAGG TTGGGGAGGA GTTTGAGGAG CAGACTGTGG
441 ATGGGAGGCC CTGTAAGAGC CTGGTGAAAT GGGAGAGTGA
481 GAATAAAATG GTCTGTGAGC AGAAGCTCCT GAAGGGAGAG
521 GGCCCCAAGA CCTCGTGGAC CAGAGAACTG ACCAACGATG
561 GGGAACTGAT CCTGACCATG ACGGCGGATG ACGTTGTGTG
601 CACCAGGGTC TACGTCCGAG AGTGAGTGGC ACAGGTAGA
641 ACCGCGGCCG AAGCCCACCA CTGGCCATGC TCACCGCCCT
681 GCTTCACTGC CCCCTCCGTC CCACCCCCTC CTTCTAGGAT
721 AGCGCTCCCC TTACCCCAGT CACTTCTGGG GGTCACTGGG
761 ATGCCTCTTG CAGGGTCTTG CTTTCTTTGA CCTCTTCTCT
801 CCTCCCCTAC ACCAACAAAG AGGAATGGCT GCAAGAGCCC
841 AGATCACCCA TTCCGGGTTC ACTCCCCGCC TCCCCAAGTC
881 AGCAGTCCTA GCCCCAAACC AGCCCAGAGC AGGGTCTCTC
921 TAAAGGGGAC TTGAGGGCCT GAGCAGGAAA GACTGGCCCT
961 CTAGCTTCTA CCCTTTGTCC CTGTAGCCTA TACAGTTTAG
1001 AATATTTATT TGTTAATTTT ATTAAAATGC TTTAAAAAAA
1041 TAAAAAAAAA AAAAAAAAA AAAAAAAAA AAAAA
```

As is known to the skilled artisan, sequence variation can be present in human polypeptides, including CRABPII polypeptides. Thus, isoforms of CRABPII exist. For example, CRABPII isoform CRA has an amino acid sequence that is present in the NCBI database as accession number EAW52922.1 (GI: 119573307). This sequence is provided below for easy reference as SEQ ID NO:37.

```
  1 MPNFSGNWKI IRSENFEELL KVLGVNVMLR KIAVAAASKP
 41 AVEIKQEGDT FYIKTSTTVR TTEINFKVGE EFEEQTVDGR
 81 PCKSLVKWES ENKMVCEQKL LKGEGPKTSW TRELTNDGEL
121 ILTMTADDVV CTRVYVRE
```

A nucleic acid sequence for this CRABPII isoform CRA polypeptide is available in the NCBI database as accession number NM_001878.3 (GI: 315013540). This sequence is provided below for easy reference as SEQ ID NO:38.

```
  1 GGAGCGGGAG GCGGGGCCAC TTCAATCCTG GGCAGGGGCG
 41 GTTCCGTACA GGGTATAAAA GCTGTCCGCG CGGGAGCCCA
```

```
 81 GGCCAGCTTT GGGGTTGTCC CTGGACTTGT CTTGGTTCCA
121 GAACCTGACG ACCCGGCGAC GGCGACGTCT CTTTTGACTA
161 AAAGACAGTG TCCAGTGCTC CAGCCTAGGA GTCTACGGGG
201 ACCGCCTCCC GCGCCGCCAC CATGCCCAAC TTCTCTGGCA
241 ACTGGAAAAT CATCCGATCG GAAAACTTCG AGGAATTGCT
281 CAAAGTGCTG GGGGTGAATG TGATGCTGAG GAAGATTGCT
321 GTGGCTGCAG CGTCCAAGCC AGCAGTGGAG ATCAAACAGG
361 AGGGAGACAC TTTCTACATC AAAACCTCCA CCACCGTGCG
401 CACCACAGAG ATTAACTTCA AGGTTGGGGA GGAGTTTGAG
441 GAGCAGACTG TGGATGGGAG GCCCTGTAAG AGCCTGGTGA
481 AATGGGAGAG TGAGAATAAA ATGGTCTGTG AGCAGAAGCT
521 CCTGAAGGGA GAGGGCCCCA AGACCTCGTG GACCAGAGAA
561 CTGACCAACG ATGGGGAACT GATCCTGACC ATGACGGCGG
601 ATGACGTTGT GTGCACCAGG GTCTACGTCC GAGAGTGAGT
641 GGCCACAGGT AGAACCGCGG CCGAAGCCCA CCACTGGCCA
681 TGCTCACCGC CCTGCTTCAC TGCCCCCTCC GTCCCACCCC
721 CTCCTTCTAG GATAGCGCTC CCCTTACCCC AGTCACTTCT
761 GGGGGTCACT GGGATGCCTC TTGCAGGGTC TTGCTTTCTT
801 TGACCTCTTC TCTCCTCCCC TACACCAACA AAGAGGAATG
841 GCTGCAAGAG CCCAGATCAC CCATTCCGGG TTCACTCCCC
881 GCCTCCCCAA GTCAGCAGTC CTAGCCCCAA ACCAGCCCAG
921 AGCAGGGTCT CTCTAAAGGG GACTTGAGGG CCTGAGCAGG
961 AAAGACTGGC CCTCTAGCTT CTACCCTTTG TCCCTGTAGC
1001 CTATACAGTT TAGAATATTT ATTTGTTAAT TTTATTAAAA
1041 TGCTTTAAAA AATAAAAAA AAAAAAAAA AAAAAAAAA
1081 AAAAAAAA
```

As illustrated herein, CRABPII polypeptides with modified amino acid sequences exhibit different light transmission and emission properties (see the Examples and FIGS. 5-8). Moreover, a number of other CRABPII polypeptides can be used as potential pH sensors, which occupy the pKa range from 2.7 to 7.0.

For example, the following modified R111K:C130X: R132X:Y134X:F3X:I9X:S12X:F15X:L19X:V24X:A32X: A35X:A36X:S37X:K38X:P39X:Q45X:T54X:T56X:T57X: V58X:R59X:T61X:E73X:Q74X:V76X:G78X:C81X: M93X:C95X:L121X:M123X CRABPII polypeptide (SEQ ID NO:46) shows amino acid positions that can readily be modified to achieve desirable light transmission and emission properties when complexed with a retinoid or fluorescent dye ligand, as well as desirable stability in response to changes in temperature and pH.

```
  1 MPNXSGNWKX IRXENXEELX KVLGXNVMLR KIXVAXXXXX
 41 AVEIKXEGDT FYIKXSXXXX TXEINFKVGE EFEXXTXDXR
```

```
 81  PXKSLVKWES ENKXVXEQKL LKGEGPKTSW TKELTNDGEL
121  IXTXTADDVV XTXVXVRE
``` wherein each X is independently a genetically encoded L-amino acid, a naturally-occurring non-genetically encoded L-amino acid, a synthetic L-amino acid or a synthetic D-amino acid.

Similarly, the following modified Q108K:R2X:F16X: Y19X:M20X:I25X:T29X:A33X:Q38X:K40X:I42X:T51X: T53X:S55X:F57X:R58X:Y60X:V62X:F64X:E72X:S76X: L77X:C95X:Q97X:R104X:W106X:L117X:L119X:Q128X: F130X CRBPII polypeptide (SEQ ID NO:47) shows amino acid positions that can readily be modified to achieve desirable light transmission and emission properties when complexed with a retinoid or fluorescent dye ligand, as well as desirable stability in response to changes in temperature and pH.

```
  1  TXDXNGTWEM ESNENXEGXX KALDXDFAXR KIXVRLTXTX
 41  VXDQDGDNFK XKXTXTXXNX DXDXTVGVEF DXYTKXXDNR
 81  HVKALVTWEG DVLVXVXKGE KENXGXKXWI EGDKLYXEXT
121  CGDQVCRXVX KKK
``` wherein each X is independently a genetically encoded L-amino acid, a naturally-occurring non-genetically encoded L-amino acid, a synthetic L-amino acid or a synthetic D-amino acid.

Thus, the polypeptides described herein can have amino acid sequences comprised of any available amino acid Amino acids included in the peptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 3. These amino acids can be linked together, for example, by peptidyl linkages, intersubunit linkages, or other intersubunit linkages that are consistent with enzyme-substrate or receptor-ligand binding interactions.

TABLE 3

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydroisoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-Amino valeric acid | | Ava |
| 2,3-Diaminobutyric acid | | Dab |

Certain amino acids that are not genetically encoded can be present in polypeptides of the invention including β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2, 3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer).

The classifications of the above-described genetically encoded and non-encoded amino acids are summarized in Table 4, below. It is to be understood that Table 4 is for illustrative purposes only and does not purport to be an exhaustive list of amino acid residues which may comprise the polypeptides described herein. Other amino acid residues which are useful for making the polypeptides described herein can be found, e.g., in Fasman, 1989, CRC Practical Handbook of Biochemistry and Molecular Biology, CRC Press, Inc., and the references cited therein Amino acids not specifically mentioned herein can be conveniently classified on the basis of known behavior and/or their characteristic chemical and/or physical properties as compared with amino acids specifically identified.

TABLE 4

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

The colorimetric/fluorescent polypeptides can be complexed with retinal and other dyes either covalently or non-covalently. In some embodiments, the complex between the polypeptide and retinal (or another dye) is non-covalent. In other embodiments, a covalent bond between the polypeptide and retinal (or another dye) forms spontaneously by attack of an amino acid in the polypeptide upon an active group in the retinal or dye. For example, when lysine is present at position 108 of the hCRBPII polypeptide (instead of glutamine), such a Q108K hCRBPII polypeptide and adopts a favorable three-dimensional structure for positioning the lysine to attack the retinal aldehyde to form a protonated Schiff base.

Generating Modified Colorimetric/Fluorescent Polypeptides

The colorimetric/fluorescent polypeptides described herein may be synthesized by methods available in the art, including recombinant DNA methods and chemical synthesis.

Chemical synthesis may be performed using standard solution phase or solid phase peptide synthesis techniques, in which a peptide linkage occurs through the direct condensation of the α-amino group of one amino acid with the carboxy group of the other amino acid with the elimination of a water molecule. Peptide bond synthesis by direct condensation, as formulated above, may involve suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection may be necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc. 85:2149, 1963, which involves assembling a linear peptide chain on a resin support using protected amino acids. Solid phase peptide synthesis typically utilizes either the Boc or Fmoc strategy, which are now well known in the art.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

The modified iLBP colorimetric/fluorescent polypeptides described herein may be synthesized by recombinant DNA methods. Therefore, another aspect of the invention is a nucleic acid encoding modified iLBP colorimetric/fluorescent polypeptides described herein.

As used herein, the term "isolated" refers to a nucleic acid, polypeptide or amino acid (or other component) that is removed from at least one component with which it is naturally associated. The isolated nucleic acid, polypeptide or amino acid (or other component) can, but need not, be purified. Instead, the isolated nucleic acid, polypeptide or amino acid (or other component), while not within its natural environment, may be present in another environment, for example, a host cell that normally does not have such an isolated nucleic acid, polypeptide or amino acid (or other component).

Modifications to the amino acid sequences of the colorimetric/fluorescent polypeptides can be preparing a modified nucleic acid that encodes the colorimetric/fluorescent polypeptide. The term "modified nucleic acid" herein refers to a DNA or RNA that has been altered to contain at least one mutation to encode a modified iLBP colorimetric/fluorescent polypeptide.

Several methods are known in the art that are suitable for generating modified nucleic acids, including but not limited to site-saturation mutagenesis, scanning mutagenesis, insertional mutagenesis, deletion mutagenesis, random mutagenesis, site-directed mutagenesis, and directed-evolution, as well as various other recombinatorial approaches. The commonly used methods include DNA shuffling (Stemmer W P, Proc Natl Acad Sci USA. 25; 91(22):10747-51 [1994]), methods based on non-homologous recombination of genes e.g. ITCHY (Ostermeier et al., Bioorg Med Chem. 7(10): 2139-44 [1999]), SCRACHY (Lutz et al. Proc Natl Acad Sci USA. 98(20):11248-53 [2001]), SHIPREC (Sieber et al., Nat Biotechnol. 19(5):456-60 [2001]), and NRR (Bittker et al., Nat Biotechnol. 20(10):1024-9 [2001]; Bittker et al., Proc Natl Acad Sci USA. 101(18):7011-6 [2004]), and methods that rely on the use of oligonucleotides to insert random and targeted mutations, deletions and/or insertions (Ness et al., Nat Biotechnol. 20(12):1251-5 [2002]; Coco et al., Nat Biotechnol. 20(12):1246-50 [2002]; Zha et al., Chembiochem. 3; 4(1):34-9 [2003], Glaser et al., J Immunol. 149(12):3903-13 [1992], Sondek and Shortle, Proc Natl Acad Sci USA 89(8):3581-5 [1992], Yanez et al., Nucleic Acids Res. 32(20):e158 [2004], Osuna et al., Nucleic Acids Res. 32(17):e136 [2004], Gaytan et al., Nucleic Acids Res. 29(3):E9 [2001], and Gaytan et al., Nucleic Acids Res. 30(16):e84 [2002]).

In some embodiments, the modified nucleic acid encodes an amino acid substitution at least at one amino acid position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 89, 90, 91, 92, 93, 94, 95, 96, 97, 98, 99, 100, 101, 102, 103, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, of an ILBP polypeptide, for example, a polypeptide with any of SEQ ID NO:1, 3, 5, 6-29, 31, 33, 35, 37, 39-46 and 47. In some embodiments, the modified colorimetric/fluorescent polypeptides is at least about 65%, at least about 70%, at least about 75%, at least about 80%, at least about 85%, at least about 90%, at least about 95%, at least about 97%, at least about 98%, at least about 99% identical to any of the iLBP polypeptides referred to herein, including those with SEQ ID NO:1, 3, 5, 6-29, 31, 33, 35, 37, 39-44 and 45.

As is known by one with skill in the art, the genetic code is "degenerate," meaning that several trinucleotide codons can encode the same amino acid. This degeneracy is apparent from Table 5.

TABLE 5

| 1st Position | T | | C | | A | | G | | 3rd Position |
|---|---|---|---|---|---|---|---|---|---|
| | | | | | Second Position | | | | |
| T | TTT = Phe | | TCT = Ser | TAT = Tyr | | TGT = Cys | | | T |
| T | TTC = Phe | | TCC = Ser | TAC = Tyr | | TGC = Cys | | | C |
| T | TTA = Leu | | TCA = Ser | TAA = Stop | | TGA = Stop | | | A |
| T | TTG = Leu | | TCG = Ser | TAG = Stop | | TGG = Trp | | | G |
| C | CTT = Leu | | CCT = Pro | CAT = His | | CGT = Arg | | | T |
| C | CTC = Leu | | CCC = Pro | CAC = His | | CGC = Arg | | | C |
| C | CTA = Leu | | CCA = Pro | CAA = Gln | | CGA = Arg | | | A |
| C | CTG = Leu | | CCG = Pro | CAG = Gln | | CGG = Arg | | | G |
| A | ATT = Ile | | ACT = Thr | AAT = Asn | | AGT = Ser | | | T |
| A | ATC = Ile | | ACC = Thr | AAC = Asn | | AGC = Ser | | | C |
| A | ATA = Ile | | ACA = Thr | AAA = Lys | | AGA = Arg | | | A |
| A | ATG = Met | | ACG = Thr | AAG = Lys | | AGG = Arg | | | G |
| G | GTT = Val | | GCT = Ala | GAT = Asp | | GGT = Gly | | | T |
| G | GTC = Val | | GCC = Ala | GAC = Asp | | GGC = Gly | | | C |
| G | GTA = Val | | GCA = Ala | GAA = Gln | | GGA = Gly | | | A |
| G | GTG = Val | | GCG = Ala | GAG = Gln | | GGG = Gly | | | G |

Hence, many changes in the nucleotide sequence of the isolated nucleic acids described herein may be silent and may not alter the amino acid sequence encoded by the nucleic acid. Where nucleic acid sequence alterations are silent, an isolated nucleic acid will encode a polypeptide with the same amino acid sequence as the reference nucleic acid. Therefore, a particular nucleic acid sequence of the invention also encompasses variants with degenerate codon substitutions, and complementary sequences thereof, as well as the sequence explicitly specified by a SEQ ID NO. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., Nucleic Acid Res., 19, 5081 (1991) and/or Ohtsuka et al., J. Biol. Chem., 260, 2605 (1985); Rossolini et al., Mol. Cell. Probes, 8, 91 (1994).

The modified nucleic acid can be operably linked to one or more nucleic acid segments that encode one or more regulatory elements. Such a construct is referred to as an "expression cassette."

The term "regulatory element," as used herein, refers to any nucleic acid segment with a sequence that influences transcription or translation initiation and rate, or stability and/or mobility of a transcript or polypeptide product. Regulatory element sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, and combinations thereof.

The expression cassettes comprising a modified nucleic acid that encodes a modified iLBP polypeptide can be included within a vector to facilitate manipulation, maintenance, replication, and/or expansion of the modified nucleic acids as well as expression polypeptides encoded within the modified iLBP polypeptides.

The vector backbone can be any of those employed in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996); [0183](b) YAC: Burke et al., Science 236:806-812 (1987); (c) PAC: Sternberg N. et al., Proc Natl Acad Sci USA. January; 87(1):103-7 (1990); (d) Bacteria-Yeast Shuttle Vectors: Bradshaw et al., Nucl Acids Res 23: 4850-4856 (1995); (e) Lambda Phage Vectors: Replacement Vector, e.g., Frischauf et al., J. Mol Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors: Walden et al., Mol Cell Biol 1: 175-194 (1990); and (g) Plasmid vectors: Sambrook et al., infra.

Retinoid Ligands

The modified iLBPs of the invention bind retinoid ligands yielding a iLBP-retinoid complexes that absorb and transmit light. Retinoids are a class of chemical compounds that are related chemically to vitamin A. Such retinoids include retinal, retinol, tretinoin, isotretinoin, etretinate, acitretin, carotenoid, vitamin A, and retinoic acid.

Vitamin A is metabolized into the light-absorbing molecule retinal, which is needed by animals for both low-light (scotopic vision) and color vision. The major form of vitamin A in food from animal sources is an ester, for example, retinyl palmitate. The vitamin A ester is converted to retinol in the small intestine, which functions as a storage form of the vitamin, and which can be converted to and from its visually active aldehyde form, retinal. Retinoic acid is a metabolite that can be irreversibly synthesized from vitamin A, but it has only partial vitamin A activity.

Retinoids have a ring to which a isoprenoid chain, called a retinyl group, is attached. In some embodiments, the ring is an aromatic ring. In other embodiments, the ring is a beta-ionone ring to which an isoprenoid chain is attached. Both the ring and the isoprenoid chain are needed for vitamin activity. The orange pigment of carrots—beta-carotene—can be represented as two connected retinyl groups, which are used in the body to contribute to vitamin A levels. Alpha-carotene and gamma-carotene also have a single retinyl group, which give them some vitamin activity. None of the other carotenes have vitamin activity. The carotenoid beta-cryptoxanthin possesses an ionone group and has vitamin activity in humans. The structures of retinoic acid and retinol are shown below.

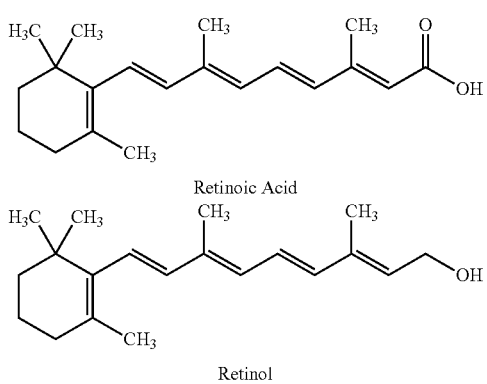

Retinoic Acid

Retinol

Retinal is also called retinaldehyde or vitamin A aldehyde. It is a polyene chromophore that binds to proteins called opsins. The structure of all-trans-retinal is shown below.

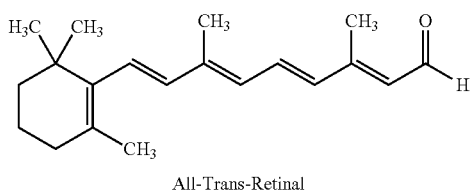 [SMILES: CC1=C(/C=C/C(C)=C/C=C/C(C)=C/C=O)C(C)(C)CCC1]

All-Trans-Retinal

All of the retinoids and related vitamin A-like molecules can be used as ligands for the modified iLBPs of the invention of the invention in order to form fluorescent and colorimetric labeling agents. Thus, the retinoid molecule is added or administered to the modified iLBPs of the invention of the invention, which bind the retinoid ligands, and thereby form fluorescent and colorimetric labeling agents. In general the modified iLBPs of the invention of the invention bind retinal as the retinoid ligand molecule in order to absorb and transmit light. However, in some embodiments, retinol, tretinoin, isotretinoin, etretinate, acitretin, carotenoid, vitamin A, retinoic acid or other vitamin A-like molecules are used, added or administered either because the modified polypeptide can bind those retinoids or because such retinoids can be converted into another retinoid (e.g., retinal) by cellular enzymes.

Other Dye Ligands

The invention also relates to dye ligand compounds that can bind the modified iLBP polypeptides described herein, for example, via formation of a Schiff base formed between an amino group in the iLBP polypeptide and an aldehyde (—CHO) on the dye ligand molecule. The iLBP-dye ligand complex transmits light and/or is fluorescent.

Thus, one aspect of the invention is a dye ligand of formula I:

Ring-Y—CHO wherein:
Ring is an optionally substituted $C_5$-$C_{14}$ mono-, di- or tricyclic cycloalkyl, aryl or heterocyclic ring, wherein the heterocyclic ring has at least one nitrogen or oxygen ring atom, and wherein the Ring has 1-3 optional substituents that are selected from the group consisting of alkyl, halogen, alkoxy, amino and sulfhydryl; and
Y is a divalent $C_2$-$C_{12}$ alkenylene chain that optionally substituted with 1-3 alkyl groups.

In other embodiments, the merocyanine dye is a compound of formula II:

$Ar_1$—$Y_1$—CHO wherein:
$Ar_1$ is a $C_5$-$C_{10}$ mono- or dicyclic heterocyclic ring system, with at least one nitrogen or oxygen ring atom; and
$Y_1$ is a divalent $C_2$-$C_{12}$ alkenylene chain that is optionally substituted with 1-3 alkyl groups.

In some embodiments, Ring is monocyclic. In other embodiments, the Ring is bicyclic. When the Ring is a heterocyclic ring it can be a mono-, di- or tricyclic heteroaryl ring, where at least one of the rings in the heteroaryl ring is aromatic.

The alkenylene chain can include a —(CH═CH)$_n$— chain where n is an integer of from 1 to 6, and where the alkenylene chain can be substituted with 1-3 alkyl groups, where the alkyl groups have from 1 to about 10 carbon atoms, and typically from 1 to 6 carbons or, in some embodiments, from 1 to 3 carbon atoms.

One example of a merocyanine dye that can be used with the colorimetric/fluorescent proteins described herein has the following structure.

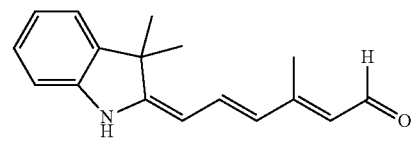 [SMILES: CC(/C=C/C=C1/Nc2ccccc2C1(C)C)=C\C=O]

When the dye binds to a modified iLBP polypeptide it can form a Schiff base that is pH sensitive as shown below.

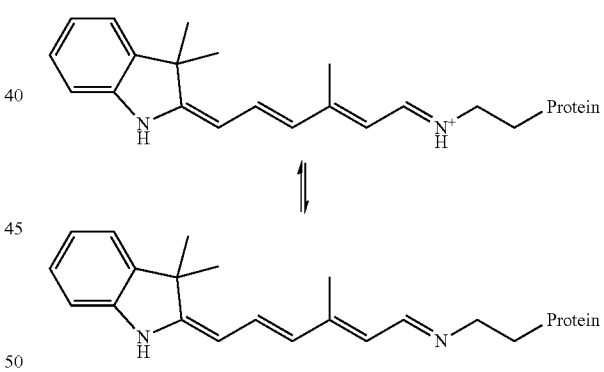

As illustrated, this compound can form a Schiff base with the protein, where the Schiff base is protonated at acidic pH and not protonated at basic pH.

Fusion Proteins

The colorimetric/fluorescent polypeptides described herein can be fused to any molecule or fusion partner of interest. The combination of the colorimetric/fluorescent polypeptide and the fusion partner is referred to as a "fusion protein" even if a portion of the fusion protein is not a polypeptide.

The terms "fusion protein" and "chimeric protein," as used herein, are interchangeable and refer to polypeptides and proteins which comprise a colorimetric/fluorescent polypeptides described herein and a fusion partner. In some embodiments, a linker can join the colorimetric/fluorescent polypeptide and the fusion partner. In other embodiments, the colorimetric/fluorescent polypeptide and the fusion partner fused directly together. When the fusion partner is a protein, it may be fused in frame, for example, to facilitate recombinant synthesis or allow the fusion protein to be made in vivo.

Fusion partners can include any naturally occurring, or synthetic, molecule, component or material. Examples of fusion partners or molecules to which the colorimetric/fluorescent polypeptides described herein can be fused include biological molecules, small synthetic molecules, proteins, antibodies, antibody fragments, nucleic acids, polysaccharides, glycans, therapeutic agents, drugs, pharmaceuticals, ligands, cofactors, vitamins, polymers, intracellular molecules, extracellular molecules, viruses, viral components, subcellular structures, cellular organelles, cells, neurons, axons, dendrites, membranes, secreted factors, secreted materials, toxins, waste products, dyes, labels and the like.

In a further embodiment, a fusion protein may comprise more than one colorimetric/fluorescent polypeptides and/or more than one fusion partner. In these embodiments, the multiple colorimetric/fluorescent polypeptides may be the same or different, the multiple fusion partners may be the same or different. One or more linkers can be used to join the colorimetric/fluorescent polypeptides and/or fusion partners.

In one embodiment, fusion partner is biologically active. Examples of fusion partners include, but are not limited to, interleukin (IL)-11, thymosin β4, thymosin α1, IL-2, IL-3, IL-4, IL-5, IL-6, IL-7, IL-8, IL-10, IL-13, IL-15, IL-18, Protease-activated receptor 1 (PAR1), PAR3, PAR4, RANTES, stromal cell-derived factor-la, monocyte chemotactic protein, stem cell factor, FLT-3L, parathyroid hormone, thrombopoietin, epidermal growth factor, basic fibroblast growth factor, insulin-like growth factor, granulocyte-macrophage colony stimulating factor, granulocyte colony stimulating factor, macrophage colony stimulating factor, platelet-derived growth factor, transforming growth factor (TGF)-β1, tumor necrosis factor (TNF)-α, interferon (IFN)-α, IFN-γ, hepatocyte growth factor, vascular endothelial growth factor, an immunoglobulin heavy chain, an immunoglobulin light chain and other molecules of interest to those of skill in the art.

In some embodiments, the fusion partner is a target protein, where the target protein is a biological molecule whose in vivo location, function and/or activity is of interest to one of skill in the art. For example, the target protein can be any fusion partner described herein Fusion Protein Synthesis The colorimetric/fluorescent polypeptide and the fusion partner can be synthetically, recombinantly, or chemically fused.

In some embodiments, the modified iLBP colorimetric/fluorescent polypeptide and the fusion partner are recombinantly fused by joining or ligating a nucleic acid that encodes the modified iLBP polypeptide with a nucleic acid that encodes the fusion partner.

The nucleic acids coding for the colorimetric/fluorescent polypeptide and the fusion partner are isolated, synthesized or otherwise obtained and fused in frame together to form a hybrid nucleic acid containing the coding region for the colorimetric/fluorescent polypeptide and the coding region for the fusion partner. In one embodiment, the nucleic acids are ligated together using a ligase. The hybrid nucleic acid can then be operably linked to nucleic acids encoding regulatory elements. The term "operably linked," as used herein, refers to a regulatory element being linked to a nucleic acid encoding a colorimetric/fluorescent polypeptide, fusion partner or fusion protein in such a manner that the regulatory element exerts an effect on the transcription and/or translation of the nucleic acid.

The nucleic acid(s) encoding a colorimetric/fluorescent polypeptide, fusion partner or fusion protein can be placed, maintained, replicated, or amplified within a vector (e.g., a plasmid, virus, or bacteriophage vector). In one embodiment, the vector is an expression vector. The vector can be autonomously replicable in a host cell. The vector can also contain a selectable marker. Selectable markers include nucleic acids encoding drug resistance (e.g., ampicillin or tetracycline), an enzyme activity, an auxotrophy complement or an inert protein that may be detected in a host cell by methods known in the art. For example, the selectable marker may be green fluorescent protein that may be detected upon expression in a host cell by visualization through light microscopy under ultra-violet light.

The vector can include nucleic acid segments encoding regulatory sequences (e.g., transcription and translation elements) to control expression of the colorimetric/fluorescent polypeptide, fusion partner or fusion protein in a suitable host cell. The regulatory sequences may include one or more of promoter regions, enhancer regions, transcription termination sites, ribosome binding sites, initiation codons, splice signals, introns, polyadenylation signals, Shine/Dalgarno translation sequences, and Kozak consensus sequences. Regulatory sequences are chosen with regard to the host cell in which the colorimetric/fluorescent polypeptide, fusion partner or fusion protein is to be produced. Suitable bacterial promoters include, but are not limited to, bacteriophage λpL or pR, T6, T7, T7/lacO, lac, recA, gal, trp, ara, hut, and trp-lac. Suitable eukaryotic promoters include, but are not limited to, PRBI, GAPDH, metallothionein, thymidine kinase, viral LTR, cytomegalovirus, SV40, or tissue-specific or tumor-specific promoters such as α-fetoprotein, amylase, cathepsin E, M1 muscarinic receptor, or γ-glutamyl transferase.

Colorimetric/fluorescent polypeptides, fusion partners or fusion proteins that are designed to be secreted from a host cell into the culture medium or into the periplasm of the host cell may also contain a signal sequence. The signal sequence may be the fusion partner or may be in addition to the fusion partner. A nucleic acid encoding a signal sequence may be operably linked to the 5' end of the nucleic acid encoding the colorimetric/fluorescent polypeptide, fusion partner or fusion protein. Suitable signal sequences are available in the art and include, for example, MBP, GST, TRX, DsbA, and LamB from *E. coli* and α-factor from yeast.

In some embodiments, the vector can also comprise one or more cloning sites, e.g., restriction enzyme recognition sites, upstream and/or downstream of the nucleic acid(s) encoding a colorimetric/fluorescent polypeptide, fusion partner or fusion protein to facilitate the cloning of these nucleic acid(s). Examples of suitable expression vectors are found in U.S. Pat. No. 5,814,503, which is incorporated herein by reference.

Another aspect of the invention is a method of preparing a nucleic acid encoding a colorimetric/fluorescent polypeptide, fusion partner or fusion protein, comprising inserting a nucleic acid encoding fusion partner into a cloning site of a vector such that the fusion partner nucleic acid is upstream or downstream and in frame with a nucleic acid encoding a colorimetric/fluorescent polypeptide.

Another aspect of the invention is a host cell comprising a vector encoding a colorimetric/fluorescent polypeptide, a fusion partner or a fusion protein. The host cell may be any cell suitable for expression of a colorimetric/fluorescent polypeptide, a fusion partner or fusion protein, including prokaryotic (e.g., bacterial) and eukaryotic (e.g., fungi, yeast, animal, insect, plant) cells. Suitable prokaryotic host cells include, but are not limited to, *E. coli* (e.g., strains DH5, HB101, JM109, or W3110), *Bacillus, Streptomyces, Salmonella, Serratia*, and *Pseudomonas* species. Suitable eukaryotic host cells include cultured eukaryotic cells as well as cells administered to a eukaryotic organism. Examples include cultured mammalian cells, cancer cells, non-cancerous cells, healthy primary cultured cells, cells isolated from mammalian tissues, yeast, COS, CHO, HepG-2, CV-1, LLC-MK$_2$, 3T3, HeLa, RPMI8226, 293, BHK-21, Sf9, *Saccharomyces, Pichia, Hansenula, Kluyveromyces, Aspergillus*, or *Trichoderma* species.

Methods and materials for preparing recombinant vectors and transforming host cells using the same, replicating the vectors in host cells and expressing biologically active foreign polypeptides and proteins are described in Old et al., Principles of Gene Manipulation, 2nd edition, (1981); Sambrook et al., Molecular Cloning, 3rd edition, Cold Spring Harbor Laboratory, 2001, and Ausubel et al., Current Protocols in Molecular Biology, John Wiley & Sons, New York 3rd edition, (2000), each incorporated herein by reference.

Vectors may be introduced into a host cell by any means known in the art, including, but not limited to, transformation, calcium phosphate precipitation, electroporation, lipofection, microinjection, and viral infection.

Another aspect of the invention is a method that involves propagating the modified nucleic acid in a prokaryotic or eukaryotic cell.

Such a method can also or separately involve producing a colorimetric/fluorescent modified iLBP polypeptide, a fusion partner or fusion protein. Such a method can include preparing a vector comprising a nucleic acid encoding a colorimetric/fluorescent polypeptide, a fusion partner and/or a fusion protein, delivering the vector into a host cell, culturing the host cell under conditions in which the a colorimetric/fluorescent polypeptide, a fusion partner and/or fusion protein is expressed, and isolating the colorimetric/fluorescent polypeptide, fusion partner and/or fusion protein.

The colorimetric/fluorescent modified iLBP polypeptide, fusion partner or fusion protein may be separated from the host cell by any means known in the art. If the colorimetric/fluorescent polypeptide, fusion partner or fusion protein is secreted from the host cell, the culture medium containing the colorimetric/fluorescent polypeptide, fusion partner or fusion protein may be collected. If the colorimetric/fluorescent polypeptide, fusion partner or fusion protein is not secreted from the host cell, the cell may be lysed to release the colorimetric/fluorescent polypeptide, fusion partner or fusion protein. For example, bacterial cells may be lysed by application of high pressure (e.g., with a high pressure homogenizer) or by sonication.

Method of Observing Target Molecules In Vivo

According to the invention, target molecules can be observed in vivo by a variety of methods. For example, the target molecule can be observed by detecting the light transmitted or emitted by a modified iLBP protein:retinoid/dye complex when the modified iLBP protein:retinoid/dye complex is associated with, or fused to, a selected target molecule. Thus, in some embodiments a living cell that includes a modified nucleic acid is generated where the modified nucleic acid encodes a fusion protein that includes a fusion protein comprising the modified iLBP polypeptide of the invention fused in frame with the target protein. Upon expression of the fusion protein, and addition of a retinoid or dye ligand to the cell, a colorimetric or fluorescent signal is readily detected so that the location, function and/or activity of the target protein can be observed.

Therefore, another aspect of the invention is a method of observing a target protein in vivo comprising contacting a living cell with a retinoid or dye that binds a modified polypeptide encoded by the isolated nucleic acid of claim 1, wherein the cell expresses a fusion protein comprising the modified polypeptide fused in frame with the target protein.

Thus, a modified nucleic acid can be expressed in an animal cell by inserting the modified nucleic acid into the animal cell (e.g., into the genome of the cell), where the modified nucleic acid encodes a fusion protein comprising the modified polypeptide fused in frame with the target protein, and where the modified nucleic acid is operably linked to a nucleic acid segment encoding at least one regulatory element that promotes expression of the fusion protein. After construction of the animal cell containing such a modified nucleic acid, the cell can be cultured or replicated as desired. When initiating a study involving observing the location, function and/or activity of the target protein within the cell, the cell is exposed to, or contacted with, a retinoid or fluorescent dye that can bind to the modified iLBP polypeptide fused to the target protein.

Another embodiment includes a method for providing an expression cassette or vector that encodes one of the modified iLBP polypeptide described herein, comprising, offering a retinoid or dye plus the expression cassette or vector for sale to a customer along with the right to use retinoid or dye and the expression cassette or vector.

Kits

Another embodiment of the invention is a kit that includes at least one container comprising a nucleic acid encoding a modified iLBP polypeptide, where the modified polypeptide transmits or emits light when bound to a retinoid or fluorescent dye molecule, and where the intracellular lipid binding protein has been modified so that an amino acid at any of positions 102-135 can form a Schiff base with an aldehyde on a retinoid or dye ligand. In some embodiments, the nucleic acid encoding the modified iLBP polypeptide is operably linked to at least one nucleic acid encoding regulatory element. In other embodiments, an expression cassette including the nucleic acid encoding the modified iLBP polypeptide is present within the container of the kit. In further embodiments, a vector comprising the expression cassette that includes the nucleic acid encoding the modified iLBP polypeptide is present within the container of the kit.

The nucleic acid encoding the modified iLBP polypeptide can also include restriction enzyme cleavage sites to facilitate fusion of nucleic acids encoding other peptides and polypeptides (e.g., a fusion partner). Preferably, the restriction enzyme cleavage sites are positioned so that a selected nucleic acid can be joined in-frame to the cleavage site. The kit can therefore also include a container comprising a restriction enzyme for cleaving the nucleic acid encoding the modified iLBP polypeptide. In addition, the kit can include a container comprising an enzyme for joining or ligating the nucleic acid encoding the modified iLBP polypeptide with a selected nucleic acid (e.g., a nucleic acid encoding a fusion partner).

Instructions for manipulating and/or using the nucleic acid encoding the modified iLBP polypeptide can also be provided in the kit.

Other containers and materials can be present within the kit. For example, the kit can include at least one container comprising a retinoid or a dye ligand. The kit can contain primers for amplifying or further modifying the sequence of the nucleic acid encoding the modified iLBP polypeptide. The kit can include a container comprising Dpn I endonuclease for specifically cleaving methylated and/or hemimethylated DNA. The kit can include a container with host cells that can be transformed with the nucleic acid encoding the modified iLBP polypeptide, or an expression cassette or vector comprising nucleic acid encoding the modified iLBP polypeptide. The kit can also include materials for purifying or precipitating nucleic acids (e.g., after cleavage, ligation or other manipulations) and/or materials for purifying and/or concentrating a modified iLBP polypeptide or a fusion protein comprising a modified iLBP polypeptide. The kit can also include solutions for dissolving or suspending a modified iLBP polypeptide and/or a fusion protein.

Another aspect of the invention is a kit that includes at least one a container comprising a modified iLBP polypeptide. This kit can also include at least one container comprising a retinoid or a dye ligand. In some embodiments, the kit can include reagents for fusing the modified iLBP polypeptide to another molecule of interest (e.g., a fusion partner). The kit can also include materials or solutions for purifying, dissolving or suspending the modified iLBP polypeptide and/or a fusion protein.

Instructions for manipulating and/or using the modified iLBP polypeptide can also be provided in the kit.

The following non-limiting examples illustrate certain aspects of the invention and some of the methods used in the development of the invention.

EXAMPLE 1

Materials and Methods

This Example describes some of the materials and methods used in developing the invention.
Generation of CRBP Mutant Polypeptides CRBP mutants were made using "Quick Change" mutagenesis procedures, although no commercial kit was employed. A double-stranded DNA vector encoding a selected CRBP sequences was prepared, as well as two synthetic oligonucleotide primers containing the desired mutation. The ends of the oligonucleotide primers also contained DNA that was complementary to opposite strands of the vector. The CRBP-containing DNA vector was extended using the mutant primers and a thermally stable DNA polymerase (e.g., PfuTurbo® DNA polymerase) during polymerase chain reaction (PCR) thermal cycling. By incorporation of the oligonucleotide primers into the CRBP-containing DNA vector, a mutated plasmid containing staggered nicks was generated. After this primer-extension reaction, the product is treated with Dpn I endonuclease (target sequence: 5'-Gm6ATC-3'), which specifically cleaves methylated and hemimethylated DNA. DNA isolated from E. coli is dam-methylated and is susceptible to Dpn I digestion. Cleavage with Dpn I endonuclease therefore digested the parental DNA template that is methylated but not the mutated CRBP DNA that was synthesized by primer-extension.

The nicked DNA plasmids containing the desired CRBP mutations were then transformed into E. coli host cells for expression of the mutant CRBP protein.
Binding of Retinal and Merocyanine Dyes to the CRBP Polypeptides The modified CRBP polypeptides were mixed with retinal, typically at a stoichiometric ratio of about 2:1 and the absorption/transmission of light by these retinal:CRBP complexes was measured using a Cary 300 Bio WinUV, Varian spectrometer.

In addition, a merocyanine dye with the following structure was mixed with the modified CRBP polypeptides, typically at a molar ratio of about 1:2.

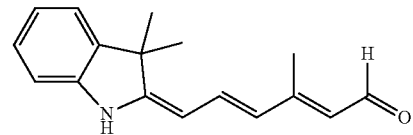 [SMILES: CC(/C=C/C=C1/Nc2ccccc2C1(C)C)=C\C=O]

The light absorption and transmission properties of the CRBP:merocyanine dye were also measured by obtaining ultraviolet-visible range spectra of these complexes using a Cary 300 Bio WinUV, Varian spectrometer or, for fluorescence, a Fluorolog-3 spectrometer.

EXAMPLE 2

The Modified CRBP Polypeptides Transmit Light at a Variety of Wavelengths

This Example illustrates that modified CRBP polypeptides transmit light at a variety of wavelengths when combined with a retinoid or fluorescent dye ligand.

A variety of CRBP mutants were expressed in separate aliquots of E. coli host cells, and the mutant CRBP proteins were isolated by ion exchange chromatography. The CRBP protein preparations were suspended in phosphate buffered saline (PBS). Retinal at a molar ratio of about 1:2 was mixed with each mutant CRBP preparation and an ultraviolet-visible range spectrum of each CRBP:retinal complex was obtained.

Figure 1A:
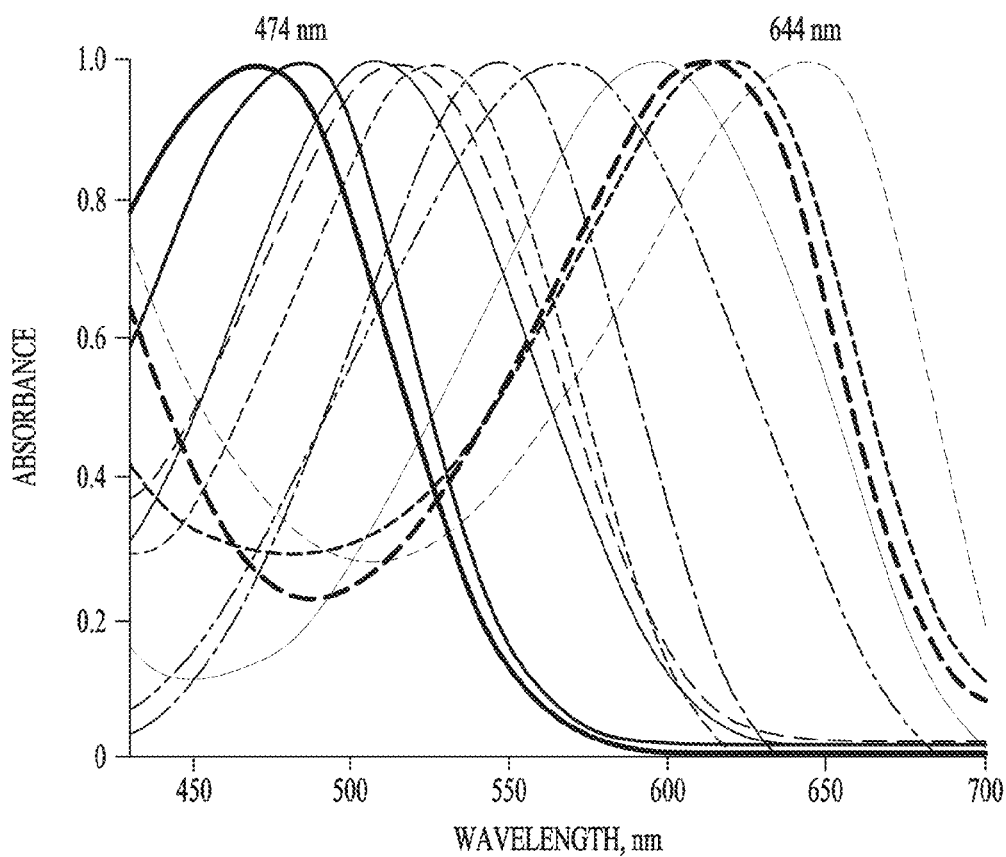
FIG. 1A illustrates the range of light colors that the modified CRBPII proteins described herein transmit. Nucleic acids encoding modified CRBPII polypeptides were expressed in *E. coli* and purified by ion exchange chromatography. Retinal was added to the purified proteins, and absorption spectra were taken of each purified protein in solution. The human CRBPII polypeptides shown have the following modifications and maximum wavelengths of absorption: Q108K:T51D ($\lambda$max=474 nm); Q108K:K40L:Y60W ($\lambda$max=512 nm); Q108K:K40L:R58F ($\lambda$max=524 nm); Q108K:K40L:R58Y ($\lambda$max=535 nm); Q108K:K40L:R58Y,T51V ($\lambda$max=563 nm); Q108K:K40L:R58W:T51V:T53C ($\lambda$max=585 nm); 108K:K40L:R58W:T51V:T53C:T291L:Y19W ($\lambda$max=591 nm); Q108K:K40L:R58W:T51V:T53C:T29L:Y19W:Q4W ($\lambda$max=613 nm); Q108K:K40L:R58W:T51V:T53C:T29L:Y19W:Q4R:A33W ($\lambda$max=644 nm). A shorthand notation is used throughout the application for describing modifications where the first letter identifies the amino acid that is naturally present in the polypeptide, number is the position of that amino acid in the polypeptide and the following letter identifies the amino acid that replaced the natural amino acid. Amino acids are identified by their single letter amino acid designations.
Figure 1B:
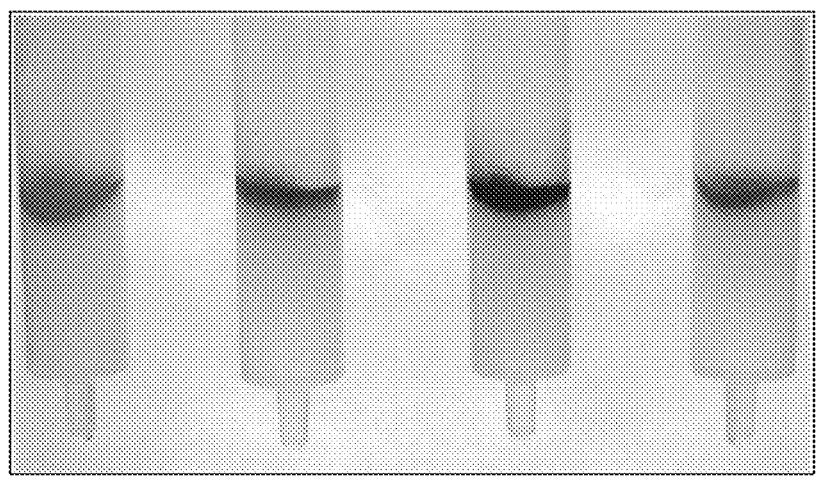
FIG. 1B shows modified CRBPII polypeptides bound to retinal when loaded onto an anion-exchange column, illustrating that the modified CRBPII polypeptides can be used as colorimetric tags for protein purification.

As shown in FIG. 1A, mutations in the human CRBP gene give rise to polypeptide products that transmit light at different wavelengths when the mutant CRBP polypeptide is complexed with retinal (other dyes can also be used). For example, a modified human CRBPII polypeptide with lysine at position 108 instead of glutamine (i.e., a Q108K hCRBPII polypeptide) maximally absorbs light at 506 nm Other human CRBPII polypeptides with various amino acid substitutions exhibit modifying light absorption and transmission properties. Thus, the following modified hCRBPII polypeptides have the indicted maximum wavelengths of absorption: Q108K:T51D ($\lambda$max=474 nm); Q108K:K40L: Y60W ($\lambda$max=512 nm); Q108K:K40L:R58F ($\lambda$max=524 nm); Q108K:K40L:R58Y ($\lambda$max=535 nm); Q108K:K40L: R58Y:T51V ($\lambda$max=563); Q108K:K40L:R58W:T51V: T53C ($\lambda$max=585 nm); 108K:K40L:R58W:T51V:T53C: T291L:Y19W ($\lambda$max=591 nm); Q108K:K40L:R58W: T51V:T53C:T29L:Y19W:Q4W ($\lambda$max=613 nm); Q108K: K40L:R58W:T51V:T53C:T29L:Y19W:Q4R ($\lambda$max=622 nm); Q108K:K40L:R58W:T51V:T53C:T29L:Y19W:Q4R: A33W ($\lambda$max=644 nm).

Examination of an x-ray crystal structure of the hCRBPII polypeptide shows that this Q108K hCRBPII modified polypeptide adopts a favorable three-dimensional structure for positioning the lysine to attack the retinal aldehyde to form a protonated Schiff base. This Schiff base can be stabilized or de-stabilized by other amino acids that are naturally present in the hCRBPII polypeptide structure, or that replace the natural amino acids. Thus, the folding of the Q108K hCRBPII modified polypeptide brings a lysine residue at about position 40 close to the Schiff base that forms between the retinal aldehyde and the nitrogen of the lysine at position 108. This lysine at position 40 perturbs the pKa of the protonated Schiff base. However, the pKa can be restored by introduction of a counter ion or replacement of the lysine. For example, when the lysine at position 40 is replaced with a leucine, a modified Q108K; K40L hCRBPII polypeptide is formed, which in combination with retinal maximally absorbs light is 508 nm.

EXAMPLE 3

Modified CRBP Polypeptides Transmit Light and/or Fluoresce In Vivo

This Example illustrates that the signal provided by modified CRBP polypeptides is not masked by other polypeptides or factors in living cells and is sufficiently strong and distinct to be useful for in vivo studies.

A variety of CRBP mutants were expressed in *E. coli* cells. Retinal was then added to the separate cell preparations containing different CRBP mutant polypeptides to ascertain whether the cells expressing these polypeptides would strongly exhibit distinctive colors. As demonstrated by FIG. 2A, the proteins clearly and specifically color the cells, indicating that these proteins provide sufficient signal to be useful for detecting the expression of proteins in living cells. Moreover, the different modifications in the CRBP polypeptides give rise to light transmission in a variety of distinct colors. Thus, different modified CRBP proteins can be employed at the same time to observe different biological functions when the different CRBP polypeptides are expressed in vivo as fusion proteins joined to selected biological products.

Figure 2:
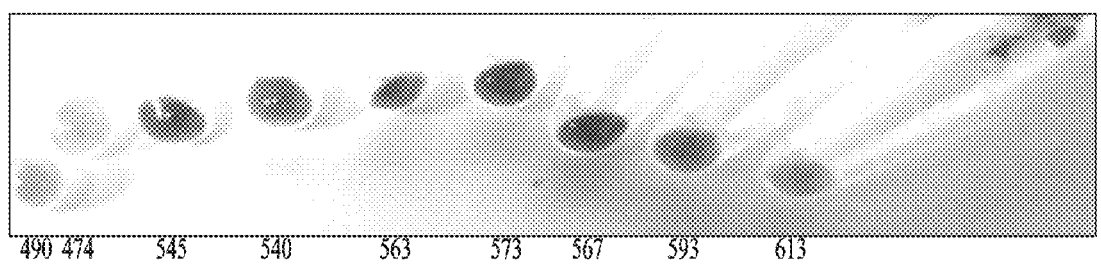
FIG. 2 illustrates colorimetric detection of modified CRBPII polypeptides within bacterial cells. Modified CRBPII polypeptides were expressed in *E. coli*, retinal was added to the cells, and the cells were spun down to show the variously colored cell pellets resulting from expression of the various colored proteins.

FIG. 2B shows that CRBP mutant polypeptides are clearly seen when bound to a standard chromatography column and that each of the colors are clearly distinct and readily identifiable. This shows that proteins fused with the mutant CRBP polypeptides can be seen at a glance during column chromatography and that many different proteins could be simultaneously observed. For example it would be possible to identify protein complexes and sub-complexes visually as they are separated chromatographically.

In another experiment, the following pH sensitive merocyanine dye was used for detecting fluorescence in living cells.

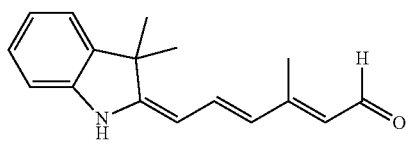

Figures 3A, 3B, 3C:
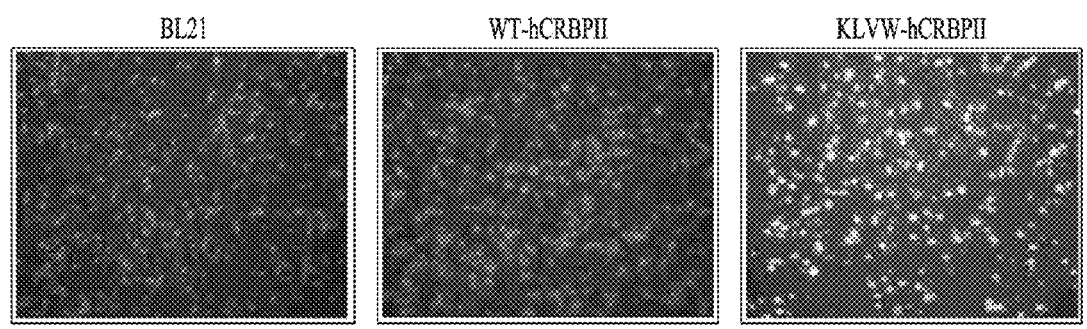
FIG. 3A-C illustrates in vivo visualization of CRBP fluorescence in *E. coli* cells using a fluorescence microscope (400× magnification) with a red filter.

A selected cellular retinol binding protein (CRBP) mutant polypeptide was expressed in *E. coli*, the merocyanine fluorescent dye shown above was added and a robust fluorescence signal was observed in bacterial cells without significant background. Cells with only the merocyanine dye exhibit essentially no fluorescence (left frame, FIG. 3A). Cells that express the wild type CRBP protein, which does not bind the merocyanine dye also exhibit no fluorescence (center frame, FIG. 3B). However, a robust fluorescence signal is clearly visible when cells expressing a modified CRBP protein that binds the dye are mixed with the merocyanine dye (right frame, FIG. 3C).

These data indicate that the merocyanine dye can penetrate bacterial cells and interact with the CRBP polypeptide as a ligand that binds the polypeptide in vivo. These data also show that background fluorescence from the dye ligand alone does not pose a significant problem. Fluorescence is achieved in this system in a matter of minutes after addition of the ligand, indicating that both transport of the dye ligand into the cell and binding are quite rapid.

EXAMPLE 4

CRBP Fusion Proteins Fluoresce in Mammalian Cells

This Example describes fusions between CRBP and Green Fluorescent protein (GFP), some of which are also fused to retinoblastoma protein (RB). The RB protein directs the fusion protein to the nucleus. As illustrated below and in the figures, the CRBP proteins exhibit strong fluorescence even when fused to other proteins.

A fusion protein was prepared by fusing a nucleic acid encoding the GFP in frame to a nucleic acid encoding a selected Q108K:K40L:T51V:R58F CRBP mutant (see schematic diagram in FIG. 4A). The sequence of this Q108K:K40L:T51V:R58F CRBP polypeptide is as follows (SEQ ID NO:39).

```
  1  TRDQNGTWEM ESNENFEGYM KALDIDFATR KIAVRLTQTL

41  VIDQDGDNFK VKTTSTFFNY DVDFTVGVEF DEYTKSLDNR

81  HVKALVTWEG DVLVCVQKGE KENRGWKKWI EGDKLYLELT

121  CGDQVCRQVF KKK
```

The sequence of this Q108K:K40L:T51V:R58F hCRBPII polypeptide with a methionine at the N-terminus is as follows (SEQ ID NO:40).

```
  1  MTRDQNGTWE MESNENFEGY MKALDIDFAT RKIAVRLTQT

41  LVIDQDGDNF KVKTTSTFFN YDVDFTVGVE FDEYTKSLDN

81  RHVKALVTWE GDVLVCVQKG EKENRGWKKW IEGDKLYLEL

121  TCGDQVCRQV FKKK
```

A separate construct was made where the GFP-CRBP construct was fused with a nucleic acid encoding Retinoblastoma Protein (RB).

The GFP-CRBP and GFP-CRBP-RB constructs were separately transfected into carcinoma cells, and the cells were observed using confocal microscopy. As shown in FIGS. 4B and 4C, the cells that fluoresce with green light irradiation (from GFP emission) also fluoresce with red light, indicating that CRBP, which is excited (and emits) in the red region of the spectrum gives rise to significant fluorescence even when fused to GFP and even when present within cells. These data also further illustrate that the merocyanine dye can pass into these cells, bind specifically to CRBP, and undergo fluorescence that is specifically correlated with the presence of the CRBP polypeptide.

EXAMPLE 5

Fluorescent pH Sensor Useful in Living Cells

The Example describes the development of a protein-based fluorescent, pH sensor that can be used in living cells.

The CRABPII polypeptide sequence SEQ ID NO:33 was modified by mutagenesis of a nucleic acid including the SEQ ID NO:34 sequence to yield a modified nucleic acid encoding an R111K:R132Q:Y134F:T54V:R59W:A32W: M93L:E73A CRABPII polypeptide. These amino acid substitutions were selected by tuning the pKa of the Schiff base because Schiff base protonation has a large effect on the absorption of this system. The sequence of this modified R111K:R132Q:Y134F:T54V:R59W:A32W:M93L:E73A CRABPII polypeptide with the N-terminal methionine (SEQ ID NO:41) is shown below:

```
  1  MPNFSGNWKI IRSENFEELL KVLGVNVMLR KIWVAAASKP
 41  AVEIKQEGDT FYIKVSTTVW TTEINFKVGE EFEAQTVDGR
 81  PCKSLVKWES ENKLVCEQKL LKGEGPKTSW TKELTNDGEL
121  ILTMTADDVV CTQVFVRE
```

The modified R111K:R132Q:Y134F:T54V:R59W: A32W:M93L:E73A CRABPII polypeptide without the N-terminal methionine is shown below (SEQ ID NO:42).

```
  1  PNFSGNWKII RSENFEELLK VLGVNVMLRK IWVAAASKPA
 41  VEIKQEGDTF YIKVSTTVWT TEINFKVGEE FEAQTVDGRP
 81  CKSLVKWESE NKLVCEQKLL KGEGPKTSWT KELTNDGELI
121  LTMTADDVVC TQVFVRE
```

Figure 5A:
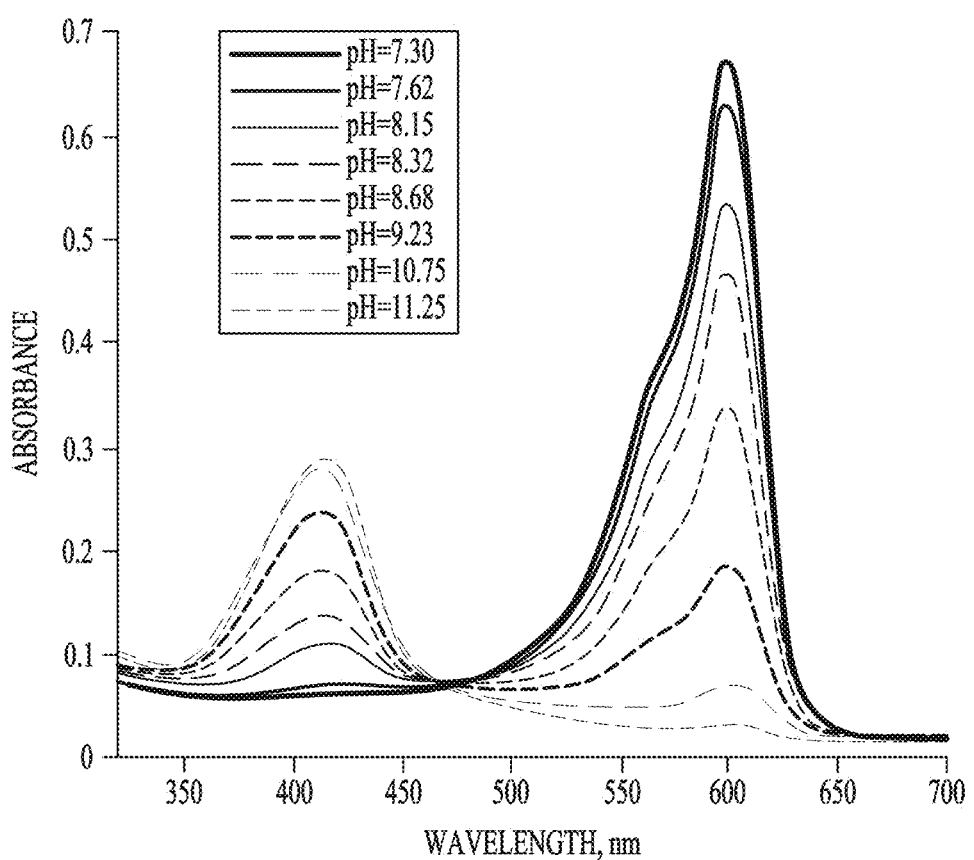
FIG. 5A-C show that modified CRABPII polypeptides can work as fluorescence-based pH sensors when combined with a fluorescent merocyanine dye.
Figure 5B:
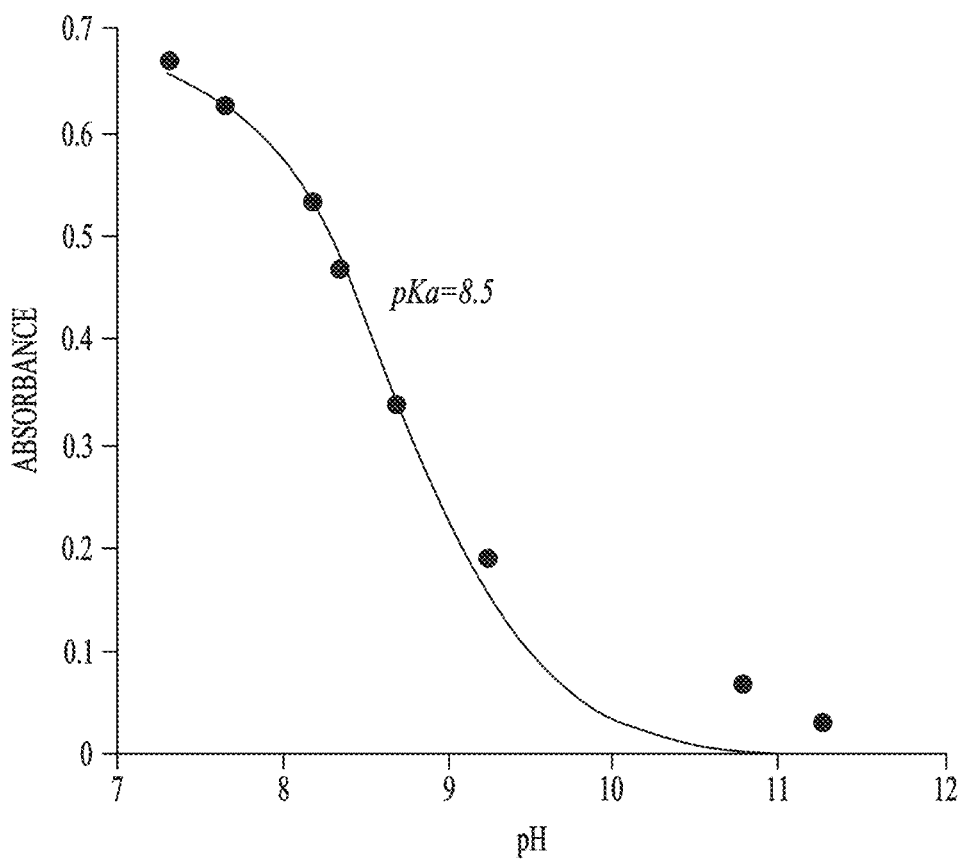
Figure 5C:
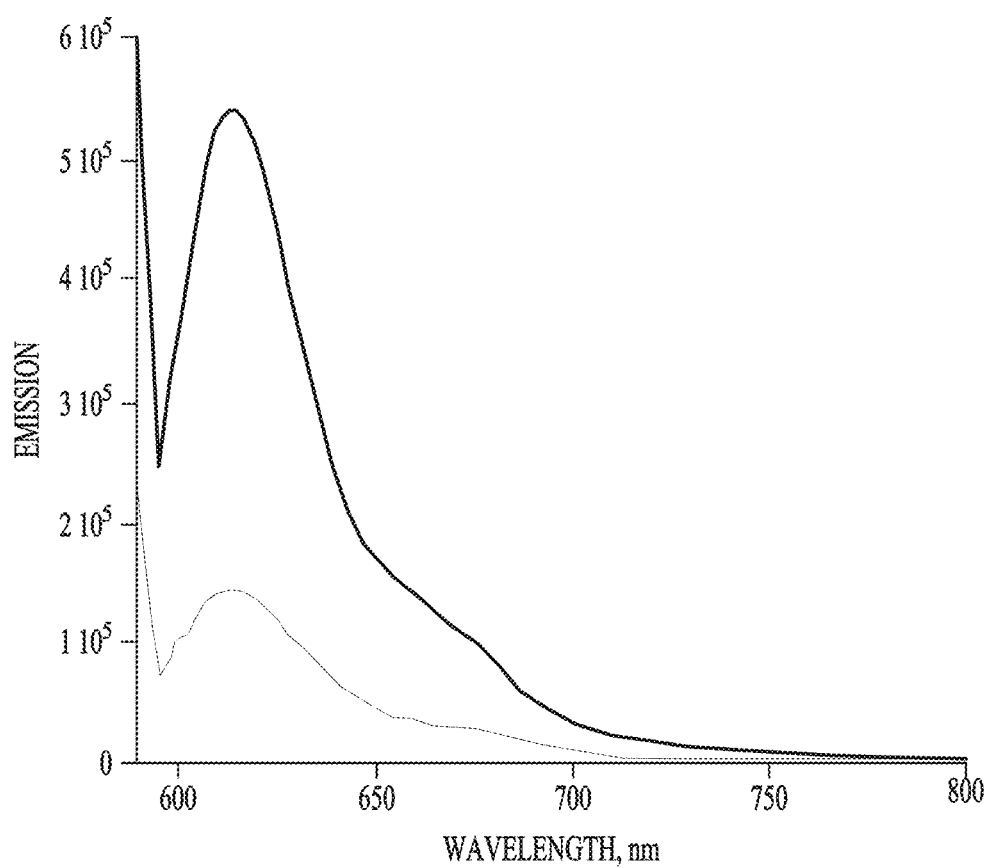

As illustrated in FIG. 5, this modified CRABPII polypeptide acts as a fluorescence-based pH sensor when combined with the merocyanine dye shown in FIG. 5C. FIG. 5A demonstrates that the color of light absorbed by this protein changes dramatically with a change in pH. Thus, at pH 11.25, the wavelength of maximum absorption is about 420 nm, but at pH 7.3 the wavelength of maximum absorption is about 600 nm. FIG. 5B shows that the smallest absorption corresponds to the highest pH and the lowest absorption corresponds to the lowest pH. This 'titration' curve was generated from the data shown in FIG. 5A. FIG. 5C shows fluorescence emission spectra of the mutant CRABPII/ merocyanine dye complex at pH 7.3 (the highest emission) and pH 8.6 (the lowest emission). The structure of the merocyanine dye at the lower and higher pH is also shown.

FIG. 6 shows the light absorption and transmission properties of two other mutant CRABPII/retinal complexes. The sequence of the first modified R111K:R132L:Y134F:T54V: R59W:A32W:M93:E73 CRABPII polypeptide with the N-terminal methionine (SEQ ID NO:43) is shown below:

```
  1  MPNFSGNWKI IRSENFEELL KVLGVNVMLR KIWVAAASKP
 41  AVEIKQEGDT FYIKVSTTVW TTEINFKVGE EFEEQTVDGR
 81  PCKSLVKWES ENKMVCEQKL LKGEGPKTSW TKELTNDGEL
121  ILTMTADDVV CTLVFVRE
```

Note that this modified CRABPII polypeptide (SEQ ID NO:41) has wild type amino acids at position 73 (E) and 93 (M).

The sequence of the second modified R111K:R132L: Y134F:T54V:R59Y:A32W:M93:E73 CRABPII polypeptide with the N-terminal methionine (SEQ ID NO:44) is shown below:

```
  1  MPNFSGNWKI IRSENFEELL KVLGVNVMLR KIWVAAASKP
 41  AVEIKQEGDT FYIKVSTTVY TTEINFKVGE EFEEQTVDGR
 81  PCKSLVKWES ENKMVCEQKL LKGEGPKTSW TKELTNDGEL
121  ILTMTADDVV CTLVFVRE
```

Note that these modified CRABPII polypeptides have wild type amino acids at position 73 (E) and 93 (M) and differ by only one amino acid at position 59.

FIG. 6A shows that the first modified CRABPII polypeptide (SEQ ID NO:43) has a darker color (blue when seen in color) at pH 5.0 and a lighter color (pale yellow when seen in color) at pH 7.3. FIG. 6B shows that this first modified CRABPII polypeptide has two strong absorption maxima at pH 5.0, one at about 375 nm and the other at about 610 nm. However, the absorption at about 610 nm of this first CRABPII polypeptide is greatly reduced at pH 7.3.

FIG. 6C shows the absorption spectrum of a second modified CRABPII polypeptide (SEQ ID NO:44), which has two strong absorption maxima at pH 5.0, one at about 375 nm and the other at about 590 nm. However, the absorption at about 590 nm of this second modified CRABPII polypeptide is greatly reduced at pH 7.3. FIG. 6D shows that the second modified CRABPII polypeptide has a darker color (purple when seen in color) at pH 5.0 and a lighter color (pale orange when seen in color) at pH 7.3.

EXAMPLE 6

Colorimetric/Fluorescent Polypeptides are Stable Across Wide Changes in Temperature and pH This Example shows that modified CRABPII polypeptides are also remarkably stable across a wide range of pH and temperature conditions.

Thermostability studies on mutant CRABPII polypeptides were carried out using circular dichroism (CD) measurements. Thermostability was assessed by observing a signal for properly folded proteins and loss of signal upon protein denaturation.

The behavior of two different CRABPII mutants was monitored as a function of temperature change. In particular, a modified CRABPII polypeptide that exhibited good thermostability has amino acid sequence SEQ ID NO:42. The thermostability of the SEQ ID NO:42 CRABPII polypeptide was compared to a R111K:R132L:Y134F CRABPII polypeptide with the following sequence (SEQ ID NO:45).

```
  1  MPNFSGNWKI IRSENFEELL KVLGVNVMLR KIAVAAASKP
 41  AVEIKQEGDT FYIKTSTTVR TTEINFKVGE EFEEQTVDGR
 81  PCKSLVKWES ENKMVCEQKL LKGEGPKTSW TKELTNDGEL
121  ILTMTADDVV CTLVFVRE
```

FIGS. 7 and 8 demonstrate that the mutant CRABPII polypeptide with SEQ ID NO:42 was remarkably stable across a wide range of pH and temperature conditions. Thus, the structure of the CRABPII polypeptide can be modified to optimize amino acid positioning and generate thermostable proteins that are also stable in acid and basic pH conditions.

These data illustrate that the mutant CRABPII/merocyanine dye complex can emit fluorescence over a wide pH range, and therefore act as pH-sensor. Because the mutant CRABPII is a polypeptide that is readily expressed in living cells, and the merocyanine dye readily penetrates living cells (see Examples 3 and 4), this system can be used as an in vivo pH sensor. When fused to a selected biological product (e.g., a fusion partner), the in vivo pH sensor can be used to sense pH changes within the biological product or in the microenvironment surrounding the biological product.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

This application therefore discloses the following embodiments

1. An isolated nucleic acid encoding a modified polypeptide selected from a member of the intracellular lipid binding protein family, wherein the modified polypeptide transmits or emits light when bound to a retinoid or fluorescent dye molecule, and wherein the intracellular lipid binding protein has been modified so that an amino acid at any of positions 102-135 can form a Schiff base with a retinoid.
2. The isolated nucleic acid of embodiment 1, which encodes a modified polypeptide that has been modified by replacement of an amino acid at any of positions 102-135 with a lysine.
3. The isolated nucleic acid of any of embodiments 1-21, which encodes a modified polypeptide that has been modified by replacement of a glutamine at any of amino acid positions 107, 108 or 109 with a lysine.
4. The isolated nucleic acid of any of embodiments 1-21, which encodes a modified polypeptide that has been modified by replacement of an arginine at any of amino acid positions 110, 111 or 112 with a lysine.
5. The isolated nucleic acid of any of embodiments 1-21, which encodes a modified polypeptide that has been modified by replacement of an arginine at any of amino acid positions 131, 132 or 133 with a lysine or a glutamine.
6. The isolated nucleic acid of any of embodiments 1-21, which encodes a modified intracellular lipid binding protein that is further modified by replacement of a lysine at any of amino acid positions 39, 40 or 41 with a leucine, serine or asparagine
7. The isolated nucleic acid of any of embodiments 1-21, which encodes a modified intracellular lipid binding protein that is further modified by replacement of a threonine at any of amino acid positions 50, 51, 52, 53, 54 or 55 with an aspartic acid, asparagine, cysteine or a valine.
8. The isolated nucleic acid of any of embodiments 1-21, which encodes a modified intracellular lipid binding protein that is further modified by replacement of a tyrosine at any of amino acid positions 59, 60 or 61 with a tryptophan, histidine, threonine, asparagine or phenylalanine.
9. The isolated nucleic acid of any of embodiments 1-21, which encodes a modified intracellular lipid binding protein that is further modified by replacement of an arginine at any of amino acid positions 57, 58, 59 or 60 with a phenylalanine, tyrosine, tryptophan, leucine, glutamine, glutamic acid, aspartic acid or alanine.
10. The isolated nucleic acid of any of embodiments 1-21, which encodes a modified intracellular lipid binding protein that is further modified by replacement of a tyrosine at any of amino acid positions 133, 134 or 135 with a phenylalanine.
11. The isolated nucleic acid of any of embodiments 1-21, which encodes a modified intracellular lipid binding protein that is further modified by replacement of a threonine at any of amino acid positions 28, 29 or 30 with a leucine, tryptophan, glutamic acid or aspartic acid.
12. The isolated nucleic acid of any of embodiments 1-21, which encodes a modified intracellular lipid binding protein that is further modified by replacement of an alanine at any of amino acid positions 30, 31, 32 or 33 with a tryptophan, phenylalanine, tyrosine, serine, histidine, glutamic acid or leucine.
13. The isolated nucleic acid of any of embodiments 1-21, which encodes a modified intracellular lipid binding protein that is further modified by replacement of a tyrosine at any of amino acid positions 18, 19 or 20 with a tryptophan or phenyalanine.

14. The isolated nucleic acid of any of embodiments 1-21, which encodes a modified intracellular lipid binding protein that is further modified by replacement of a glutamine at any of amino acid positions 3, 4 or 5 with an arginine, asparagine, phenylalanine, leucine, alanine, tryptophan, threonine, glutamic acid, histidine, or lysine.

15. The isolated nucleic acid of any of embodiments 1-21, which encodes a modified intracellular lipid binding protein that is further modified by replacement of a methionine at any of amino acid positions 92, 93 or 94 with a leucine.

16. The isolated nucleic acid of any of embodiments 1-21, which encodes a modified intracellular lipid binding protein that is further modified by replacement of a glutamic acid at any of amino acid positions 72, 73 or 74 with an alanine or leucine.

17. The isolated nucleic acid of any of embodiments 1-21, which encodes a modified intracellular lipid binding protein that is further modified by replacement of a glutamine at any of amino acid positions 36, 37 or 38 with a leucine, methionine or tryptophan.

18. The isolated nucleic acid of any of embodiments 1-21, which encodes a modified intracellular lipid binding protein that is further modified by replacement of a glutamine at any of amino acid positions 128, 129 or 130 with a leucine, lysine, glutamic acid or tryptophan.

19. The isolated nucleic acid of any of embodiments 1-21, wherein the modified intracellular lipid binding protein is a modified cellular retinoic acid binding protein II (CRABPII) or a modified cellular retinol binding protein II (CRBPII).

20. The isolated nucleic acid of any of embodiments 1-19, encoding a modified CRABPII polypeptide with amino acid sequence SEQ ID NO:46:

```
  1   MPNXSGNWKX IRXENXEELX KVLGXNVMLR KIXVAXXXXX
 41   AVEIKXEGDT FYIKXSXXXX TXEINPKVGE EFEXXTXDXR
 81   PXKSLVKWES ENKXVXEQKL LKGEGPKTSW TKELTNDGEL
121   IXTXTADDVV XTXVXVRE
``` wherein each X is independently a genetically encoded L-amino acid, a naturally-occurring non-genetically encoded L-amino acid, a synthetic L-amino acid or a synthetic D-amino acid.

21. The isolated nucleic acid of any of embodiments 1-19, encoding a modified CRBPII polypeptide with amino acid SEQ ID NO:47:

```
  1   TXDXNGTWEM ESNENXEGXX KALDXDFAXR KIXVRLTXTX
 41   VXDQDGDNFK XKXTXTXXNX DXDXTVGVEF DXYTKXXDNR
 81   HVKALVTWEG DVLVXVXKGE KENXGXKXWI EGDKLYXEXT
121   CGDQVCRXVX KKK
``` wherein each X is independently a genetically encoded L-amino acid, a naturally-occurring non-genetically encoded L-amino acid, a synthetic L-amino acid or a synthetic D-amino acid.

22. A hybrid nucleic acid comprising the isolated nucleic acid of any of embodiments 1-21 joined to a fusion partner nucleic acid that encodes a fusion partner polypeptide.

23. The hybrid nucleic acid of embodiment 22, wherein the isolated nucleic acid is joined in frame to the fusion partner nucleic acid.

24. An expression cassette comprising the isolated nucleic acid of any of embodiments 1-21 and at least one nucleic acid segment encoding a regulatory element.

25. A vector comprising the isolated nucleic acid of any of embodiments 1-21.

26. A vector comprising the expression cassette of embodiment 25.

27. A host cell comprising the isolated nucleic acid of any of embodiments 1-28.

28. The host cell of embodiment 27, wherein the isolated nucleic acid is within an expression cassette, a vector or a combination thereof.

29. A modified polypeptide selected from a member of the intracellular lipid binding protein family, wherein the modified polypeptide transmits or emits light when bound to a retinoid or fluorescent dye molecule, and wherein the intracellular lipid binding protein has been modified so that an amino acid at any of positions 102-135 can form a Schiff base with a retinoid.

30. The modified polypeptide of embodiment 29, which has been modified by replacement of the amino acid at any of positions 102-135 with a lysine.

31. The modified polypeptide of any of embodiments 29-50, which at has been modified by replacement of a glutamine at any of amino acid positions 107, 108 or 109 with a lysine.

32. The modified polypeptide of any of embodiments 29-50, which has been modified by replacement of an arginine at any of amino acid positions 110, 111 or 112 with a lysine.

33. The modified polypeptide of any of embodiments 29-50, which has been modified by replacement of an arginine at any of amino acid positions 131, 132 or 133 with a lysine or a glutamine.

34. The modified polypeptide of any of embodiments 29-50, which is further modified by replacement of a lysine at any of amino acid positions 39, 40 or 41 with a leucine, serine or asparagine.

35. The modified polypeptide of any of embodiments 29-50, which is further modified by replacement of a threonine at any of amino acid positions 50, 51, 52, 53, 54 or 55 with an aspartic acid, asparagine, cysteine or a valine.

36. The modified polypeptide of any of embodiments 29-50, which is further modified by replacement of a tyrosine at any of amino acid positions 59, 60 or 61 with a tryptophan, histidine, threonine, asparagine or phenylalanine 37. The modified polypeptide of any of embodiments 29-50, which is further modified by replacement of an arginine at any of amino acid positions 57, 58, 59 or 60 with a phenylalanine, tyrosine, tryptophan, leucine, glutamine, glutamic acid, aspartic acid or alanine.

38. The modified polypeptide of any of embodiments 29-50, which is further modified by replacement of a tyrosine at any of amino acid positions 133, 134 or 135 with a phenylalanine.

39. The modified polypeptide of any of embodiments 29-50, which is further modified by replacement of a threonine at any of amino acid positions 28, 29 or 30 with a leucine, tryptophan, glutamic acid or aspartic acid.

40. The modified polypeptide of any of embodiments 29-50, which is further modified by replacement of an alanine at any of amino acid positions 30, 31, 32 or 33 with a tryptophan, phenylalanine, tyrosine, serine, histidine, glutamic acid or leucine.

41. The modified polypeptide of any of embodiments 29-50, which is further modified by replacement of a tyrosine at any of amino acid positions 18, 19 or 20 with a tryptophan or phenylalanine.

42. The modified polypeptide of any of embodiments 29-50, which is further modified by replacement of a glutamine at any of amino acid positions 3, 4 or 5 with an arginine, asparagine, phenylalanine, leucine, alanine, tryptophan, threonine, glutamic acid, histidine, or lysine.

43. The modified polypeptide of any of embodiments 29-50, which is further modified by replacement of a methionine at any of amino acid positions 92, 93 or 94 with a leucine.

44. The modified polypeptide of any of embodiments 29-50, which is further modified by replacement of a glutamic acid at any of amino acid positions 72, 73 or 74 with an alanine or leucine.

45. The modified polypeptide of any of embodiments 29-50, which is further modified by replacement of a glutamine at any of amino acid positions 36, 37 or 38 with a leucine, methionine or tryptophan.

46. The modified polypeptide of any of embodiments 29-50, which is further modified by replacement of a glutamine at any of amino acid positions 128, 129 or 130 with a leucine, lysine, glutamic acid or tryptophan.

47. The modified polypeptide of any of embodiments 29-50, which is a modified cellular retinoic acid binding protein II (CRABPII) or a modified cellular retinol binding protein II (CRBPII).

48. The modified polypeptide of embodiment 29, which comprises an amino acid sequence selected from the group consisting of SEQ ID NO:6-28, 39-47, or a combination thereof.

49. The modified polypeptide of any of embodiments 29-50, which comprises a modified CRABPII amino acid sequence SEQ ID NO:46:

```
  1  MPNXSGNWKX IRXENXEELX KVLGXNVMLR KIXVAXXXXX
 41  AVEIKXEGDT FYIKXSXXXX TXEINFKVGE EFEXXTXDXR
 81  PXKSLVKWES ENKXVXEQKL LKGEGPKTSW TKELTNDGEL
121  IXTXTADDVV XTXVXVRE
``` wherein each X is independently a genetically encoded L-amino acid, a naturally-occurring non-genetically encoded L-amino acid, a synthetic L-amino acid or a synthetic D-amino acid.

50. The modified polypeptide of any of embodiments 29-50, which comprises a modified CRBPII amino acid sequence SEQ ID NO:47:

```
  1  TXDXNGTWEM ESNENXEGXX KALDXDFAXR KIXVRLTXTX
 41  VXDQDGDNFK XKXTXTXXNX DXDXTVGVEF DXYTKXXDNR
 81  HVKALVTWEG DVLVXVXKGE KENXGXKXWI EGDKLYXEXT
121  CGDQVCRXVX KKK
``` wherein each X is independently a genetically encoded L-amino acid, a naturally-occurring non-genetically encoded L-amino acid, a synthetic L-amino acid or a synthetic D-amino acid.

51. The modified polypeptide of any of embodiments 29-50, which is mixed with or complexed with a retinoid or dye ligand.

52. A fusion protein comprising the modified polypeptide of any of embodiments 29-51 fused to another protein.

53. A kit comprising at least one container comprising the isolated nucleic acid of any of embodiments 1-21, and a second container comprising a retinoid or dye ligand that binds a modified polypeptide encoded by the isolated nucleic acid, wherein the isolated nucleic acid can be within an expression cassette or vector.

54. A kit comprising at least one container comprising the modified polypeptide of any of embodiments 29-50 and a second container comprising a retinoid or dye ligand that binds a modified polypeptide.

55. A method of observing a target protein in vivo comprising contacting a living cell with a retinoid or dye ligand that binds a modified polypeptide encoded by the isolated nucleic acid of any of embodiments 1-21, wherein the cell expresses a fusion protein comprising the modified polypeptide fused in frame with the target protein.

56. The method of embodiment 55, wherein the dye ligand is a compound of formula I:

$$\text{Ring-Y—CHO}$$

wherein:

Ring is an optionally substituted $C_5$-$C_{14}$ mono-, di- or tricyclic cycloalkyl, aryl or heterocyclic ring, wherein the heterocyclic ring has at least one nitrogen or oxygen ring atom, and wherein the Ring has 1-3 optional substituents that are selected from the group consisting of alkyl, halogen, alkoxy, amino and sulfhydryl; and Y is a divalent $C_2$-$C_{12}$ alkenylene chain that optionally substituted with 1-3 alkyl groups.

57. The method of embodiment 55, wherein the retinoid is retinal.

58. A method of making a colorimetric and/or fluorescent protein comprising modifying a nucleic acid encoding an intracellular lipid binding protein family member to generate a modified iLBP polypeptide wherein the modified iLBP polypeptide transmits or emits light when bound to a retinoid or fluorescent dye molecule, and wherein the intracellular lipid binding protein has been modified so that an amino acid at any of positions 102-135 can form a Schiff base with a retinoid (e.g., retinal).

59. The method of embodiment 58, wherein the nucleic is modified to encode the modified polypeptide of any of embodiments 29-50.

60. The method of embodiment 58 or 59 further comprising contacting the modified polypeptide with a retinal or dye ligand.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A CRBPII polypeptide comprising at least 95% sequence identity to SEQ ID NO: 5, said polypeptide comprising a mutation corresponding to Q108K in SEQ ID NO: 5, said polypeptide capable of transmitting or emitting light when bound to a retinoid or fluorescent dye molecule.

2. The polypeptide of claim 1, wherein the polypeptide further comprises an N-terminal methionine.

3. The polypeptide of claim 1, wherein the polypeptide has amino acid sequence substitutions in SEQ ID NO: 5 as set forth in:
   SEQ ID NO: 7, wherein the amino acid substitutions are Q108K and K40L;
   SEQ ID NO: 8, wherein the amino acid substitutions are Q108K and T51D;
   SEQ ID NO: 9, wherein the amino acid substitutions are Q108K, K40L, and Y60W;
   SEQ ID NO: 10, wherein the amino acid substitutions are Q108K, K40L, and T51V;
   SEQ ID NO: 11, wherein the amino acid substitutions are Q108K, K40L, and R58F;
   SEQ ID NO: 12, wherein the amino acid substitutions are Q108K, K40L, and R58Y;
   SEQ ID NO: 13, wherein the amino acid substitutions are Q108K, T51V, and R58Y;
   SEQ ID NO: 14, wherein the amino acid substitutions are Q108K, K40L, T51V, and R58W;
   SEQ ID NO: 15, wherein the amino acid substitutions are Q108K, K40L, T51V, R58W, and T53C;
   SEQ ID NO: 16, wherein the amino acid substitutions are Q108K, K40L, T51V, R58W, T53C, and T29L;
   SEQ ID NO: 17, wherein the amino acid substitutions are Q108K, K40L, T51V, R58W, T53C, T29L, and Y19W;
   SEQ ID NO: 18, wherein the amino acid substitutions are Q108K, K40L, T51V, R58W, T53C, T29L, Y19W, and Q4R;
   SEQ ID NO: 20, wherein the amino acid substitutions are Q108K, K40L, T51V, R58W, T53C, T29L, Y19W, and Q4W;
   SEQ ID NO: 21, wherein the amino acid substitutions are Q108K, K40L, T51V, R58W, T53C, T29L, Y19W, and Q4N;
   SEQ ID NO: 22, wherein the amino acid substitutions are Q108K, K40L, T51V, R58W, T53C, T29L, Y19W, and Q4T;
   SEQ ID NO: 23, wherein the amino acid substitutions are Q108K, K40L, T51V, R58W, T53C, T29L, Y19W, and Q4E;
   SEQ ID NO: 24, wherein the amino acid substitutions are Q108K, K40L, T51V, R58W, T53C, T29L, Y19W, and Q4H;

SEQ ID NO: 25, wherein the amino acid substitutions are Q108K, K40L, T51V, R58W, T53C, T29L, Y19W, and Q4K;

SEQ ID NO: 26, wherein the amino acid substitutions are Q108K, K40L, T51V, R58W, T53C, T29L, Y19W, and Q4L;

SEQ ID NO: 27, wherein the amino acid substitutions are Q108K, K40L, T51V, R58W, T53C, T29L, Y19W, and Q4F; or SEQ ID NO: 28, wherein the amino acid substitutions are Q108K, K40L, T51V, R58W, T53C, T29L, Y19W, Q4R, and A33W.

4. A nucleic acid encoding the polypeptide of claim 1.

5. An expression cassette comprising the nucleic acid of claim 4.

6. A vector comprising the expression cassette of claim 5.

7. A hybrid nucleic acid comprising the nucleic acid of claim 4 joined to a fusion partner nucleic acid that encodes a fusion partner polypeptide.

8. An expression cassette comprising the nucleic acid of claim 7.

9. A vector comprising the expression cassette of claim 8.

10. A method of observing a target protein in vivo comprising contacting a living cell with a retinoid or dye ligand that binds a modified polypeptide encoded by the isolated nucleic acid of claim 7, wherein the cell expresses a fusion protein comprising the modified polypeptide fused in frame with the target protein.

11. The method of claim 10 wherein the dye ligand is a compound of formula I:

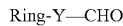

wherein:

Ring is an optionally substituted C5-C14 mono-, di- or tricyclic cycloalkyl, aryl or heterocyclic ring, wherein the heterocyclic ring has at least one nitrogen or oxygen ring atom, and wherein the Ring has 1-3 optional substituents that are selected from the group consisting of alkyl, halogen, alkoxy, amino and sulfhydryl; and Y is a divalent C2-C12 alkenylene chain that optionally substituted with 1-3 alkyl groups.

12. The method of claim 10, wherein the retinoid is retinal.

13. A CRABPII polypeptide comprising at least 95% sequence identity to SEQ ID NO: 33, said polypeptide comprising a mutation corresponding to Q118K in SEQ ID NO: 33, said polypeptide capble of-transmiting or emitting light when bound to a retinoid or fluorescent dye molecule.

14. The polypeptide of claim 13, wherein the polypeptide does not have an N-terminal methionine.

15. The polypeptide of claim 13, wherein the polypeptide has amino acid sequence substitutions in SEQ ID NO: 33 as set forth in:

SEQ ID NO: 41, wherein the amino acid substitutions are R111K, R132Q, Y134F, T54V, R59W, A32W, M93L, and E73A;

SEQ ID NO: 43, wherein the amino acid substitutions are R111K, R132Q, Y134F, T54V, R59W, and A32W;

SEQ ID NO: 44, wherein the amino acid substitutions are R111K, R132L, Y134F, T54V, R59W, and A32W; and SEQ ID NO: 45, wherein the amino acid substitutions are R111K, R132L, and Y134F.

16. A nucleic acid encoding the polypeptide of claim 13.

17. An expression cassette comprising the nucleic acid of claim 16.

18. A vector comprising the expression cassette of claim 17.

19. A hybrid nucleic acid comprising the nucleic acid of claim 16 joined to a fusion partner nucleic acid that encodes a fusion partner polypeptide.

20. An expression cassette comprising the nucleic acid of claim 19.

21. A vector comprising the expression cassette of claim 20.

22. A method of observing a target protein in vivo comprising contacting a living cell with a retinoid or dye ligand that binds a modified polypeptide encoded by the isolated nucleic acid of claim 19, wherein the cell expresses a fusion protein comprising the modified polypeptide fused in frame with the target protein.

23. The method of claim 22, wherein the dye ligand is a compound of Formula I:

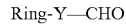

wherein:

Ring is an optionally substituted C5-C14 mono-, di- or tricyclic cycloalkyl, aryl or heterocyclic ring, wherein the heterocyclic ring has at least one nitrogen or oxygen ring atom, and wherein the Ring has 1-3 optional substituents that are selected from the group consisting of alkyl, halogen, alkoxy, amino and sulfhydryl; and Y is a divalent C2-C12 alkenylene chain that optionally substituted with 1-3 alkyl groups.

24. The method of claim 22, wherein the retinoid is retinal.

* * * * *

UNITED STATES PATENT AND TRADEMARK OFFICE
CERTIFICATE OF CORRECTION

PATENT NO. : 9,732,127 B2  
APPLICATION NO. : 14/883944  
DATED : August 15, 2017  
INVENTOR(S) : Borhan et al.

Page 1 of 1

It is certified that error appears in the above-identified patent and that said Letters Patent is hereby corrected as shown below:

On the Title Page

In item (60), in "Related U.S. Application Data", in Column 1, Line 2, delete "2011." and insert --2010.-- therefor In the Claims In Column 109, Line 63, in Claim 3, delete "R58F:" and insert --R58F;-- therefor In Column 109, Line 65, in Claim 3, delete "R58Y:" and insert --R58Y;-- therefor In Column 109, Line 67, in Claim 3, after "Q108K,", insert --K40L,--

In Column 111, Line 29, in Claim 11, after "claim 10", insert --,--

In Column 111, Line 34, in Claim 11, delete "C5-C14" and insert --$C_5$-$C_{14}$-- therefor In Column 111, Line 40, in Claim 11, delete "C2-C12" and insert --$C_2$-$C_{12}$-- therefor In Column 112, Line 34, in Claim 23, delete "Formula" and insert --formula-- therefor In Column 112, Line 38, in Claim 23, delete "C5-C14" and insert --$C_5$-$C_{14}$-- therefor In Column 112, Line 44, in Claim 23, delete "C2-C12" and insert --$C_2$-$C_{12}$-- therefor Signed and Sealed this  
Twenty-fourth Day of April, 2018

Andrei Iancu  
*Director of the United States Patent and Trademark Office*